United States Patent
Johnson et al.

(10) Patent No.: US 12,354,263 B2
(45) Date of Patent: Jul. 8, 2025

(54) REGISTRATION OF 3D AND 2D IMAGES FOR SURGICAL NAVIGATION AND ROBOTIC GUIDANCE WITHOUT USING RADIOPAQUE FIDUCIALS IN THE IMAGES

(71) Applicant: GLOBUS MEDICAL, INC., Audubon, PA (US)

(72) Inventors: Norbert Johnson, North Andover, MA (US); Paden Troxell, Conshohocken, PA (US); Caroline Conrad, Emmaus, PA (US); Mert Erad, Malden, MA (US); Nicholas Maritato, Cambridge, MA (US); Michael Brauckmann, Woburn, MA (US); Neil R. Crawford, Chandler, AZ (US)

(73) Assignee: Globus Medical Inc., Audubon, PA (US)

( * ) Notice: Subject to any disclaimer, the term of this patent is extended or adjusted under 35 U.S.C. 154(b) by 276 days.

(21) Appl. No.: 18/194,170

(22) Filed: Mar. 31, 2023

(65) Prior Publication Data
US 2024/0020862 A1    Jan. 18, 2024

Related U.S. Application Data

(63) Continuation of application No. 18/184,192, filed on Mar. 15, 2023.
(Continued)

(51) Int. Cl.
*G06T 7/00* (2017.01)
*A61B 6/00* (2006.01)
(Continued)

(52) U.S. Cl.
CPC .......... *G06T 7/0012* (2013.01); *A61B 6/4441* (2013.01); *A61B 6/582* (2013.01);
(Continued)

(58) Field of Classification Search
CPC ....... G06T 7/0012; G06T 7/0014; G06T 7/30; G06T 7/344; G06T 7/70; G06T 7/75;
(Continued)

(56) References Cited

U.S. PATENT DOCUMENTS 4,150,293 A    4/1979 Franke
5,246,010 A    9/1993 Gazzara et al.
(Continued)

FOREIGN PATENT DOCUMENTS

EP    3306567 A1    4/2018
EP    3306567 B1    3/2020
(Continued)

OTHER PUBLICATIONS

US 8,231,638 B2, 07/2012, Swarup et al. (withdrawn)

*Primary Examiner* — William A Beutel

(57) ABSTRACT

System and method of registering a medical image of a patient in an imaging space to the patient in a physical space preferably without the use of any embedded radiopaque fiducials in medical images is provided. In one way, intra-op 2D medical images are used to register a pre-op unregistered 3D medical image. The 2D medical images are registered based on simultaneous tracking of the tracking markers on the imaging device and on the patient by a tracking device at the time of image capture. The 2D images are matched to corresponding simulated 2D images generated from the pre-op 3D image volume. Thus, registration of a pre-op 3D image to the patient is accomplished without performing another 3D scan of the patient.

20 Claims, 40 Drawing Sheets

Related U.S. Application Data

(60) Provisional application No. 63/389,691, filed on Jul. 15, 2022.

(51) Int. Cl.

| | | |
|---|---|---|
| *A61B 6/58* | (2024.01) | |
| *A61B 34/20* | (2016.01) | |
| *A61B 34/30* | (2016.01) | |
| *A61B 90/00* | (2016.01) | |
| *G06F 3/14* | (2006.01) | |
| *G06T 7/30* | (2017.01) | |
| *G06T 7/33* | (2017.01) | |
| *G06T 7/70* | (2017.01) | |
| *G06T 7/73* | (2017.01) | |
| *G06T 15/08* | (2011.01) | |
| *G06T 15/20* | (2011.01) | |
| *G06T 17/00* | (2006.01) | |
| *G06T 19/00* | (2011.01) | |
| *G16H 30/20* | (2018.01) | |

(52) U.S. Cl.
CPC ............. *A61B 34/20* (2016.02); *A61B 34/30* (2016.02); *A61B 90/39* (2016.02); *G06F 3/14* (2013.01); *G06T 7/0014* (2013.01); *G06T 7/30* (2017.01); *G06T 7/344* (2017.01); *G06T 7/70* (2017.01); *G06T 7/75* (2017.01); *G06T 15/08* (2013.01); *G06T 15/205* (2013.01); *G06T 17/00* (2013.01); *G06T 19/00* (2013.01); *G16H 30/20* (2018.01); *A61B 2034/2055* (2016.02); *A61B 2090/3966* (2016.02); *G06T 2200/04* (2013.01); *G06T 2207/10132* (2013.01); *G06T 2207/30004* (2013.01); *G06T 2207/30196* (2013.01); *G06T 2207/30208* (2013.01); *G06T 2207/30244* (2013.01); *G06T 2210/41* (2013.01)

(58) Field of Classification Search
CPC ....... G06T 15/08; G06T 15/205; G06T 17/00; G06T 19/00; G06T 2200/04; G06T 2207/10132; G06T 2207/30004; G06T 2207/30196; G06T 2207/30208; G06T 2207/30244; G06T 2210/41; G06T 7/20; G06T 7/80; G06T 2207/10021; G06T 2207/10072; G06T 2207/10121; G06T 2207/30204; G06T 2207/30241; A61B 6/4441; A61B 6/582; A61B 34/20; A61B 34/30; A61B 90/39; A61B 2034/2055; A61B 2090/3966; A61B 6/5235; A61B 6/547; A61B 6/487; A61B 2017/00725; A61B 2090/3762; A61B 2090/3764; A61B 2090/378; A61B 2090/3983; A61B 6/5247; A61B 2090/364; A61B 2090/376; G06F 3/14; G16H 30/20; G16H 20/40; G16H 50/50; G16H 30/40; G09G 2340/12; G09G 5/377; G09G 2380/08
See application file for complete search history.

(56) References Cited

U.S. PATENT DOCUMENTS

| | | |
|---|---|---|
| 5,354,314 A | 10/1994 | Hardy et al. |
| 5,397,323 A | 3/1995 | Taylor et al. |
| 5,598,453 A | 1/1997 | Baba et al. |
| 5,772,594 A | 6/1998 | Barrick |
| 5,791,908 A | 8/1998 | Gillio |
| 5,820,559 A | 10/1998 | Ng et al. |
| 5,825,982 A | 10/1998 | Wright et al. |
| 5,887,121 A | 3/1999 | Funda et al. |
| 5,911,449 A | 6/1999 | Daniele et al. |
| 5,951,475 A | 9/1999 | Gueziec et al. |
| 5,987,960 A | 11/1999 | Messner et al. |
| 6,012,216 A | 1/2000 | Esteves et al. |
| 6,031,888 A | 2/2000 | Ivan et al. |
| 6,033,415 A | 3/2000 | Mittelstadt et al. |
| 6,080,181 A | 6/2000 | Jensen et al. |
| 6,106,511 A | 8/2000 | Jensen |
| 6,122,541 A | 9/2000 | Cosman et al. |
| 6,144,875 A | 11/2000 | Schweikard et al. |
| 6,157,853 A | 12/2000 | Blume et al. |
| 6,167,145 A | 12/2000 | Foley et al. |
| 6,167,292 A | 12/2000 | Badano et al. |
| 6,201,984 B1 | 3/2001 | Funda et al. |
| 6,203,196 B1 | 3/2001 | Meyer et al. |
| 6,205,411 B1 | 3/2001 | DiGioia, III et al. |
| 6,212,419 B1 | 4/2001 | Blume et al. |
| 6,231,565 B1 | 5/2001 | Tovey et al. |
| 6,236,875 B1 | 5/2001 | Bucholz et al. |
| 6,246,900 B1 | 6/2001 | Cosman et al. |
| 6,301,495 B1 | 10/2001 | Gueziec et al. |
| 6,306,126 B1 | 10/2001 | Montezuma |
| 6,312,435 B1 | 11/2001 | Wallace et al. |
| 6,314,311 B1 | 11/2001 | Williams et al. |
| 6,320,929 B1 | 11/2001 | Von Der Haar |
| 6,322,567 B1 | 11/2001 | Mittelstadt et al. |
| 6,325,808 B1 | 12/2001 | Bernard et al. |
| 6,340,363 B1 | 1/2002 | Bolger et al. |
| 6,377,011 B1 | 4/2002 | Ben-Ur |
| 6,379,302 B1 | 4/2002 | Kessman et al. |
| 6,402,762 B2 | 6/2002 | Hunter et al. |
| 6,424,885 B1 | 7/2002 | Niemeyer et al. |
| 6,447,503 B1 | 9/2002 | Wynne et al. |
| 6,451,027 B1 | 9/2002 | Cooper et al. |
| 6,477,400 B1 | 11/2002 | Barrick |
| 6,484,049 B1 | 11/2002 | Seeley et al. |
| 6,487,267 B1 | 11/2002 | Wolter |
| 6,490,467 B1 | 12/2002 | Bucholz et al. |
| 6,490,475 B1 | 12/2002 | Seeley et al. |
| 6,499,488 B1 | 12/2002 | Hunter et al. |
| 6,501,981 B1 | 12/2002 | Schweikard et al. |
| 6,507,751 B2 | 1/2003 | Blume et al. |
| 6,535,756 B1 | 3/2003 | Simon et al. |
| 6,560,354 B1 | 5/2003 | Maurer, Jr. et al. |
| 6,565,554 B1 | 5/2003 | Niemeyer |
| 6,587,750 B2 | 7/2003 | Gerbi et al. |
| 6,614,453 B1 | 9/2003 | Suri et al. |
| 6,614,871 B1 | 9/2003 | Kobiki et al. |
| 6,619,840 B2 | 9/2003 | Rasche et al. |
| 6,636,757 B1 | 10/2003 | Jascob et al. |
| 6,645,196 B1 | 11/2003 | Nixon et al. |
| 6,666,579 B2 | 12/2003 | Jensen |
| 6,669,635 B2 | 12/2003 | Kessman et al. |
| 6,701,173 B2 | 3/2004 | Nowinski et al. |
| 6,757,068 B2 | 6/2004 | Foxlin |
| 6,782,287 B2 | 8/2004 | Grzeszczuk et al. |
| 6,783,524 B2 | 8/2004 | Anderson et al. |
| 6,786,896 B1 | 9/2004 | Madhani et al. |
| 6,788,018 B1 | 9/2004 | Blumenkranz |
| 6,804,581 B2 | 10/2004 | Wang et al. |
| 6,823,207 B1 | 11/2004 | Jensen et al. |
| 6,827,351 B2 | 12/2004 | Graziani et al. |
| 6,837,892 B2 | 1/2005 | Shoham |
| 6,839,612 B2 | 1/2005 | Sanchez et al. |
| 6,856,826 B2 | 2/2005 | Seeley et al. |
| 6,856,827 B2 | 2/2005 | Seeley et al. |
| 6,879,880 B2 | 4/2005 | Nowlin et al. |
| 6,892,090 B2 | 5/2005 | Verard et al. |
| 6,920,347 B2 | 7/2005 | Simon et al. |
| 6,922,632 B2 | 7/2005 | Foxlin |
| 6,968,224 B2 | 11/2005 | Kessman et al. |
| 6,978,166 B2 | 12/2005 | Foley et al. |
| 6,988,009 B2 | 1/2006 | Grimm et al. |
| 6,991,627 B2 | 1/2006 | Madhani et al. |
| 6,996,487 B2 | 2/2006 | Jutras et al. |
| 6,999,852 B2 | 2/2006 | Green |
| 7,007,699 B2 | 3/2006 | Martinelli et al. |
| 7,016,457 B1 | 3/2006 | Senzig et al. |
| 7,029,175 B2 | 4/2006 | Karaus et al. |

(56) References Cited

U.S. PATENT DOCUMENTS

| | | |
|---|---|---|
| 7,043,961 B2 | 5/2006 | Pandey et al. |
| 7,062,006 B1 | 6/2006 | Pelc et al. |
| 7,063,705 B2 | 6/2006 | Young et al. |
| 7,072,707 B2 | 7/2006 | Galloway, Jr. et al. |
| 7,083,615 B2 | 8/2006 | Peterson et al. |
| 7,097,640 B2 | 8/2006 | Wang et al. |
| 7,099,428 B2 | 8/2006 | Clinthorne et al. |
| 7,108,421 B2 | 9/2006 | Gregerson et al. |
| 7,130,676 B2 | 10/2006 | Barrick |
| 7,139,418 B2 | 11/2006 | Abovitz et al. |
| 7,139,601 B2 | 11/2006 | Bucholz et al. |
| 7,155,316 B2 | 12/2006 | Sutherland et al. |
| 7,164,968 B2 | 1/2007 | Treat et al. |
| 7,167,738 B2 | 1/2007 | Schweikard et al. |
| 7,169,141 B2 | 1/2007 | Brock et al. |
| 7,172,627 B2 | 2/2007 | Fiere et al. |
| 7,194,120 B2 | 3/2007 | Wicker et al. |
| 7,197,107 B2 | 3/2007 | Arai et al. |
| 7,231,014 B2 | 6/2007 | Levy |
| 7,231,063 B2 | 6/2007 | Naimark et al. |
| 7,239,940 B2 | 7/2007 | Wang et al. |
| 7,248,914 B2 | 7/2007 | Hastings et al. |
| 7,301,648 B2 | 11/2007 | Foxlin |
| 7,302,288 B1 | 11/2007 | Schellenberg |
| 7,313,430 B2 | 12/2007 | Urquhart et al. |
| 7,318,805 B2 | 1/2008 | Schweikard et al. |
| 7,318,827 B2 | 1/2008 | Leitner et al. |
| 7,319,897 B2 | 1/2008 | Leitner et al. |
| 7,324,623 B2 | 1/2008 | Heuscher et al. |
| 7,327,865 B2 | 2/2008 | Fu et al. |
| 7,331,967 B2 | 2/2008 | Lee et al. |
| 7,333,642 B2 | 2/2008 | Green |
| 7,339,341 B2 | 3/2008 | Oleynikov et al. |
| 7,366,562 B2 | 4/2008 | Dukesherer et al. |
| 7,379,790 B2 | 5/2008 | Toth et al. |
| 7,386,365 B2 | 6/2008 | Nixon |
| 7,422,592 B2 | 9/2008 | Morley et al. |
| 7,435,216 B2 | 10/2008 | Kwon et al. |
| 7,440,793 B2 | 10/2008 | Chauhan et al. |
| 7,460,637 B2 | 12/2008 | Clinthorne et al. |
| 7,466,303 B2 | 12/2008 | Yi et al. |
| 7,493,153 B2 | 2/2009 | Ahmed et al. |
| 7,505,617 B2 | 3/2009 | Fu et al. |
| 7,519,415 B2 | 4/2009 | Mitschke et al. |
| 7,533,892 B2 | 5/2009 | Schena et al. |
| 7,542,791 B2 | 6/2009 | Mire et al. |
| 7,555,331 B2 | 6/2009 | Viswanathan |
| 7,567,834 B2 | 7/2009 | Clayton et al. |
| 7,594,912 B2 | 9/2009 | Cooper et al. |
| 7,606,613 B2 | 10/2009 | Simon et al. |
| 7,607,440 B2 | 10/2009 | Coste-Maniere et al. |
| 7,623,902 B2 | 11/2009 | Pacheco |
| 7,630,752 B2 | 12/2009 | Viswanathan |
| 7,630,753 B2 | 12/2009 | Simon et al. |
| 7,643,862 B2 | 1/2010 | Schoenefeld |
| 7,660,623 B2 | 2/2010 | Hunter et al. |
| 7,661,881 B2 | 2/2010 | Gregerson et al. |
| 7,683,331 B2 | 3/2010 | Chang |
| 7,683,332 B2 | 3/2010 | Chang |
| 7,689,320 B2 | 3/2010 | Prisco et al. |
| 7,691,098 B2 | 4/2010 | Wallace et al. |
| 7,702,379 B2 | 4/2010 | Avinash et al. |
| 7,702,477 B2 | 4/2010 | Tuemmler et al. |
| 7,711,083 B2 | 5/2010 | Heigl et al. |
| 7,711,406 B2 | 5/2010 | Kuhn et al. |
| 7,720,523 B2 | 5/2010 | Omernick et al. |
| 7,725,253 B2 | 5/2010 | Foxlin |
| 7,726,171 B2 | 6/2010 | Langlotz et al. |
| 7,742,801 B2 | 6/2010 | Neubauer et al. |
| 7,751,865 B2 | 7/2010 | Jascob et al. |
| 7,760,849 B2 | 7/2010 | Zhang |
| 7,762,825 B2 | 7/2010 | Burbank et al. |
| 7,763,015 B2 | 7/2010 | Cooper et al. |
| 7,782,998 B2 | 8/2010 | Angan et al. |
| 7,787,699 B2 | 8/2010 | Mahesh et al. |
| 7,796,728 B2 | 9/2010 | Bergfjord |
| 7,802,642 B2 | 9/2010 | Jensen et al. |
| 7,813,838 B2 | 10/2010 | Sommer |
| 7,818,044 B2 | 10/2010 | Dukesherer et al. |
| 7,819,859 B2 | 10/2010 | Prisco et al. |
| 7,824,401 B2 | 11/2010 | Manzo et al. |
| 7,831,294 B2 | 11/2010 | Viswanathan |
| 7,834,484 B2 | 11/2010 | Sartor |
| 7,835,557 B2 | 11/2010 | Kendrick et al. |
| 7,835,778 B2 | 11/2010 | Foley et al. |
| 7,835,784 B2 | 11/2010 | Mire et al. |
| 7,840,253 B2 | 11/2010 | Tremblay et al. |
| 7,840,256 B2 | 11/2010 | Lakin et al. |
| 7,843,158 B2 | 11/2010 | Prisco |
| 7,844,320 B2 | 11/2010 | Shahidi |
| 7,853,305 B2 | 12/2010 | Simon et al. |
| 7,853,313 B2 | 12/2010 | Thompson |
| 7,865,269 B2 | 1/2011 | Prisco et al. |
| D631,966 S | 2/2011 | Perloff et al. |
| 7,879,045 B2 | 2/2011 | Gielen et al. |
| 7,881,767 B2 | 2/2011 | Strommer et al. |
| 7,881,770 B2 | 2/2011 | Melkent et al. |
| 7,886,743 B2 | 2/2011 | Cooper et al. |
| RE42,194 E | 3/2011 | Foley et al. |
| RE42,226 E | 3/2011 | Foley et al. |
| 7,900,524 B2 | 3/2011 | Calloway et al. |
| 7,907,166 B2 | 3/2011 | Lamprecht et al. |
| 7,909,122 B2 | 3/2011 | Schena et al. |
| 7,925,653 B2 | 4/2011 | Saptharishi |
| 7,930,065 B2 | 4/2011 | Larkin et al. |
| 7,935,130 B2 | 5/2011 | Williams |
| 7,940,999 B2 | 5/2011 | Liao et al. |
| 7,945,012 B2 | 5/2011 | Ye et al. |
| 7,945,021 B2 | 5/2011 | Shapiro et al. |
| 7,953,470 B2 | 5/2011 | Vetter et al. |
| 7,954,397 B2 | 6/2011 | Choi et al. |
| 7,971,341 B2 | 7/2011 | Dukesherer et al. |
| 7,974,674 B2 | 7/2011 | Hauck et al. |
| 7,974,677 B2 | 7/2011 | Mire et al. |
| 7,974,681 B2 | 7/2011 | Wallace et al. |
| 7,979,157 B2 | 7/2011 | Anvari |
| 7,983,733 B2 | 7/2011 | Viswanathan |
| 7,988,215 B2 | 8/2011 | Seibold |
| 7,996,110 B2 | 8/2011 | Lipow et al. |
| 8,004,121 B2 | 8/2011 | Sartor |
| 8,004,229 B2 | 8/2011 | Nowlin et al. |
| 8,010,177 B2 | 8/2011 | Csavoy et al. |
| 8,019,045 B2 | 9/2011 | Kato |
| 8,021,310 B2 | 9/2011 | Sanborn et al. |
| 8,035,685 B2 | 10/2011 | Jensen |
| 8,046,054 B2 | 10/2011 | Kim et al. |
| 8,046,057 B2 | 10/2011 | Clarke |
| 8,052,688 B2 | 11/2011 | Wolf, II |
| 8,054,184 B2 | 11/2011 | Cline et al. |
| 8,054,752 B2 | 11/2011 | Druke et al. |
| 8,057,397 B2 | 11/2011 | Li et al. |
| 8,057,407 B2 | 11/2011 | Martinelli et al. |
| 8,062,288 B2 | 11/2011 | Cooper et al. |
| 8,062,375 B2 | 11/2011 | Glerum et al. |
| 8,066,524 B2 | 11/2011 | Burbank et al. |
| 8,073,335 B2 | 12/2011 | Labonville et al. |
| 8,079,950 B2 | 12/2011 | Stern et al. |
| 8,086,299 B2 | 12/2011 | Adler et al. |
| 8,092,370 B2 | 1/2012 | Roberts et al. |
| 8,098,914 B2 | 1/2012 | Liao et al. |
| 8,100,950 B2 | 1/2012 | St. Clair et al. |
| 8,105,320 B2 | 1/2012 | Manzo |
| 8,108,025 B2 | 1/2012 | Csavoy et al. |
| 8,109,877 B2 | 2/2012 | Moctezuma de la Barrera et al. |
| 8,112,292 B2 | 2/2012 | Simon |
| 8,116,430 B1 | 2/2012 | Shapiro et al. |
| 8,120,301 B2 | 2/2012 | Goldberg et al. |
| 8,121,249 B2 | 2/2012 | Wang et al. |
| 8,123,675 B2 | 2/2012 | Funda et al. |
| 8,133,229 B1 | 3/2012 | Bonutti |
| 8,142,420 B2 | 3/2012 | Schena |
| 8,147,494 B2 | 4/2012 | Leitner et al. |
| 8,150,494 B2 | 4/2012 | Simon et al. |
| 8,150,497 B2 | 4/2012 | Gielen et al. |

(56) References Cited

U.S. PATENT DOCUMENTS

| | | |
|---|---|---|
| 8,150,498 B2 | 4/2012 | Gielen et al. |
| 8,165,658 B2 | 4/2012 | Waynik et al. |
| 8,170,313 B2 | 5/2012 | Kendrick et al. |
| 8,175,365 B2 | 5/2012 | Edlauer et al. |
| 8,179,073 B2 | 5/2012 | Farritor et al. |
| 8,182,476 B2 | 5/2012 | Julian et al. |
| 8,184,880 B2 | 5/2012 | Zhao et al. |
| 8,202,278 B2 | 6/2012 | Orban et al. |
| 8,208,708 B2 | 6/2012 | Homan et al. |
| 8,208,988 B2 | 6/2012 | Jenser |
| 8,219,177 B2 | 7/2012 | Smith et al. |
| 8,219,178 B2 | 7/2012 | Smith et al. |
| 8,220,468 B2 | 7/2012 | Cooper et al. |
| 8,224,024 B2 | 7/2012 | Foxlin et al. |
| 8,224,484 B2 | 7/2012 | Swarup et al. |
| 8,225,798 B2 | 7/2012 | Baldwin et al. |
| 8,228,368 B2 | 7/2012 | Zhao et al. |
| 8,231,610 B2 | 7/2012 | Jo et al. |
| 8,263,933 B2 | 7/2012 | Hartmann et al. |
| 8,239,001 B2 | 8/2012 | Verard et al. |
| 8,241,271 B2 | 8/2012 | Millman et al. |
| 8,248,413 B2 | 8/2012 | Gattani et al. |
| 8,256,319 B2 | 9/2012 | Cooper et al. |
| 8,271,069 B2 | 9/2012 | Jascob et al. |
| 8,271,130 B2 | 9/2012 | Hourtash |
| 8,281,670 B2 | 10/2012 | Arkin et al. |
| 8,282,653 B2 | 10/2012 | Nelson et al. |
| 8,301,226 B2 | 10/2012 | Csavoy et al. |
| 8,311,611 B2 | 11/2012 | Csavoy et al. |
| 8,320,991 B2 | 11/2012 | Jascob et al. |
| 8,332,012 B2 | 12/2012 | Kienzle, III |
| 8,333,755 B2 | 12/2012 | Cooper et al. |
| 8,335,552 B2 | 12/2012 | Stiles |
| 8,335,557 B2 | 12/2012 | Maschke |
| 8,348,931 B2 | 1/2013 | Cooper et al. |
| 8,353,963 B2 | 1/2013 | Glerum |
| 8,358,818 B2 | 1/2013 | Miga et al. |
| 8,359,730 B2 | 1/2013 | Burg et al. |
| 8,374,673 B2 | 2/2013 | Adcox et al. |
| 8,374,723 B2 | 2/2013 | Zhao et al. |
| 8,379,791 B2 | 2/2013 | Forthmann et al. |
| 8,386,019 B2 | 2/2013 | Camus et al. |
| 8,392,022 B2 | 3/2013 | Ortmaier et al. |
| 8,394,099 B2 | 3/2013 | Patwardhan |
| 8,395,342 B2 | 3/2013 | Prisco |
| 8,398,634 B2 | 3/2013 | Manzo et al. |
| 8,400,094 B2 | 3/2013 | Schena |
| 8,414,957 B2 | 4/2013 | Enzerink et al. |
| 8,418,073 B2 | 4/2013 | Mohr et al. |
| 8,450,694 B2 | 5/2013 | Baviera et al. |
| 8,452,447 B2 | 5/2013 | Nixon |
| RE44,305 E | 6/2013 | Foley et al. |
| 8,462,911 B2 | 6/2013 | Vesel et al. |
| 8,465,476 B2 | 6/2013 | Rogers et al. |
| 8,465,771 B2 | 6/2013 | Wan et al. |
| 8,467,851 B2 | 6/2013 | Mire et al. |
| 8,467,852 B2 | 6/2013 | Csavoy et al. |
| 8,469,947 B2 | 6/2013 | Devengenzo et al. |
| RE44,392 E | 7/2013 | Hynes |
| 8,483,434 B2 | 7/2013 | Buehner et al. |
| 8,483,800 B2 | 7/2013 | Jensen et al. |
| 8,486,532 B2 | 7/2013 | Enzerink et al. |
| 8,489,235 B2 | 7/2013 | Moll et al. |
| 8,500,722 B2 | 8/2013 | Cooper |
| 8,500,728 B2 | 8/2013 | Newton et al. |
| 8,504,201 B2 | 8/2013 | Moll et al. |
| 8,506,555 B2 | 8/2013 | Ruiz Morales |
| 8,506,556 B2 | 8/2013 | Schena |
| 8,508,173 B2 | 8/2013 | Goldberg et al. |
| 8,512,318 B2 | 8/2013 | Tovey et al. |
| 8,515,576 B2 | 8/2013 | Lipow et al. |
| 8,518,120 B2 | 8/2013 | Glerum et al. |
| 8,521,331 B2 | 8/2013 | Itkowitz |
| 8,526,688 B2 | 9/2013 | Groszmann et al. |
| 8,526,700 B2 | 9/2013 | Isaacs |
| 8,527,094 B2 | 9/2013 | Kumar et al. |
| 8,528,440 B2 | 9/2013 | Morley et al. |
| 8,532,741 B2 | 9/2013 | Heruth et al. |
| 8,541,970 B2 | 9/2013 | Nowlin et al. |
| 8,548,563 B2 | 10/2013 | Simon et al. |
| 8,549,732 B2 | 10/2013 | Burg et al. |
| 8,551,114 B2 | 10/2013 | Ramos de la Pena |
| 8,551,116 B2 | 10/2013 | Julian et al. |
| 8,556,807 B2 | 10/2013 | Scott et al. |
| 8,556,979 B2 | 10/2013 | Glerum et al. |
| 8,560,118 B2 | 10/2013 | Green et al. |
| 8,561,473 B2 | 10/2013 | Blumenkranz |
| 8,562,594 B2 | 10/2013 | Cooper et al. |
| 8,571,638 B2 | 10/2013 | Shoham |
| 8,571,710 B2 | 10/2013 | Coste-Maniere et al. |
| 8,573,465 B2 | 11/2013 | Shelton, IV |
| 8,574,303 B2 | 11/2013 | Sharkey et al. |
| 8,585,420 B2 | 11/2013 | Burbank et al. |
| 8,594,841 B2 | 11/2013 | Zhao et al. |
| 8,597,198 B2 | 12/2013 | Sanborn et al. |
| 8,600,478 B2 | 12/2013 | Verard et al. |
| 8,603,077 B2 | 12/2013 | Cooper et al. |
| 8,611,985 B2 | 12/2013 | Lavallee et al. |
| 8,613,230 B2 | 12/2013 | Blumenkranz et al. |
| 8,621,939 B2 | 1/2014 | Blumenkranz et al. |
| 8,624,537 B2 | 1/2014 | Nowlin et al. |
| 8,630,389 B2 | 1/2014 | Kato |
| 8,634,897 B2 | 1/2014 | Simon et al. |
| 8,634,957 B2 | 1/2014 | Toth et al. |
| 8,638,056 B2 | 1/2014 | Goldberg et al. |
| 8,638,057 B2 | 1/2014 | Goldberg et al. |
| 8,639,000 B2 | 1/2014 | Zhao et al. |
| 8,641,726 B2 | 2/2014 | Bonutti |
| 8,644,907 B2 | 2/2014 | Hartmann et al. |
| 8,657,494 B2 | 2/2014 | Muller et al. |
| 8,657,809 B2 | 2/2014 | Schoepp |
| 8,660,635 B2 | 2/2014 | Simon et al. |
| 8,666,544 B2 | 3/2014 | Moll et al. |
| 8,675,939 B2 | 3/2014 | Moctezuma De La Barrera |
| 8,678,647 B2 | 3/2014 | Gregerson et al. |
| 8,679,125 B2 | 3/2014 | Smith et al. |
| 8,679,183 B2 | 3/2014 | Glerum et al. |
| 8,682,413 B2 | 3/2014 | Lloyd |
| 8,684,253 B2 | 4/2014 | Giordano et al. |
| 8,685,098 B2 | 4/2014 | Glerum et al. |
| 8,693,730 B2 | 4/2014 | Umasuthan et al. |
| 8,694,075 B2 | 4/2014 | Groszmann et al. |
| 8,696,458 B2 | 4/2014 | Foxlin et al. |
| 8,700,123 B2 | 4/2014 | Okamura et al. |
| 8,706,086 B2 | 4/2014 | Glerum |
| 8,706,185 B2 | 4/2014 | Foley et al. |
| 8,706,301 B2 | 4/2014 | Zhao et al. |
| 8,717,430 B2 | 5/2014 | Simon et al. |
| 8,727,618 B2 | 5/2014 | Maschke et al. |
| 8,734,432 B2 | 5/2014 | Tuma et al. |
| 8,738,115 B2 | 5/2014 | Amberg et al. |
| 8,738,181 B2 | 5/2014 | Greer et al. |
| 8,740,882 B2 | 6/2014 | Jun et al. |
| 8,746,252 B2 | 6/2014 | McGrogan et al. |
| 8,749,189 B2 | 6/2014 | Nowlin et al. |
| 8,749,190 B2 | 6/2014 | Nowlin et al. |
| 8,761,930 B2 | 6/2014 | Nixon |
| 8,764,448 B2 | 7/2014 | Yang et al. |
| 8,771,170 B2 | 7/2014 | Mesallum et al. |
| 8,781,186 B2 | 7/2014 | Clements et al. |
| 8,781,630 B2 | 7/2014 | Banks et al. |
| 8,784,385 B2 | 7/2014 | Boyden et al. |
| 8,786,241 B2 | 7/2014 | Nowlin et al. |
| 8,787,520 B2 | 7/2014 | Baba |
| 8,792,704 B2 | 7/2014 | Isaacs |
| 8,798,231 B2 | 8/2014 | Notohara et al. |
| 8,800,838 B2 | 8/2014 | Shelton, IV |
| 8,808,164 B2 | 8/2014 | Hoffman et al. |
| 8,812,077 B2 | 8/2014 | Dempsey |
| 8,814,793 B2 | 8/2014 | Brabrand |
| 8,816,628 B2 | 8/2014 | Nowlin et al. |
| 8,818,105 B2 | 8/2014 | Myronenko et al. |
| 8,820,605 B2 | 9/2014 | Shelton, IV |
| 8,821,511 B2 | 9/2014 | Von Jako et al. |

(56) References Cited

U.S. PATENT DOCUMENTS

| | | |
|---|---|---|
| 8,823,308 B2 | 9/2014 | Nowlin et al. |
| 8,827,996 B2 | 9/2014 | Scott et al. |
| 8,828,024 B2 | 9/2014 | Farritor et al. |
| 8,830,224 B2 | 9/2014 | Zhao et al. |
| 8,834,489 B2 | 9/2014 | Cooper et al. |
| 8,834,490 B2 | 9/2014 | Bonutti |
| 8,838,270 B2 | 9/2014 | Druke et al. |
| 8,844,789 B2 | 9/2014 | Shelton, IV et al. |
| 8,855,822 B2 | 10/2014 | Bartol et al. |
| 8,858,598 B2 | 10/2014 | Seifert et al. |
| 8,860,753 B2 | 10/2014 | Bhandarkar et al. |
| 8,864,751 B2 | 10/2014 | Prisco et al. |
| 8,864,798 B2 | 10/2014 | Weiman et al. |
| 8,864,833 B2 | 10/2014 | Glerum et al. |
| 8,867,703 B2 | 10/2014 | Shapiro et al. |
| 8,870,880 B2 | 10/2014 | Himmelberger et al. |
| 8,876,866 B2 | 11/2014 | Zappacosta et al. |
| 8,880,223 B2 | 11/2014 | Raj et al. |
| 8,882,803 B2 | 11/2014 | Iott et al. |
| 8,883,210 B1 | 11/2014 | Truncale et al. |
| 8,888,821 B2 | 11/2014 | Rezach et al. |
| 8,888,853 B2 | 11/2014 | Glerum et al. |
| 8,888,854 B2 | 11/2014 | Glerum et al. |
| 8,894,652 B2 | 11/2014 | Seifert et al. |
| 8,894,688 B2 | 11/2014 | Suh |
| 8,894,691 B2 | 11/2014 | Iott et al. |
| 8,906,069 B2 | 12/2014 | Hansell et al. |
| 8,964,934 B2 | 2/2015 | Ein-Gal |
| 8,992,580 B2 | 3/2015 | Bar et al. |
| 8,996,169 B2 | 3/2015 | Lightcap et al. |
| 9,001,963 B2 | 4/2015 | Sowards-Emmerd et al. |
| 9,002,076 B2 | 4/2015 | Khadem et al. |
| 9,044,190 B2 | 6/2015 | Rubner et al. |
| 9,107,683 B2 | 8/2015 | Hourtash et al. |
| 9,125,556 B2 | 9/2015 | Zehavi et al. |
| 9,131,986 B2 | 9/2015 | Greer et al. |
| 9,173,628 B2 | 11/2015 | Bouvier et al. |
| 9,215,968 B2 | 12/2015 | Schostek et al. |
| 9,248,000 B2 | 2/2016 | Sarvestani et al. |
| 9,308,050 B2 | 4/2016 | Kostrzewski et al. |
| 9,380,984 B2 | 7/2016 | Li et al. |
| 9,393,039 B2 | 7/2016 | Lechner et al. |
| 9,398,886 B2 | 7/2016 | Gregerson et al. |
| 9,398,890 B2 | 7/2016 | Dong et al. |
| 9,414,859 B2 | 8/2016 | Ballard et al. |
| 9,420,975 B2 | 8/2016 | Gutfleisch et al. |
| 9,492,235 B2 | 11/2016 | Hourtash et al. |
| 9,545,235 B2 | 1/2017 | Bouvier et al. |
| 9,592,096 B2 | 3/2017 | Maillet et al. |
| 9,750,465 B2 | 9/2017 | Engel et al. |
| 9,757,203 B2 | 9/2017 | Hourtash et al. |
| 9,795,354 B2 | 10/2017 | Menegaz et al. |
| 9,814,535 B2 | 11/2017 | Bar et al. |
| 9,820,783 B2 | 11/2017 | Donner et al. |
| 9,833,265 B2 | 11/2017 | Donner et al. |
| 9,848,922 B2 | 12/2017 | Tohmeh et al. |
| 9,925,011 B2 | 3/2018 | Gombert et al. |
| 9,931,025 B1 | 4/2018 | Graetzel et al. |
| 9,974,502 B2 | 5/2018 | Bouvier et al. |
| 10,034,717 B2 | 7/2018 | Miller et al. |
| 10,039,613 B2 | 8/2018 | Hartmann et al. |
| 10,265,137 B2 | 4/2019 | Glossop |
| 10,413,260 B2 | 9/2019 | Bouvier et al. |
| 10,413,270 B2 | 9/2019 | Noda et al. |
| 10,463,447 B2 | 11/2019 | Sela et al. |
| 10,639,125 B2 | 5/2020 | De Mathelin et al. |
| 10,799,316 B2 | 10/2020 | Sela et al. |
| 10,813,608 B2 | 10/2020 | Ferreira et al. |
| 11,253,216 B2 | 2/2022 | Crawford et al. |
| 11,295,460 B1 | 4/2022 | Aghdasi et al. |
| 11,350,995 B2 | 6/2022 | Finley et al. |
| 2001/0036302 A1 | 11/2001 | Miller |
| 2002/0035321 A1 | 3/2002 | Bucholz et al. |
| 2004/0068172 A1 | 4/2004 | Nowinski et al. |
| 2004/0076259 A1 | 4/2004 | Jensen et al. |
| 2005/0096502 A1 | 5/2005 | Khalili |
| 2005/0143651 A1 | 6/2005 | Verard et al. |
| 2005/0171558 A1 | 8/2005 | Abovitz et al. |
| 2006/0100610 A1 | 5/2006 | Wallace et al. |
| 2006/0173329 A1 | 8/2006 | Marquart et al. |
| 2006/0184396 A1 | 8/2006 | Dennis et al. |
| 2006/0241416 A1 | 10/2006 | Marquart et al. |
| 2006/0291612 A1 | 12/2006 | Nishide et al. |
| 2007/0015987 A1 | 1/2007 | Benlloch Baviera et al. |
| 2007/0021738 A1 | 1/2007 | Hasser et al. |
| 2007/0038059 A1 | 2/2007 | Sheffer et al. |
| 2007/0073133 A1 | 3/2007 | Schoenefeld |
| 2007/0156121 A1 | 7/2007 | Millman et al. |
| 2007/0156157 A1 | 7/2007 | Nahum et al. |
| 2007/0167712 A1 | 7/2007 | Keglovich et al. |
| 2007/0233238 A1 | 10/2007 | Huynh et al. |
| 2008/0004523 A1 | 1/2008 | Jensen |
| 2008/0013809 A1 | 1/2008 | Zhu et al. |
| 2008/0033283 A1 | 2/2008 | Dellaca et al. |
| 2008/0046122 A1 | 2/2008 | Manzo et al. |
| 2008/0082109 A1 | 4/2008 | Moll et al. |
| 2008/0108912 A1 | 5/2008 | Node-Langlois |
| 2008/0108991 A1 | 5/2008 | Von Jako |
| 2008/0109012 A1 | 5/2008 | Falco et al. |
| 2008/0144906 A1 | 6/2008 | Allred et al. |
| 2008/0161680 A1 | 7/2008 | Von Jako et al. |
| 2008/0161682 A1 | 7/2008 | Kendrick et al. |
| 2008/0177203 A1 | 7/2008 | von Jako |
| 2008/0214922 A1 | 9/2008 | Hartmann et al. |
| 2008/0228068 A1 | 9/2008 | Viswanathan et al. |
| 2008/0228196 A1 | 9/2008 | Wang et al. |
| 2008/0235052 A1 | 9/2008 | Node-Langlois et al. |
| 2008/0269596 A1 | 10/2008 | Revie et al. |
| 2008/0287771 A1 | 11/2008 | Anderson |
| 2008/0287781 A1 | 11/2008 | Revie et al. |
| 2008/0300477 A1 | 12/2008 | Lloyd et al. |
| 2008/0300478 A1 | 12/2008 | Zuhars et al. |
| 2008/0302950 A1 | 12/2008 | Park et al. |
| 2008/0306490 A1 | 12/2008 | Lakin et al. |
| 2008/0319311 A1 | 12/2008 | Hamadeh |
| 2009/0012509 A1 | 1/2009 | Csavoy et al. |
| 2009/0030428 A1 | 1/2009 | Omori et al. |
| 2009/0080737 A1 | 3/2009 | Battle et al. |
| 2009/0185655 A1 | 7/2009 | Koken et al. |
| 2009/0198121 A1 | 8/2009 | Hoheisel |
| 2009/0216113 A1 | 8/2009 | Meier et al. |
| 2009/0228019 A1 | 9/2009 | Gross et al. |
| 2009/0259123 A1 | 10/2009 | Navab et al. |
| 2009/0259230 A1 | 10/2009 | Khadem et al. |
| 2009/0264899 A1 | 10/2009 | Appenrodt et al. |
| 2009/0281417 A1 | 11/2009 | Hartmann et al. |
| 2010/0022874 A1 | 1/2010 | Wang et al. |
| 2010/0039506 A1 | 2/2010 | Sarvestani et al. |
| 2010/0125286 A1 | 5/2010 | Wang et al. |
| 2010/0130986 A1 | 5/2010 | Mailloux et al. |
| 2010/0228117 A1 | 9/2010 | Hartmann |
| 2010/0228265 A1 | 9/2010 | Prisco |
| 2010/0249571 A1 | 9/2010 | Jensen et al. |
| 2010/0274120 A1 | 10/2010 | Heuscher |
| 2010/0280363 A1 | 11/2010 | Skarda et al. |
| 2010/0331858 A1 | 12/2010 | Simaan et al. |
| 2011/0022229 A1 | 1/2011 | Jang et al. |
| 2011/0077504 A1 | 3/2011 | Fischer et al. |
| 2011/0098553 A1 | 4/2011 | Robbins et al. |
| 2011/0137152 A1 | 6/2011 | Li |
| 2011/0213384 A1 | 9/2011 | Jeong |
| 2011/0224684 A1 | 9/2011 | Larkin et al. |
| 2011/0224685 A1 | 9/2011 | Larkin et al. |
| 2011/0224686 A1 | 9/2011 | Larkin et al. |
| 2011/0224687 A1 | 9/2011 | Larkin et al. |
| 2011/0224688 A1 | 9/2011 | Larkin et al. |
| 2011/0224689 A1 | 9/2011 | Larkin et al. |
| 2011/0224825 A1 | 9/2011 | Larkin et al. |
| 2011/0230967 A1 | 9/2011 | O'Halloran et al. |
| 2011/0238080 A1 | 9/2011 | Ranjit et al. |
| 2011/0276058 A1 | 11/2011 | Choi et al. |
| 2011/0282189 A1 | 11/2011 | Graumann |
| 2011/0286573 A1 | 11/2011 | Schretter et al. |
| 2011/0295062 A1 | 12/2011 | Solsona et al. |

(56) References Cited

U.S. PATENT DOCUMENTS

| | | |
|---|---|---|
| 2011/0295370 A1 | 12/2011 | Suh et al. |
| 2011/0306986 A1 | 12/2011 | Lee et al. |
| 2012/0035507 A1 | 2/2012 | George et al. |
| 2012/0046668 A1 | 2/2012 | Gantes |
| 2012/0051498 A1 | 3/2012 | Koishi |
| 2012/0053597 A1 | 3/2012 | Anvari et al. |
| 2012/0059248 A1 | 3/2012 | Holsing et al. |
| 2012/0071753 A1 | 3/2012 | Hunter et al. |
| 2012/0108954 A1 | 5/2012 | Schulhauser et al. |
| 2012/0136372 A1 | 5/2012 | Amat Girbau et al. |
| 2012/0143084 A1 | 6/2012 | Shoham |
| 2012/0184839 A1 | 7/2012 | Woerlein |
| 2012/0197182 A1 | 8/2012 | Millman et al. |
| 2012/0226145 A1 | 9/2012 | Chang et al. |
| 2012/0235909 A1 | 9/2012 | Birkenbach et al. |
| 2012/0245596 A1 | 9/2012 | Meenink |
| 2012/0253332 A1 | 10/2012 | Moll |
| 2012/0253360 A1 | 10/2012 | White et al. |
| 2012/0256092 A1 | 10/2012 | Zingerman |
| 2012/0294498 A1 | 11/2012 | Popovic |
| 2012/0296203 A1 | 11/2012 | Hartmann et al. |
| 2013/0006267 A1 | 1/2013 | Odermatt et al. |
| 2013/0016889 A1 | 1/2013 | Myronenko et al. |
| 2013/0030571 A1 | 1/2013 | Ruiz Morales et al. |
| 2013/0035583 A1 | 2/2013 | Park et al. |
| 2013/0060146 A1 | 3/2013 | Yang et al. |
| 2013/0060337 A1 | 3/2013 | Petersheim et al. |
| 2013/0094742 A1 | 4/2013 | Feilkas |
| 2013/0096574 A1 | 4/2013 | Kang et al. |
| 2013/0113791 A1 | 5/2013 | Isaacs et al. |
| 2013/0116706 A1 | 5/2013 | Lee et al. |
| 2013/0131695 A1 | 5/2013 | Scarfogliero et al. |
| 2013/0144307 A1 | 6/2013 | Jeong et al. |
| 2013/0158542 A1 | 6/2013 | Manzo et al. |
| 2013/0165937 A1 | 6/2013 | Patwardhan |
| 2013/0178867 A1 | 7/2013 | Farritor et al. |
| 2013/0178868 A1 | 7/2013 | Roh |
| 2013/0178870 A1 | 7/2013 | Schena |
| 2013/0204271 A1 | 8/2013 | Brisson et al. |
| 2013/0211419 A1 | 8/2013 | Jensen |
| 2013/0211420 A1 | 8/2013 | Jensen |
| 2013/0218142 A1 | 8/2013 | Tuma et al. |
| 2013/0223702 A1 | 8/2013 | Holsing et al. |
| 2013/0225942 A1 | 8/2013 | Holsing et al. |
| 2013/0225943 A1 | 8/2013 | Holsing et al. |
| 2013/0231556 A1 | 9/2013 | Holsing et al. |
| 2013/0237995 A1 | 9/2013 | Lee et al. |
| 2013/0245375 A1 | 9/2013 | DiMaio et al. |
| 2013/0261640 A1 | 10/2013 | Kim et al. |
| 2013/0272488 A1 | 10/2013 | Bailey et al. |
| 2013/0272489 A1 | 10/2013 | Dickman et al. |
| 2013/0274761 A1 | 10/2013 | Devengenzo et al. |
| 2013/0281821 A1 | 10/2013 | Liu et al. |
| 2013/0296884 A1 | 11/2013 | Taylor et al. |
| 2013/0303887 A1 | 11/2013 | Holsing et al. |
| 2013/0307955 A1 | 11/2013 | Deitz et al. |
| 2013/0317521 A1 | 11/2013 | Choi et al. |
| 2013/0325033 A1 | 12/2013 | Schena et al. |
| 2013/0325035 A1 | 12/2013 | Hauck et al. |
| 2013/0331686 A1 | 12/2013 | Freysinger et al. |
| 2013/0331858 A1 | 12/2013 | Devengenzo et al. |
| 2013/0331861 A1 | 12/2013 | Yoon |
| 2013/0342578 A1 | 12/2013 | Isaacs |
| 2013/0345717 A1 | 12/2013 | Markvicka et al. |
| 2013/0345757 A1 | 12/2013 | Stad |
| 2014/0001235 A1 | 1/2014 | Shelton, IV |
| 2014/0012131 A1 | 1/2014 | Heruth et al. |
| 2014/0031664 A1 | 1/2014 | Kang et al. |
| 2014/0046128 A1 | 2/2014 | Lee et al. |
| 2014/0046132 A1 | 2/2014 | Hoeg et al. |
| 2014/0046340 A1 | 2/2014 | Wilson et al. |
| 2014/0049629 A1 | 2/2014 | Siewerdsen et al. |
| 2014/0058406 A1 | 2/2014 | Tsekos |
| 2014/0073914 A1 | 3/2014 | Avallee et al. |
| 2014/0080086 A1 | 3/2014 | Chen |
| 2014/0081128 A1 | 3/2014 | Verard et al. |
| 2014/0088612 A1 | 3/2014 | Bartol et al. |
| 2014/0094694 A1 | 4/2014 | Moctezuma de la Barrera |
| 2014/0094851 A1 | 4/2014 | Gordon |
| 2014/0096369 A1 | 4/2014 | Matsumoto et al. |
| 2014/0100587 A1 | 4/2014 | Farritor et al. |
| 2014/0121676 A1 | 5/2014 | Kostrzewski et al. |
| 2014/0128882 A1 | 5/2014 | Kwak et al. |
| 2014/0135796 A1 | 5/2014 | Simon et al. |
| 2014/0142591 A1 | 5/2014 | Alvarez et al. |
| 2014/0142592 A1 | 5/2014 | Moon et al. |
| 2014/0148692 A1 | 5/2014 | Hartmann et al. |
| 2014/0163581 A1 | 6/2014 | Devengenzo et al. |
| 2014/0171781 A1 | 6/2014 | Stiles |
| 2014/0171900 A1 | 6/2014 | Stiles |
| 2014/0171965 A1 | 6/2014 | Loh et al. |
| 2014/0180308 A1 | 6/2014 | von Grunberg |
| 2014/0180309 A1 | 6/2014 | Seeber et al. |
| 2014/0187915 A1 | 7/2014 | Yaroshenko et al. |
| 2014/0188132 A1 | 7/2014 | Kang |
| 2014/0194699 A1 | 7/2014 | Roh et al. |
| 2014/0130810 A1 | 8/2014 | Azizian et al. |
| 2014/0221819 A1 | 8/2014 | Sarment |
| 2014/0222023 A1 | 8/2014 | Kim et al. |
| 2014/0228631 A1 | 8/2014 | Kwak et al. |
| 2014/0234804 A1 | 8/2014 | Huang et al. |
| 2014/0257328 A1 | 9/2014 | Kim et al. |
| 2014/0257329 A1 | 9/2014 | Jang et al. |
| 2014/0257330 A1 | 9/2014 | Choi et al. |
| 2014/0275760 A1 | 9/2014 | Lee et al. |
| 2014/0275985 A1 | 9/2014 | Walker et al. |
| 2014/0276931 A1 | 9/2014 | Parihar et al. |
| 2014/0276940 A1 | 9/2014 | Seo |
| 2014/0276944 A1 | 9/2014 | Farritor et al. |
| 2014/0288413 A1 | 9/2014 | Hwang et al. |
| 2014/0299648 A1 | 10/2014 | Shelton, IV et al. |
| 2014/0303434 A1 | 10/2014 | Farritor et al. |
| 2014/0303643 A1 | 10/2014 | Ha et al. |
| 2014/0305995 A1 | 10/2014 | Shelton, IV et al. |
| 2014/0309659 A1 | 10/2014 | Roh et al. |
| 2014/0316436 A1 | 10/2014 | Bar et al. |
| 2014/0323803 A1 | 10/2014 | Hoffman et al. |
| 2014/0324070 A1 | 10/2014 | Min et al. |
| 2014/0330288 A1 | 11/2014 | Date et al. |
| 2014/0364720 A1 | 12/2014 | Darrow et al. |
| 2014/0371577 A1 | 12/2014 | Maillet et al. |
| 2015/0039034 A1 | 2/2015 | Frankel et al. |
| 2015/0085970 A1 | 3/2015 | Bouhnik et al. |
| 2015/0146847 A1 | 5/2015 | Liu |
| 2015/0150524 A1 | 6/2015 | Yorkston et al. |
| 2015/0196261 A1 | 7/2015 | Funk |
| 2015/0213633 A1 | 7/2015 | Chang et al. |
| 2015/0335480 A1 | 11/2015 | Alvarez et al. |
| 2015/0342647 A1 | 12/2015 | Frankel et al. |
| 2016/0005194 A1 | 1/2016 | Schretter et al. |
| 2016/0166329 A1 | 6/2016 | Langan et al. |
| 2016/0235480 A1 | 8/2016 | Scholl et al. |
| 2016/0249990 A1 | 9/2016 | Glozman et al. |
| 2016/0302871 A1 | 10/2016 | Gregerson et al. |
| 2016/0320322 A1 | 11/2016 | Suzuki |
| 2016/0331335 A1 | 11/2016 | Gregerson et al. |
| 2017/0135770 A1 | 5/2017 | Scholl et al. |
| 2017/0143284 A1 | 5/2017 | Sehnert et al. |
| 2017/0143426 A1 | 5/2017 | Isaacs et al. |
| 2017/0156816 A1 | 6/2017 | Ibrahim |
| 2017/0202629 A1 | 7/2017 | Maillet et al. |
| 2017/0212723 A1 | 7/2017 | Atarot et al. |
| 2017/0215825 A1 | 8/2017 | Johnson et al. |
| 2017/0215826 A1 | 8/2017 | Johnson et al. |
| 2017/0215827 A1 | 8/2017 | Johnson et al. |
| 2017/0231710 A1 | 8/2017 | Scholl et al. |
| 2017/0258426 A1 | 9/2017 | Risher-Kelly et al. |
| 2017/0273748 A1 | 9/2017 | Hourtash et al. |
| 2017/0296277 A1 | 10/2017 | Hourtash et al. |
| 2017/0360493 A1 | 12/2017 | Zucher et al. |
| 2019/0029561 A1 | 1/2019 | Kim et al. |
| 2020/0246088 A1 | 8/2020 | Mewes et al. |
| 2020/0297426 A1* | 9/2020 | Cameron ............... A61B 90/37 |

(56) References Cited

U.S. PATENT DOCUMENTS

2021/0085264 A1* 3/2021 Cleary ................ A61B 6/4441
2021/0361357 A1  11/2021 Crawford
2022/0007991 A1   1/2022 Roberts et al.

FOREIGN PATENT DOCUMENTS

JP      2018-079304 A    5/2018
JP      2020-163130 A   10/2020

* cited by examiner

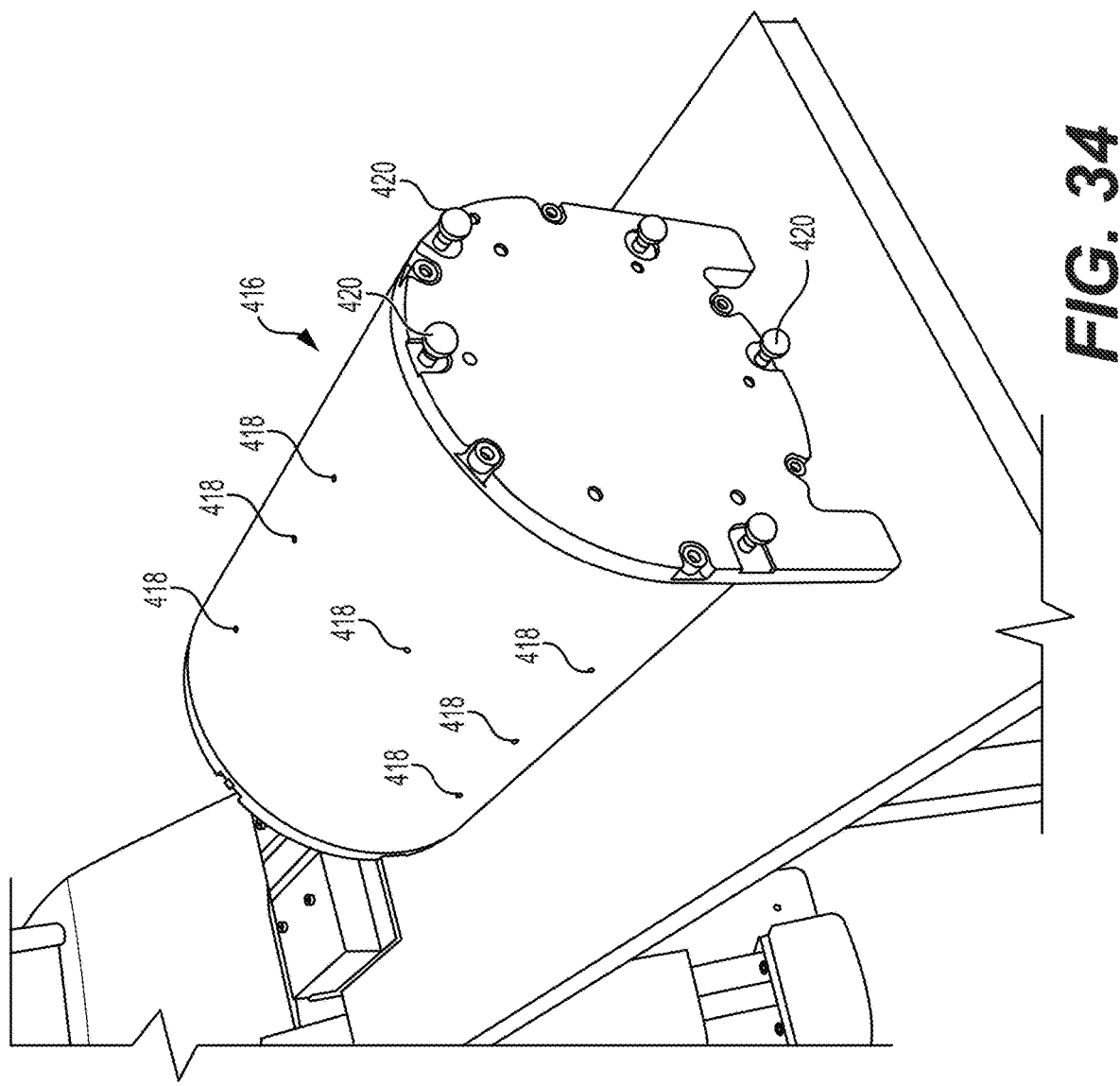

REGISTRATION OF 3D AND 2D IMAGES FOR SURGICAL NAVIGATION AND ROBOTIC GUIDANCE WITHOUT USING RADIOPAQUE FIDUCIALS IN THE IMAGES

CROSS-REFERENCE TO RELATED APPLICATIONS

The present application is a continuation of U.S. patent application Ser. No. 18/184,192, filed Mar. 15, 2023, which claims priority to U.S. provisional patent application No. 63/389,691, filed Jul. 15, 2022, all of which are incorporated herein by reference.

The present application is also related to, but does not claim priority to (1) patent application Ser. No. 15/180,126, filed Jun. 13, 2016 (U.S. Pat. No. 10,842,453), and (2) patent application Ser. No. 15/157,444, filed May 18, 2016 (U.S. Pub. No. 2016/0256225), all of which are incorporated herein by reference.

TECHNICAL FIELD

The present invention relates to navigation systems, and more particularly, to a system and method of registering a medical image of a patient in an imaging space to the patient in a physical space.

BACKGROUND OF THE DISCLOSURE

Surgical navigation has revolutionized minimally invasive spine surgery by allowing surgeons to accurately and repeatably place implant hardware with decreased radiation and operative time as opposed to conventional surgical techniques. In surgical navigation, a position sensor is used to track full rigid body motion of surgical instruments with respect to a medical image registered to a patient reference frame. The most common form of position sensing is optical tracking, specifically near infrared (NIR) passive retroreflective markers or active NIR LEDs arranged in a pattern called an array. The position of the tracked instruments is typically displayed to the surgeon user as a CAD model of the instrument overlaid on the medical image.

Robotic guidance is a technology where a robotic arm is positioned on the desired trajectory and used to guide the instruments on an accurate and repeatable trajectory. With the launch of ExcelsiusGPS ("eGPS") from Globus Medical, Inc. of Audubon, PA, robotic guidance has been integrated with surgical navigation in a single system called robotic navigation. Robotic navigation offers the benefits of both technologies in a single streamlined system.

All surgical navigation, robotic guidance, and robotic navigation systems require registration of a medical image to the patient's anatomy through the use of system's reference frame. Registration of optical navigation systems typically involve the use of a registration fixture, which contains an array of tracking markers positioned in known locations with respect to an array of embedded radiopaque fiducials. The fixture is attached to the patient and surrounding structures such as the imaging system such that the fiducials are embedded in the medical image and tracking markers are visible to the position sensor (e.g., stereoscopic camera of a tracking device). After the images are captured, a software algorithm then uses computer vision and image processing to identify the radiopaque fiducial locations in the image. Since the locations of the fiducials with respect to the tracking markers on the fixture are known, and the camera is able to identify the position of tracking markers in the fixture array relative to the patient reference array (also known as dynamic reference array or DRB), the system can then compute multiple transformations to register the medical image to the tracking system.

There are several disadvantages to using registration fixtures intraoperatively. The primary drawback is a requirement that the image volume be captured with radiopaque fiducials already in place on the patient, meaning that scans of a patient taken preoperatively cannot be used for navigation. An additional drawback is the loss of usable image space due to inclusion of the fixture fiducials within the image volume/area. In addition, the fiducials can sometimes obstruct the view of critical anatomy. When capturing images with registration fixtures, special care must be taken to ensure that the necessary number of fiducials are included and are visible with sufficient contrast to the background. Finally, registration fixtures are additional hardware components that must be stored, cleaned, draped/sterilized, and installed intraoperatively, leading to increased time and complexity for the surgical staff.

In response, some companies (e.g., Medtronic O-arm and SteathStation) have developed methods of obtaining registered intraoperative images without the need for a registration fixture (automatic registration). To accomplish this, these systems have integrated or detachable tracking arrays at known locations of the imaging system. An associated navigation system can then be used to track the position of the imaging system navigation array relative to the patient reference array to complete the image registration.

However, existing solutions are limited in their flexibility to adapt to surgical navigation and robotic workflows in a streamlined system. Usage of an intraoperative scanner to register tracking to the medical image volume requires the patient to be irradiated again and a new image captured. A solution is still needed to be able to use existing medical image volumes taken without fiducials present.

Moreover, the primary failure mode of navigated surgery is loss of registration due to shift of patient anatomy relative to the patient reference array. If registration is lost during a surgical procedure, the surgical team needs to return the 3D imaging system to the surgical site and capture new registered images. The need for this additional 3D image exposes the patient to significant additional radiation, increases time under anesthesia, and decreases efficiency for the hospital.

Therefore, it would be desirable to provide a system and method for registering a medical image to the patient's anatomy without the use of any embedded radiopaque fiducials. Moreover, when registration is lost during surgery, it would be desirable to provide a system and method for quickly recovering registration without using another full 3D scan of the patient.

SUMMARY OF THE DISCLOSURE

According to one aspect of the present invention, a system and method of registering a pre-op 3D medical image of a patient in an imaging space to the patient in a tracked space is disclosed. The method receives a 3D image of a patient anatomy which was taken with an imaging device pre-operatively. At this point, the 3D image has not been registered with the patient lying on an operating table. Once the patient has been prepared and is lying on an operating table, an imaging device is rolled in and an intra-op 2D image of the patient anatomy is captured by the imaging device having imaging tracking markers trackable by a tracking device (e.g., optical or electromagnetic tracking system).

The system receives a corresponding optical image of the patient from the tracking device at the time of image capture, the optical image containing the imaging tracking markers and a dynamic reference base (DRB) including patient tracking markers trackable by the tracking device.

The 2D image is then matched to a corresponding 2D simulated medical image, which is a synthetically generated medical image at a selected orientation and position, which has been digitally reconstructed from the pre-op 3D image. In the case of an x-ray medical imaging device, the simulated image is a DRR (digitally reconstructed radiograph) of the pre-op 3D image. In the embodiment shown, the DRR is a simulated 2D fluoroscopic image at a selected orientation and angle, which has been digitally reconstructed from the pre-op 3D image (e.g., a set/stack of 2D slices of the 3D image volume). In the case of an ultrasound, it would be a synthetically generated 2D image representing an ultrasound scan at a particular orientation and position from the pre-op 3D image.

The system then determines a registration of the pose of the received pre-op 3D image relative to the dynamic reference base based on the matched DRR, and the patient tracking markers and the imaging tracking markers contained in the received optical image. Registration is achieved because the pose of the matched DRR corresponds to the tracked pose of the actual 2D image.

The method then displays the registered 3D images and any selected 2D DRR of the 3D image on a display along with tracked surgical instruments, its planned trajectory and end effector superimposed on top of the displayed 3D image for visual navigation assistance.

Advantageously, the registration method requires no radiopaque fiducials to be present in the medical images, and there is no need to attach any registration fixture to the imaging device as was previously necessary. As a result, the present method may substantially reduce procedure time and increase patient safety.

According to another aspect of the present invention, a system and method of registering an intra-op 3D image (such as a 3D CT or MRI image) of a patient in an imaging space to the physical patient in a tracked physical space without embedding fiducials (e.g., radiopaque markers) in images is disclosed. The system receives an intra-op image of a patient anatomy which has been captured by an imaging device having imaging tracking markers trackable by a tracking device, the patient having a dynamic reference base including patient tracking markers trackable by the tracking device. The system also receives an optical image of the patient from the tracking device at the time of image capture, the optical image containing the patient tracking markers and the imaging tracking markers.

The method then determines transforms A, B and C. Transform A representing the pose of the imaging device relative to the dynamic reference base is determined based on the received optical image. Transform B representing the pose of the received image of the patient anatomy relative to the imaging device is determined based on the received optical image. Transform C representing the pose of the received image relative to the dynamic reference base is determined by multiplying transform A and transform B. Transform C represents the registration of the patient image in the imaging space to the physical patient in a physical space, all of the transforms being performed without the use of any fiducials.

The method then displays the registered images on a display along with tracked surgical instruments, its planned trajectory and end effector superimposed on top of the displayed 3D image for visual navigation assistance.

Advantageously, as the registration method requires no radiopaque fiducials in the medical images, the present method may substantially reduce procedure time and increase patient safety. Also because no pre-op scan of the patient is necessary, it may save cost and may eliminate any unnecessary radiation exposure to the patient.

According to another aspect of the present invention, a system and method for recovering registration of a 3D image of a patient in an imaging space to the physical patient in a physical space is provided. The system receives a 3D image of a patient anatomy and registers a pose of the received 3D image relative to a dynamic reference base containing patient tracking markers. The registered 3D image is then used during the surgical procedure.

Upon loss of registration, however, registration is re-established without performing another full 3D scan of the patient. The system receives two or more intra-op 2D images (e.g., fluoroscopic or ultrasound) of the patient anatomy at different orientations that have been captured by an imaging device having imaging tracking markers trackable by a tracking device (e.g., optical or electromagnetic). The system also receives corresponding optical images of the patient from the tracking device at the time of image capture, the optical images containing the patient tracking markers and the imaging tracking markers.

The received 2D images are matched to corresponding simulated 2D images (e.g., DRR) of the 3D image. Registration of the 3D image is re-established based on the matched corresponding DRRs, and the patient tracking markers and the imaging tracking markers contained in the optical images.

The method then displays the registered 3D image on a display along with tracked surgical instruments, its planned trajectory and end effector superimposed on top of the displayed 3D image for visual navigation assistance.

Advantageously, as the registration is recovered with only a few 2D images without doing another full 3D scan of the patient, the present method may substantially reduce procedure time and increase patient safety.

According to another aspect of the present invention, a system and method of registering intra-op 2D medical images of a patient in an imaging space to the physical patient in a physical space is provided. The system receives intra-op 2D images of the patient anatomy at different orientations which have been captured by an imaging device having imaging tracking markers trackable by a tracking device; the patient having a dynamic reference base including patient tracking markers trackable by the tracking device. The system also receives corresponding optical images of the patient from the tracking device at the time of image capture, the optical images containing the patient tracking markers and the imaging tracking markers.

For each received 2D image, the method then determines transforms A, B and C as described above. Transform C represents the registration of the patient image in the imaging space to the physical patient in a physical space, all of the transforms being performed without the use of any radiopaque fiducials.

The method then displays the registered 2D images on a display along with tracked surgical instruments, its planned trajectory and end effector superimposed on top of the displayed 2D images for visual navigation assistance.

According to another aspect of the present invention, a system and method of registering intra-op 2D images of a patient in an imaging space to the physical patient in a physical space is provided. The system receives intra-op 2D images of the patient anatomy at different orientations which have been captured by an imaging device having imaging tracking markers trackable by a tracking device; the patient having a dynamic reference base including patient tracking markers trackable by the tracking device. The system also receives corresponding optical images of the patient from the tracking device at the time of image capture, the optical images containing the patient tracking markers and the imaging tracking markers.

Based on the received 2D images and generic 3D model, the method creating a customized 3D model. For each received 2D image, the method determines transforms A, B and C as discussed above to register the 2D images. The 2D images are matched to corresponding DRRs of the customized 3D model such that the customized model can be registered based on the matched DRRs.

The method then displays the registered 3D images on a display along with tracked surgical instruments, its planned trajectory and end effector superimposed on top of the displayed 2D images for visual navigation assistance. This method allows navigation with synthetically created 3D model even when access to a 3D scanning imaging device is not available.

DETAILED DESCRIPTION OF THE DISCLOSURE

FIGS. 9A-G illustrate the 360 degree rotation of the gantry in 60 degree increments.

Figure 10:
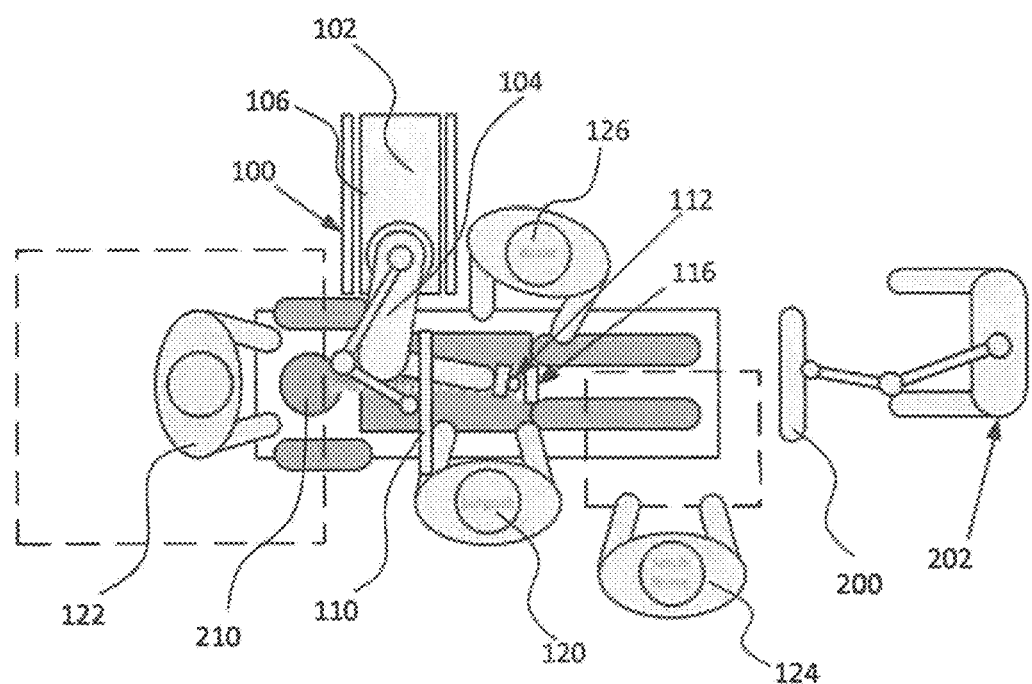
Figure 11:
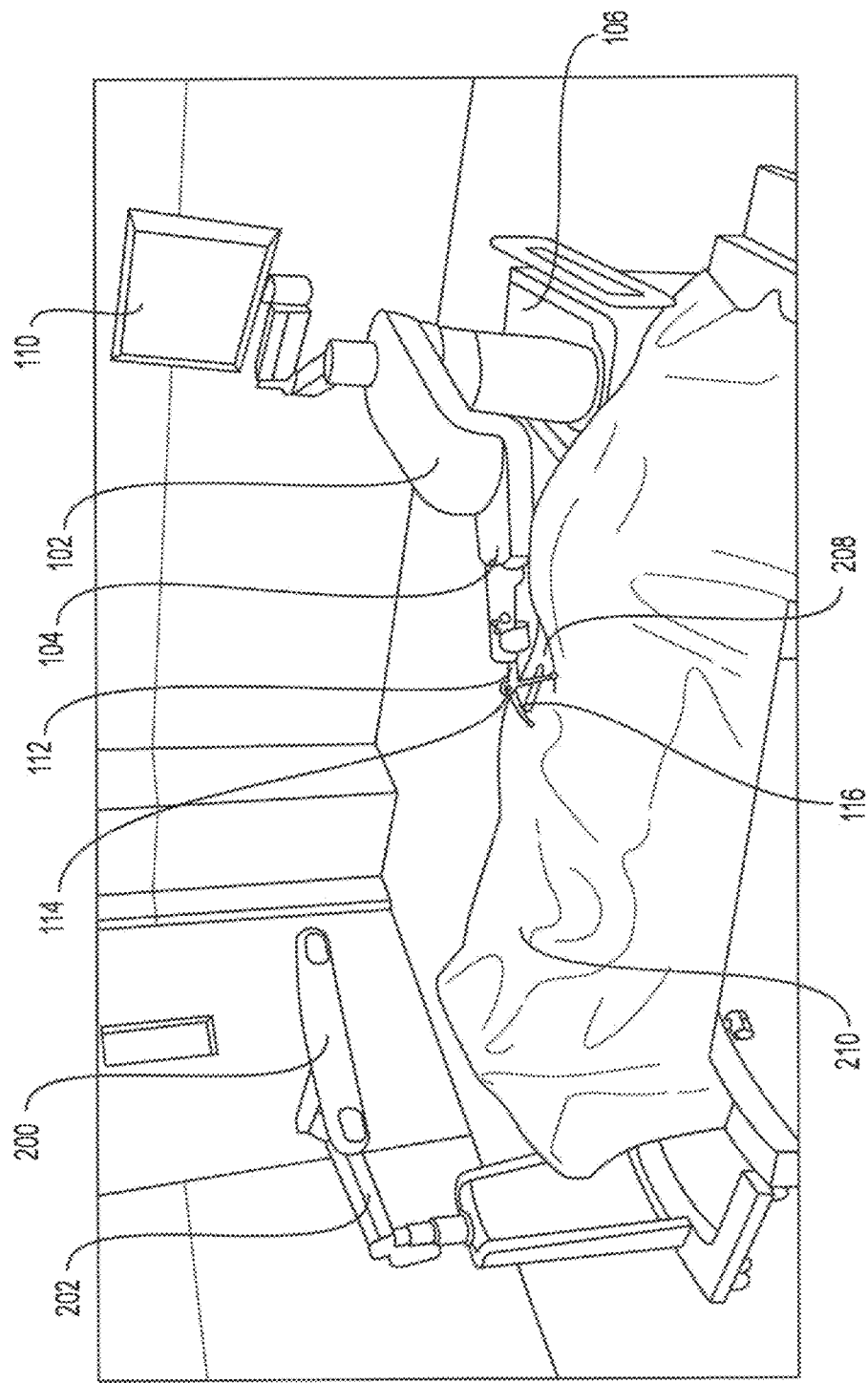
Figure 12:
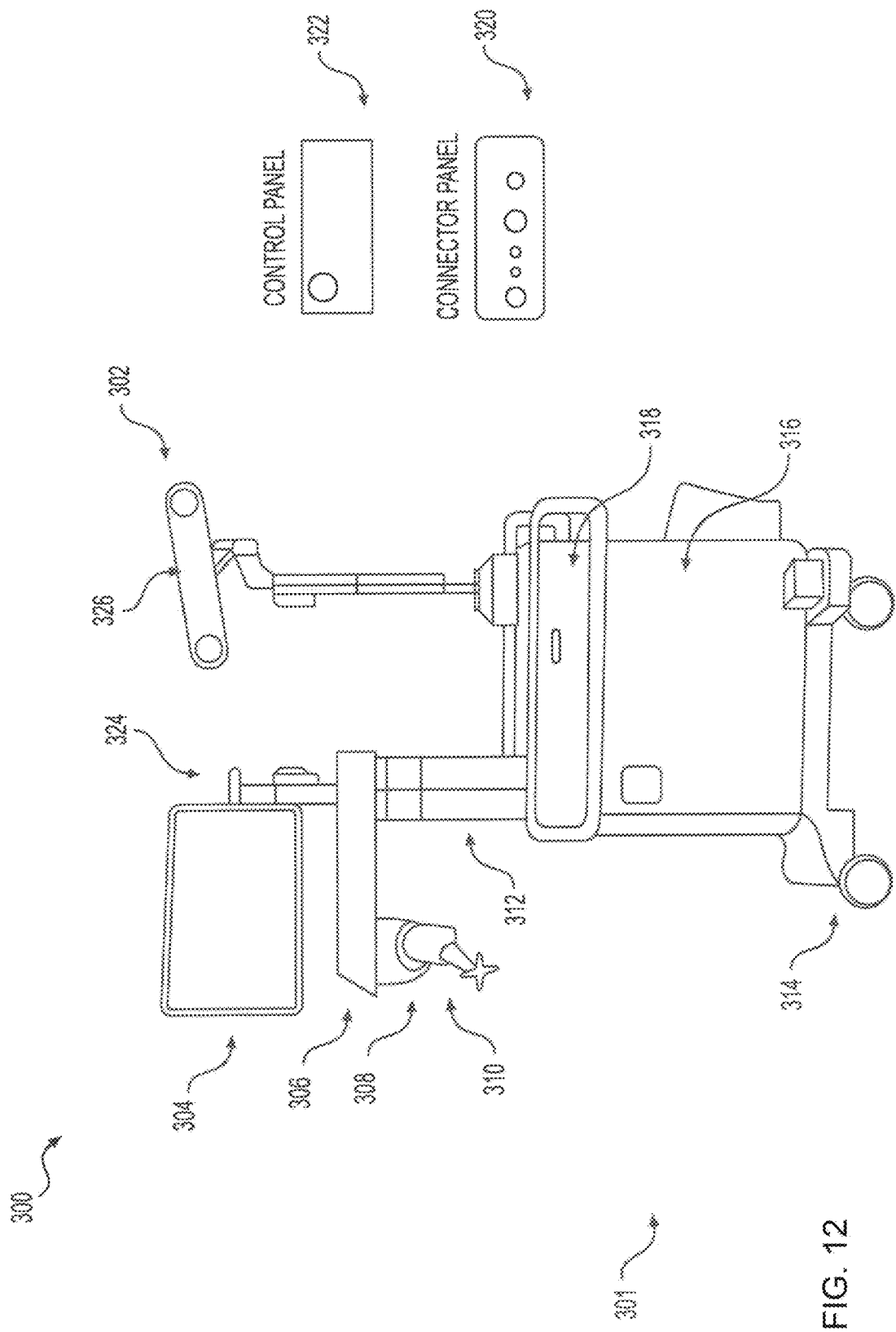

FIG. 10 is an overhead view of a potential arrangement for locations of the robotic system, patient, surgeon, and other medical personnel during a surgical procedure;

FIG. 11 illustrates the robotic system including positioning of the surgical robot and the camera relative to the patient according to one embodiment;

FIG. 12 illustrates a surgical robotic system in accordance with an exemplary embodiment.

Figure 13:
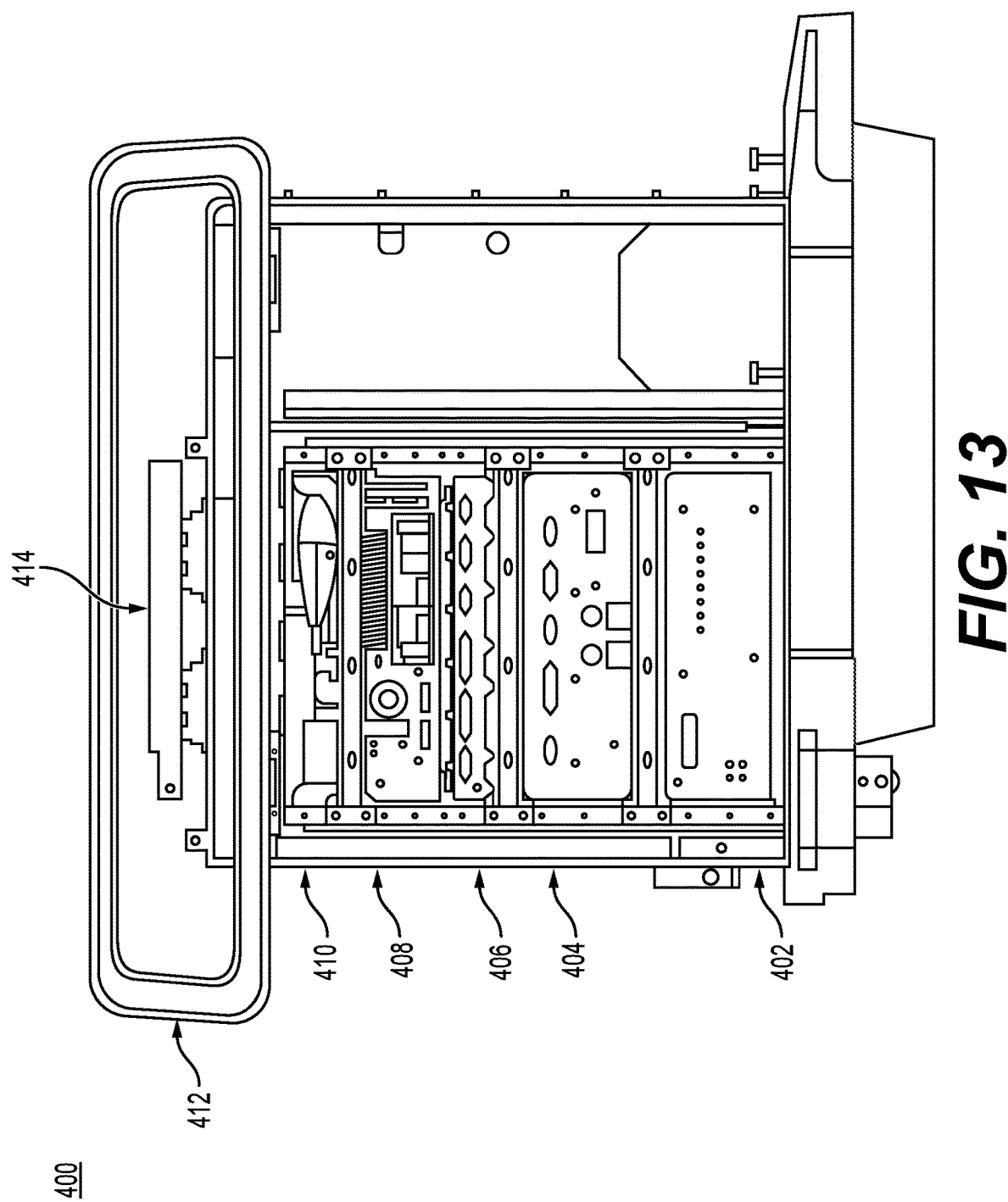
Figure 14:
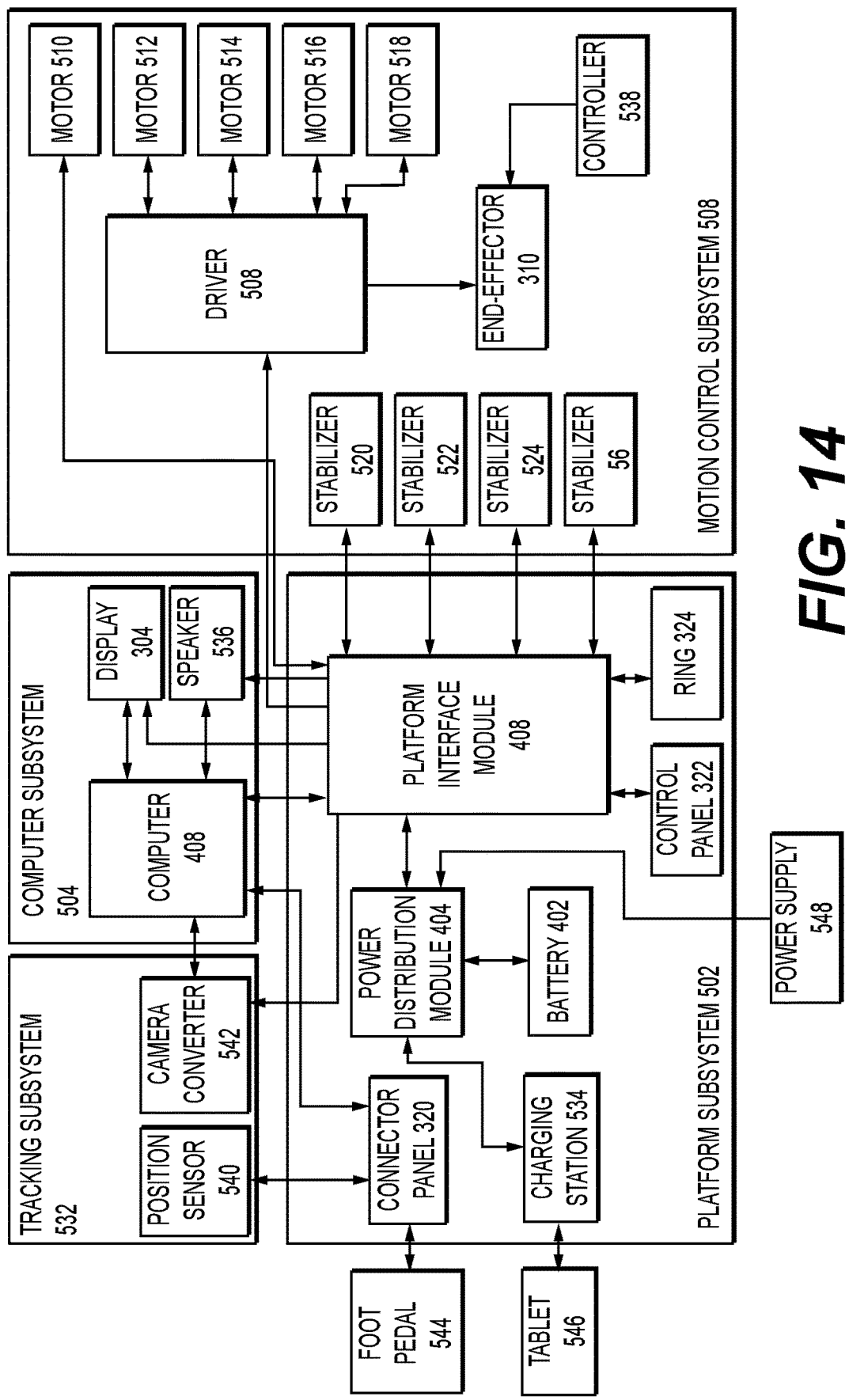
Figure 15:
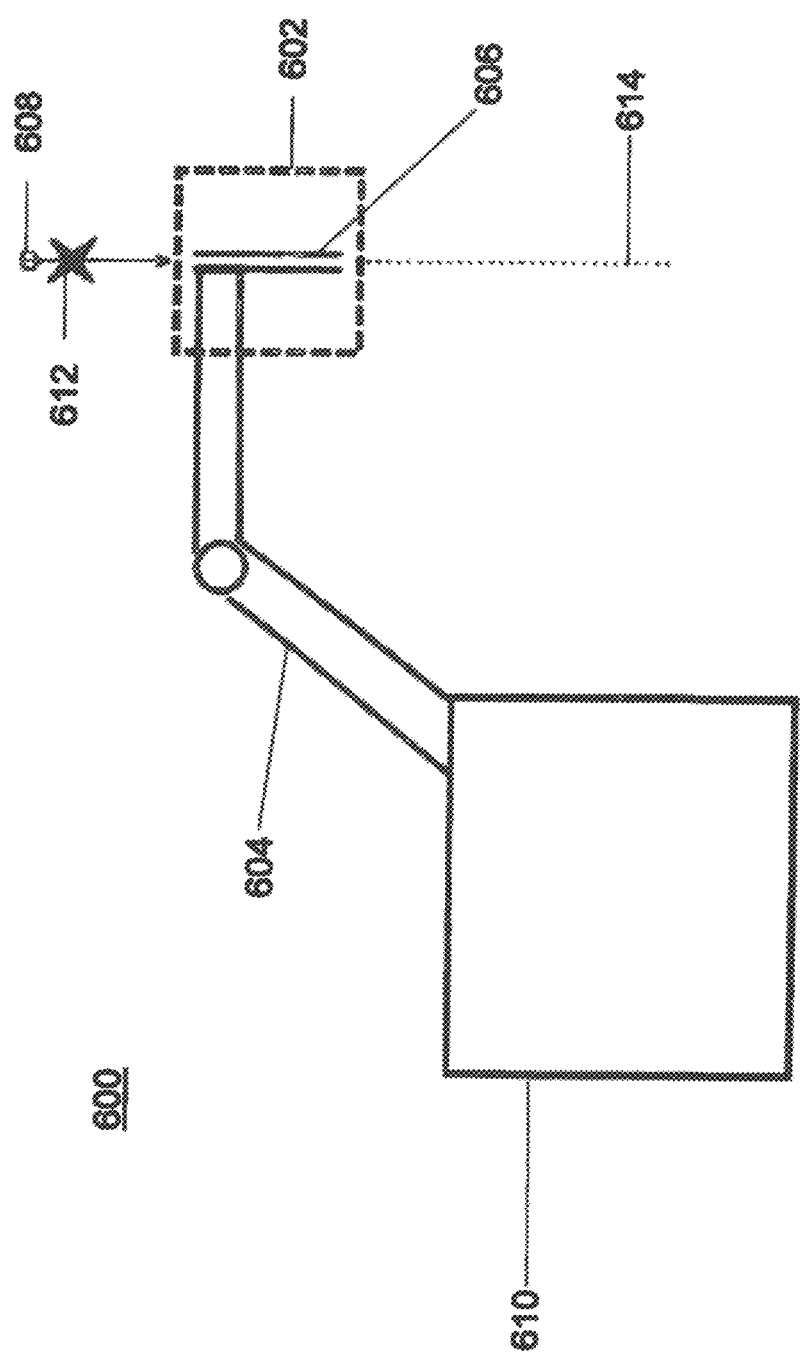
Figure 16C:
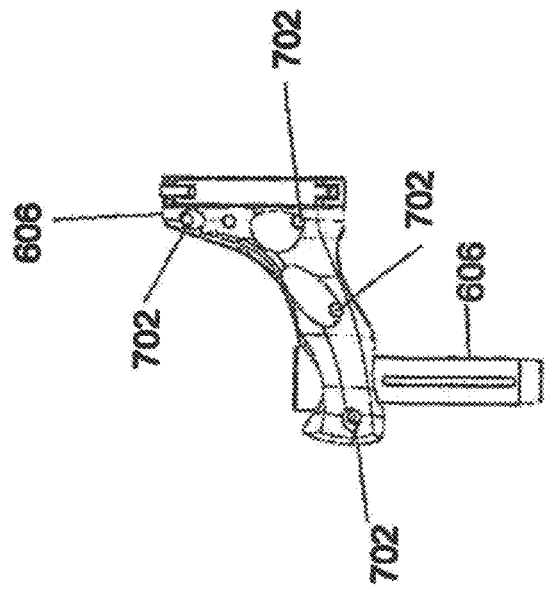
Figure 16A:
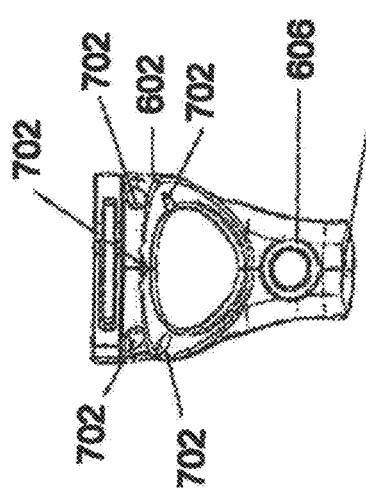
Figure 16B:
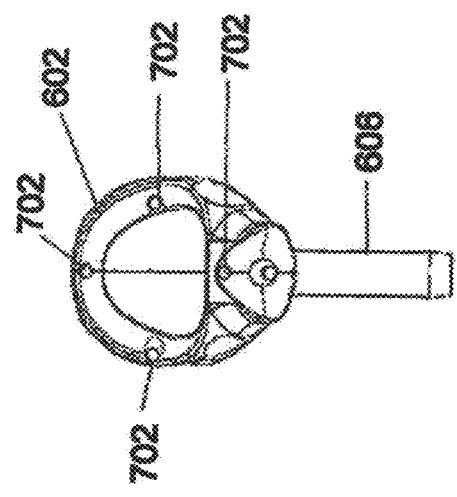
Figure 17:
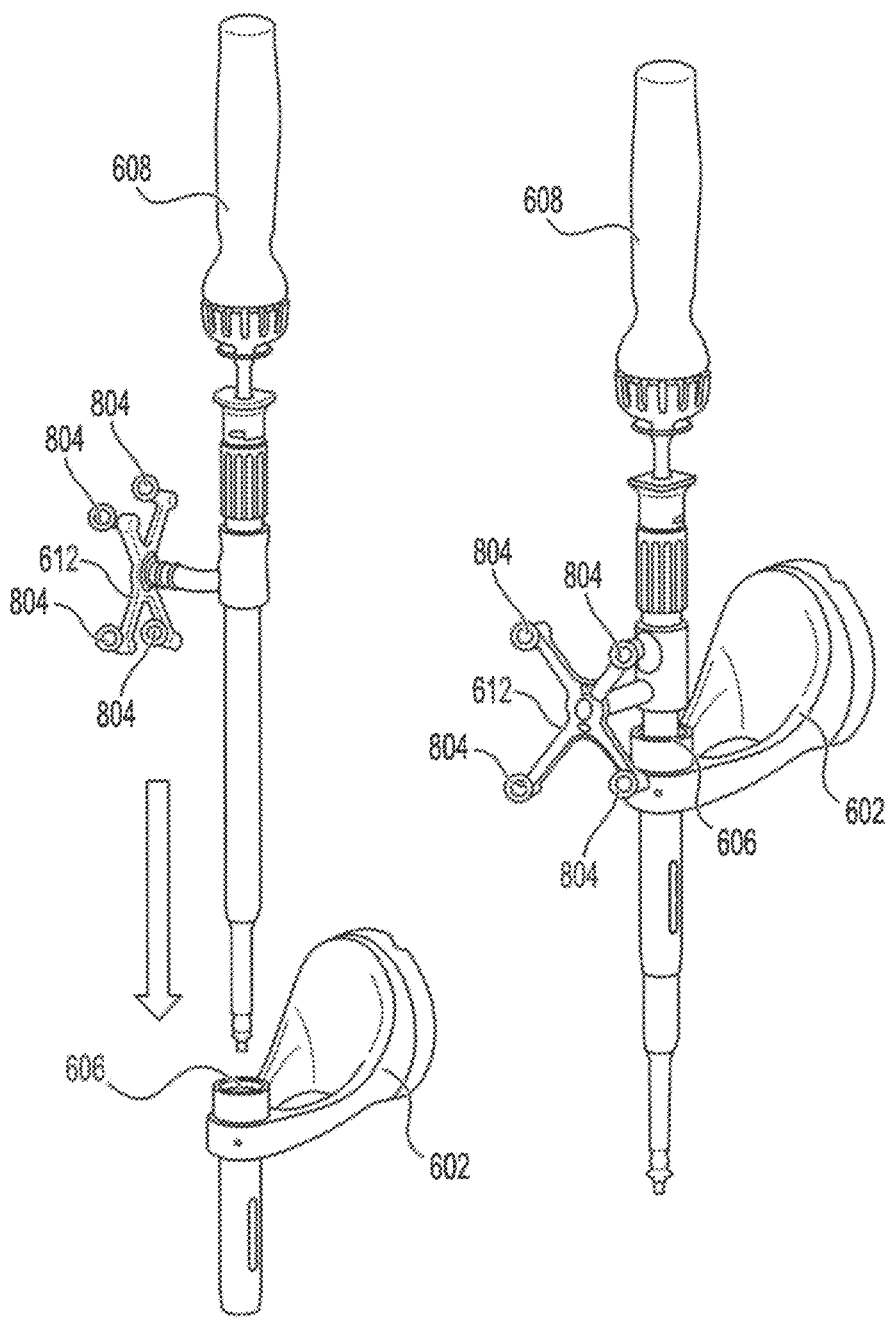
Figures 18A, 18B, 18C:
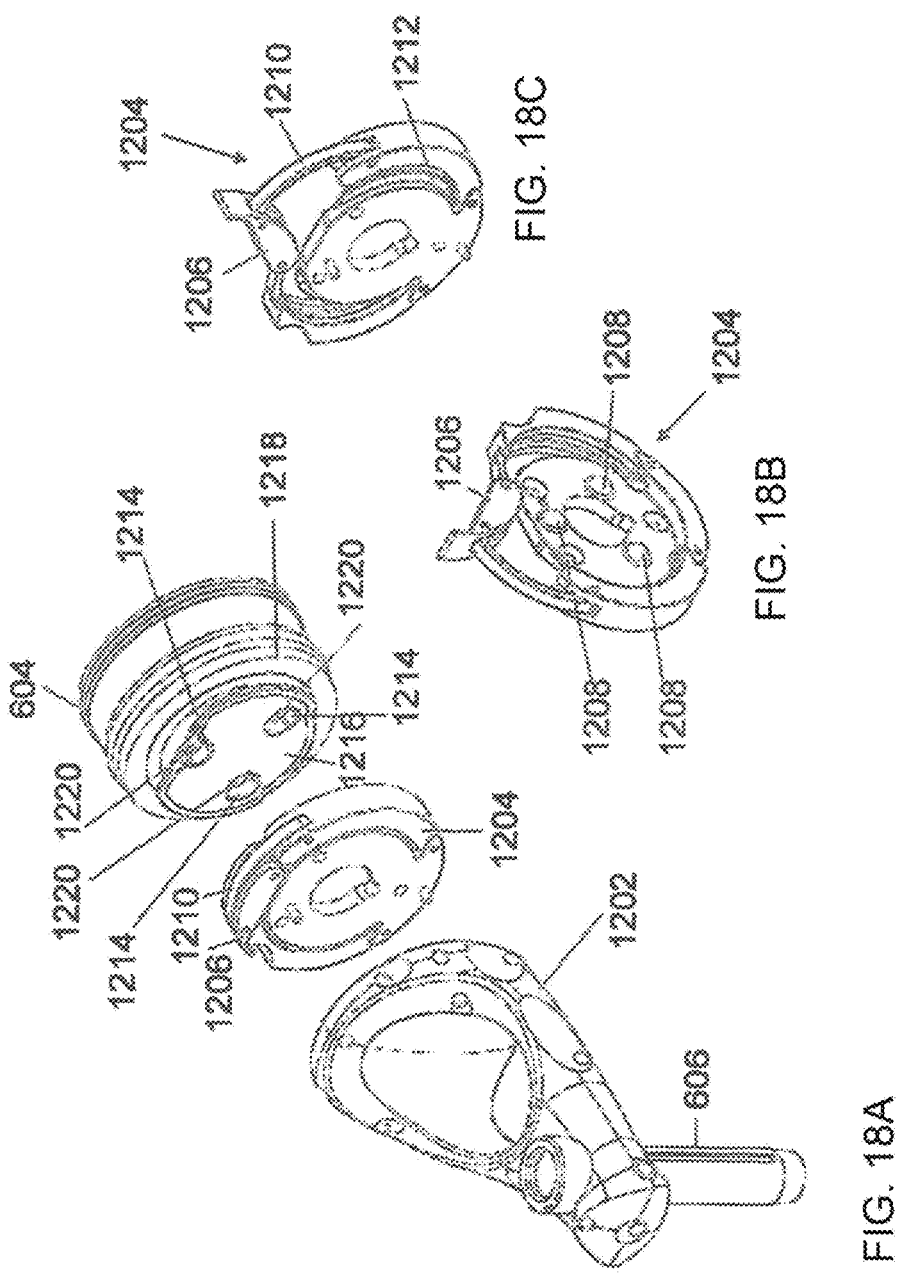
Figure 19:
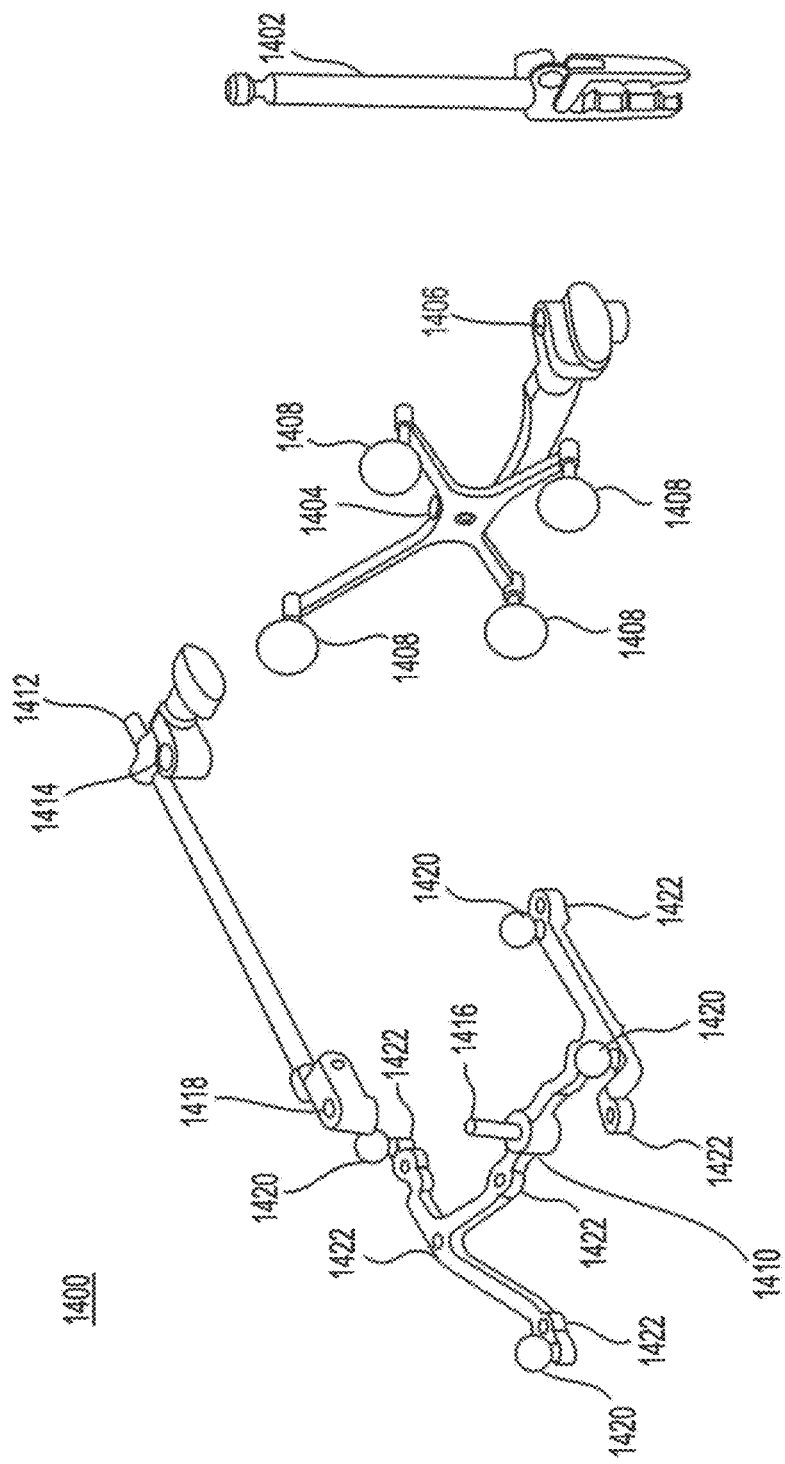
Figure 20:
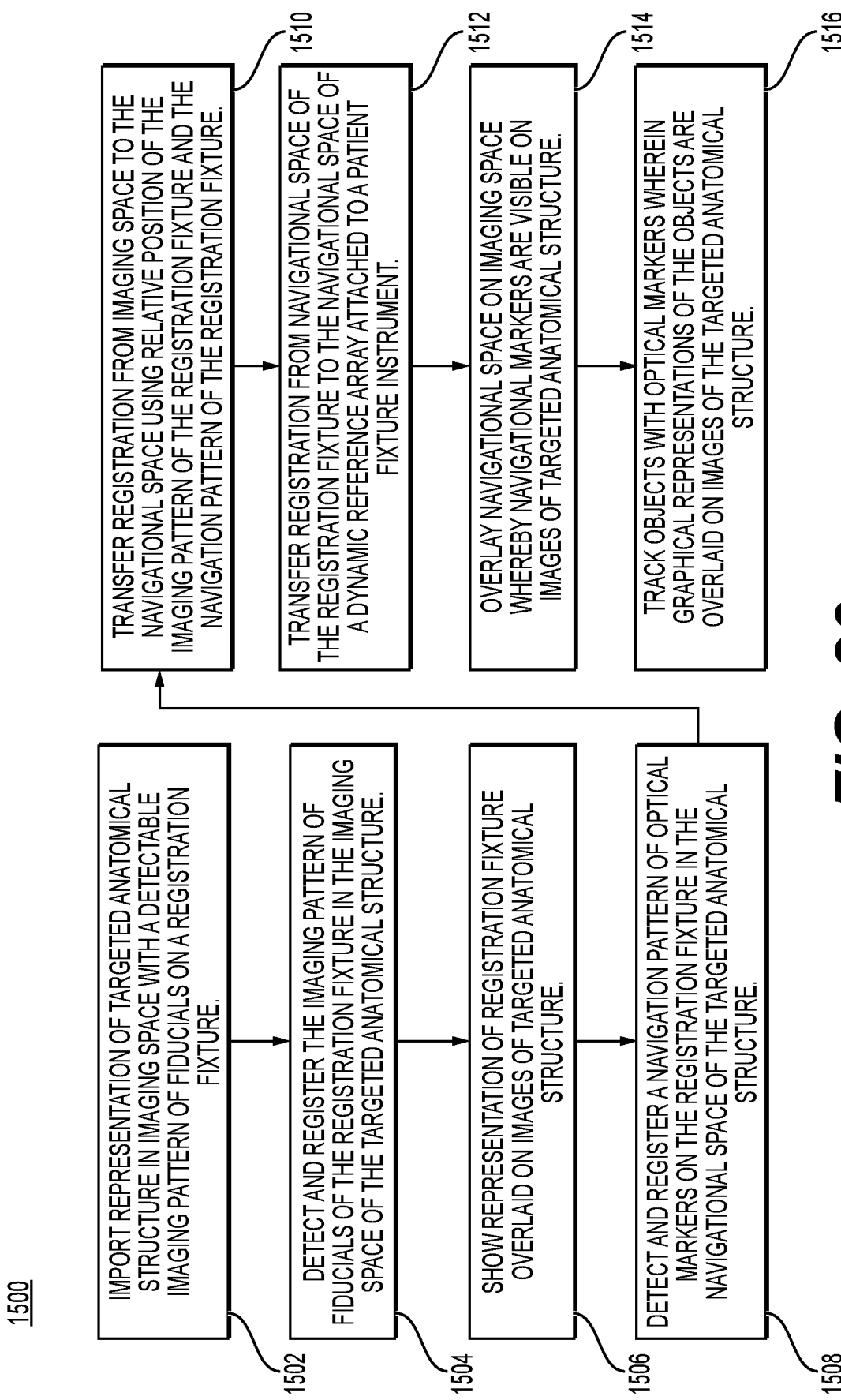
Figure 21A:
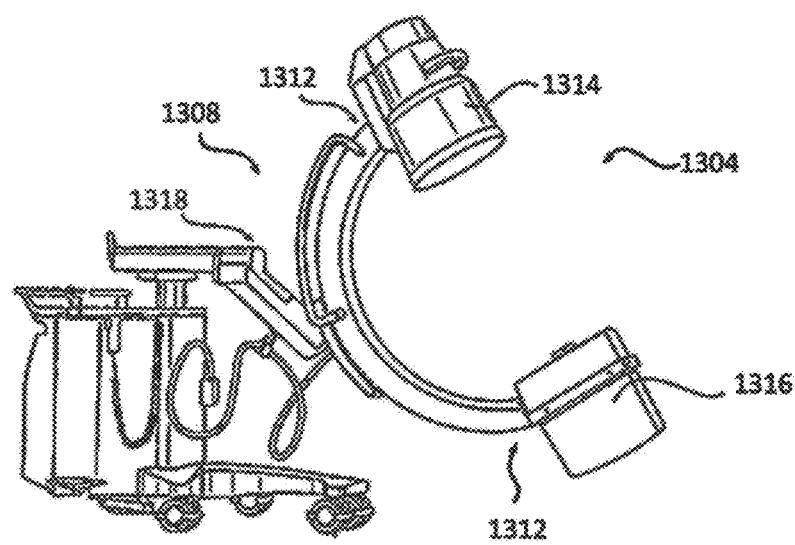
Figure 21B:
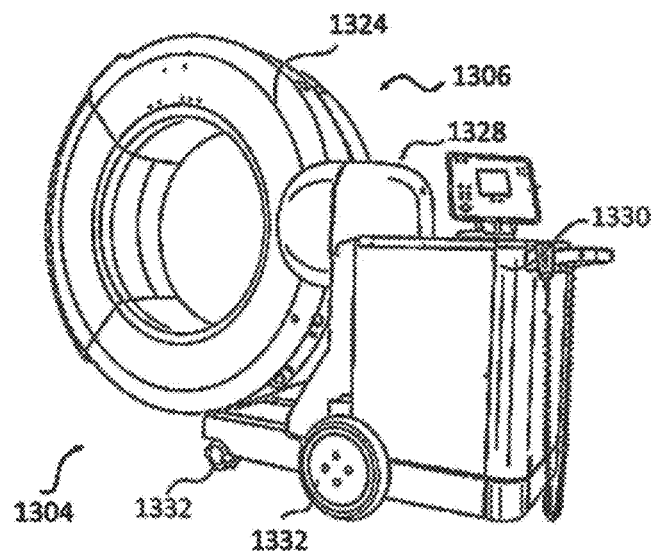
Figure 22A:
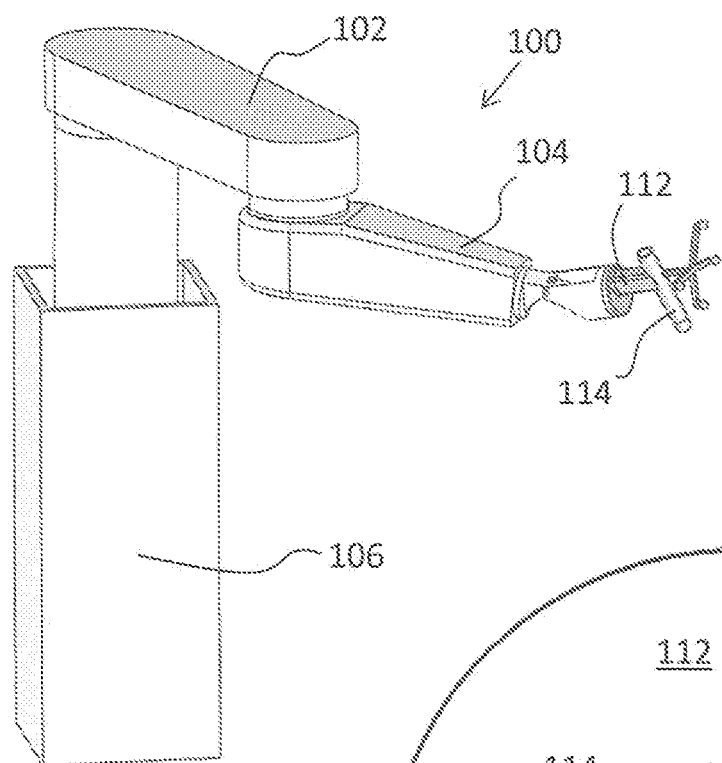
Figure 22B:
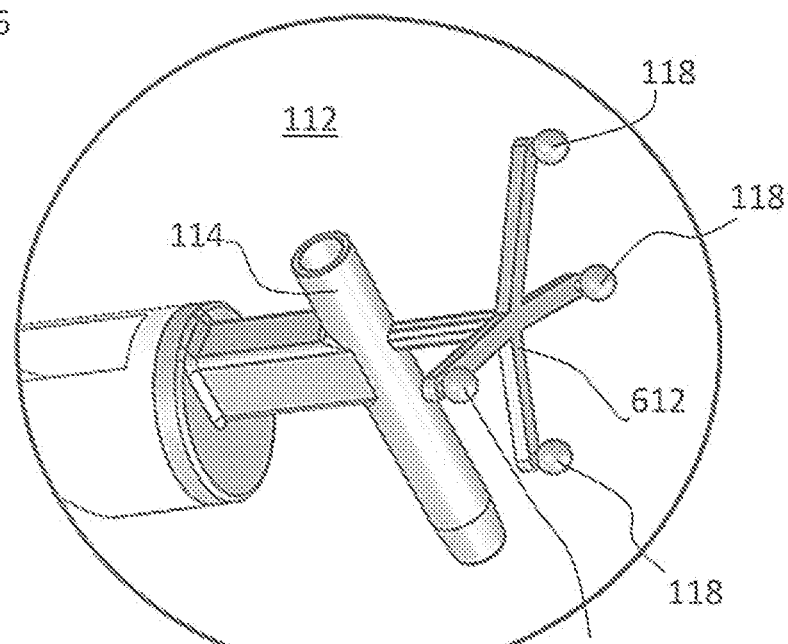
Figure 22C:
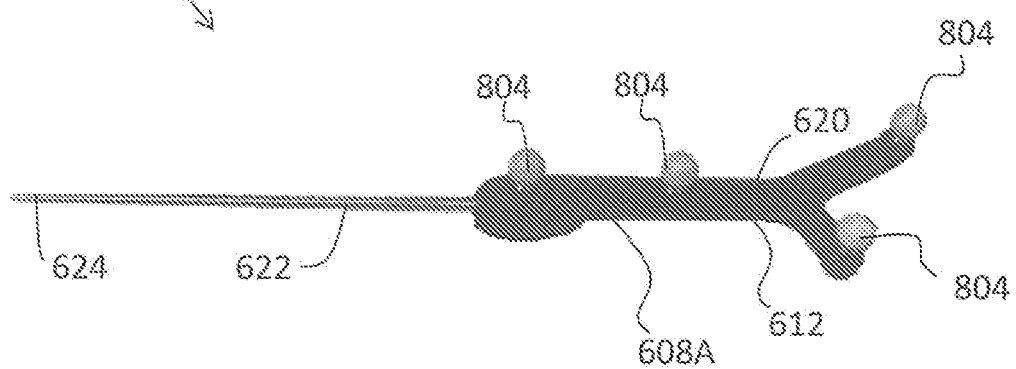
Figures 23A, 23B:
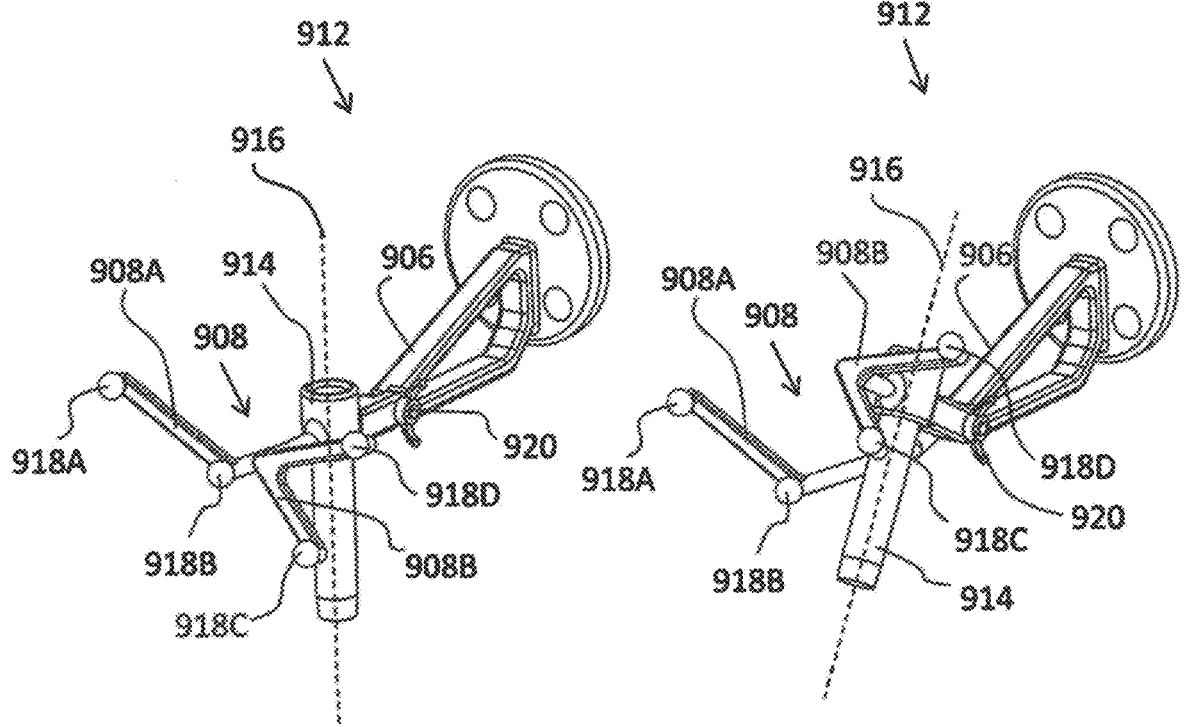
Figures 23C, 23D:
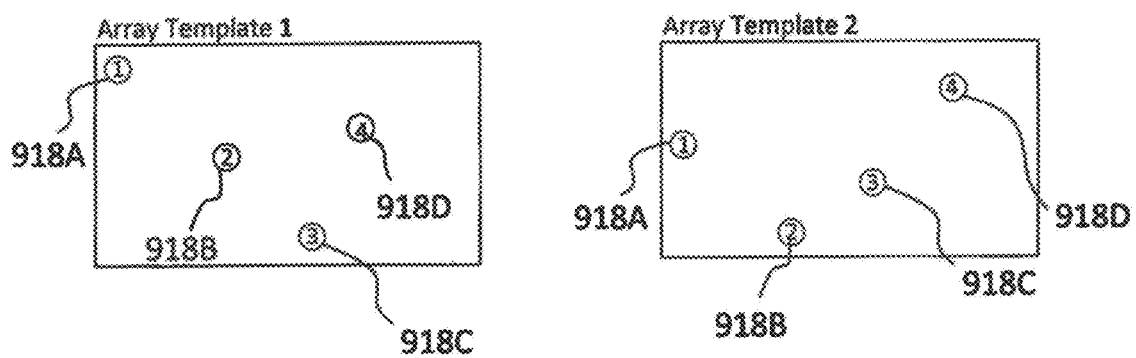
Figure 24A:
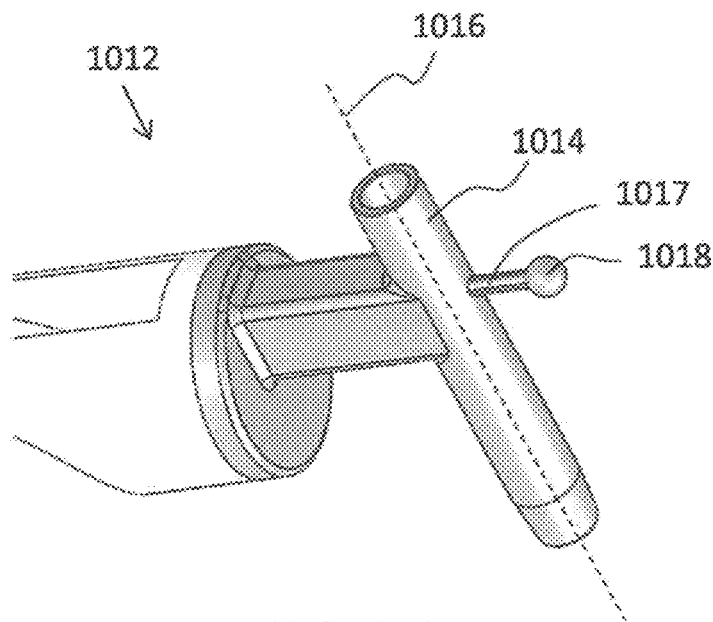
Figure 24B:
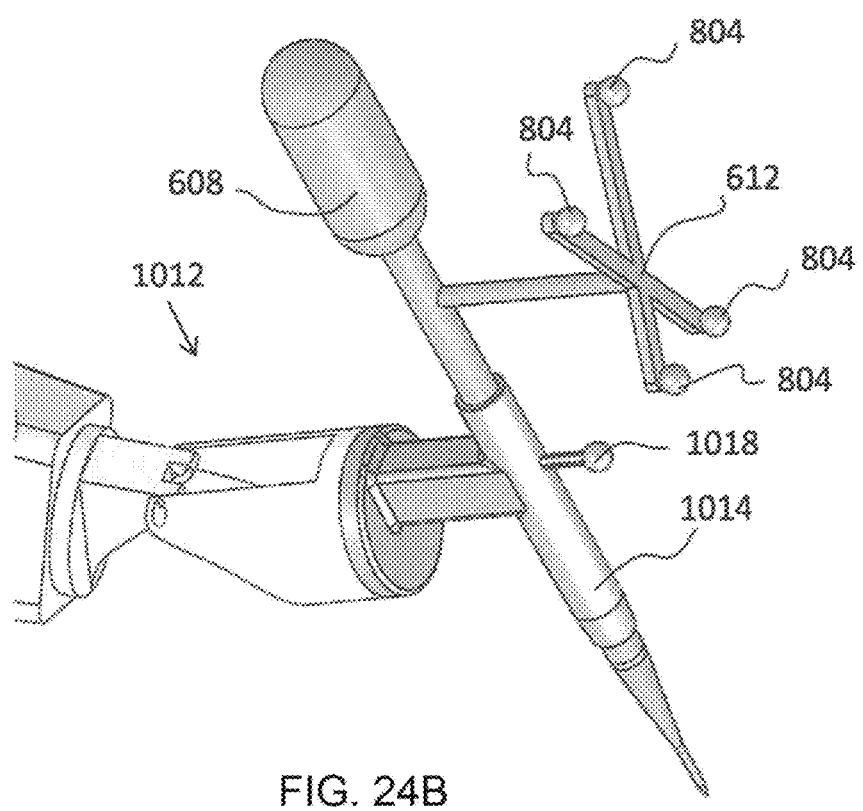
Figure 24C:
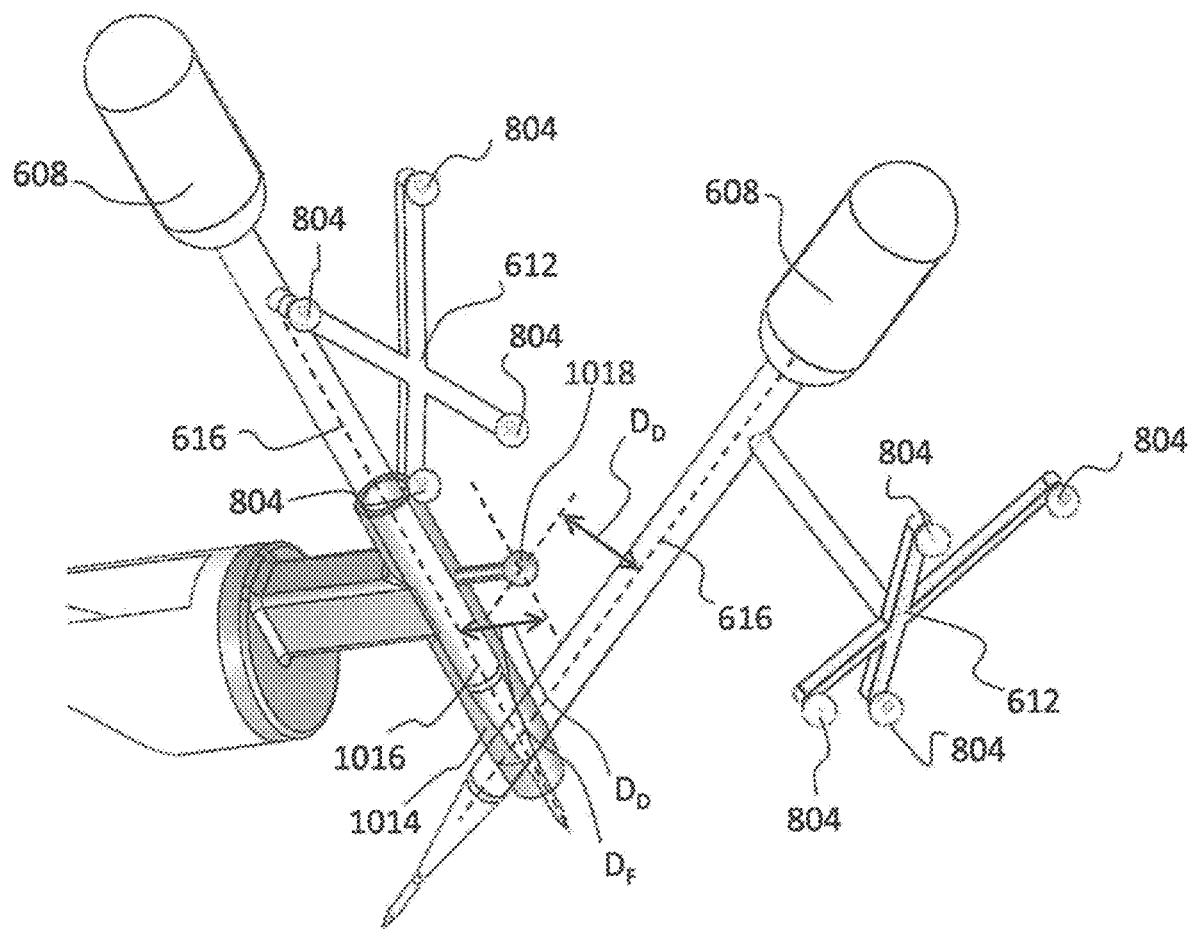
Figure 24D:
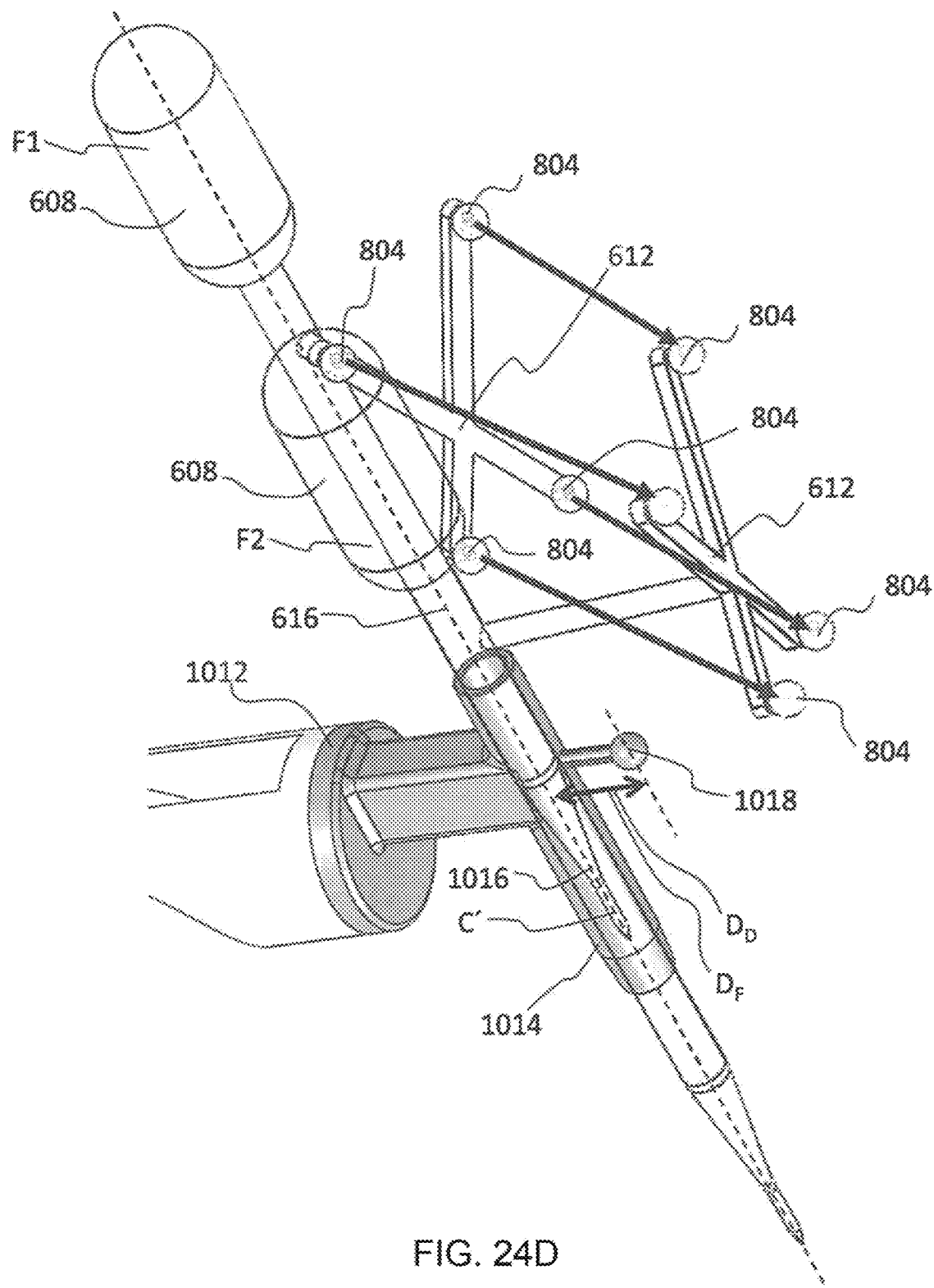
Figure 24E:
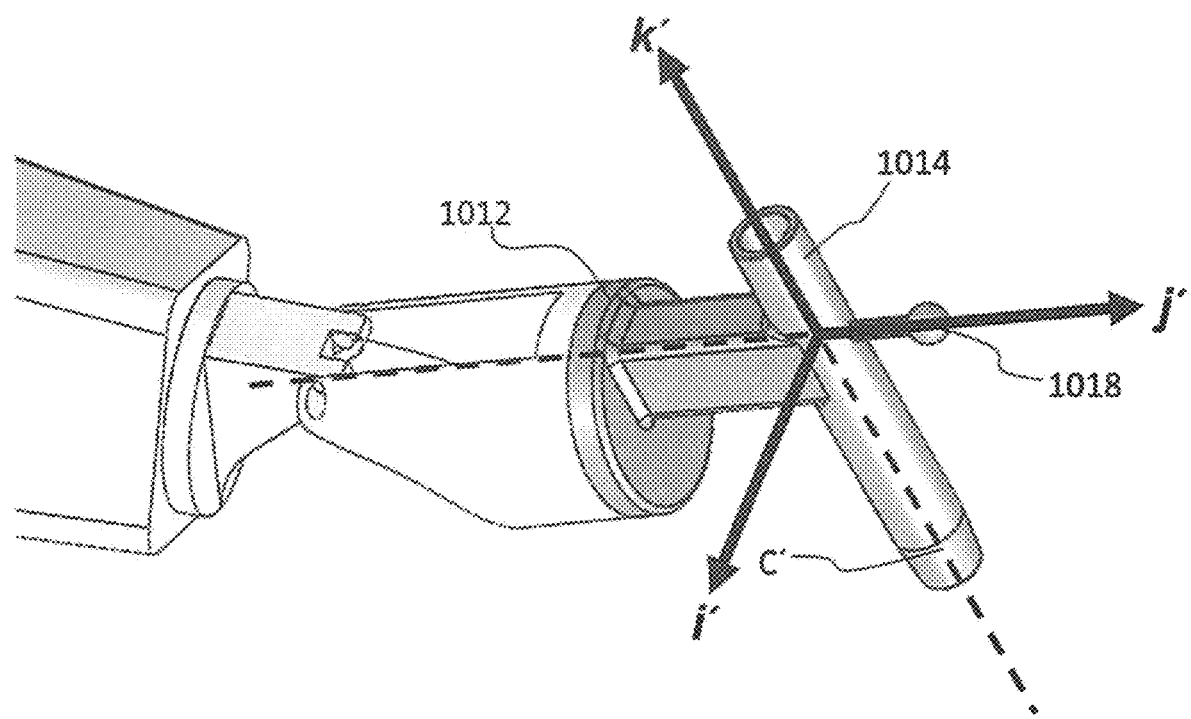
Figure 25:
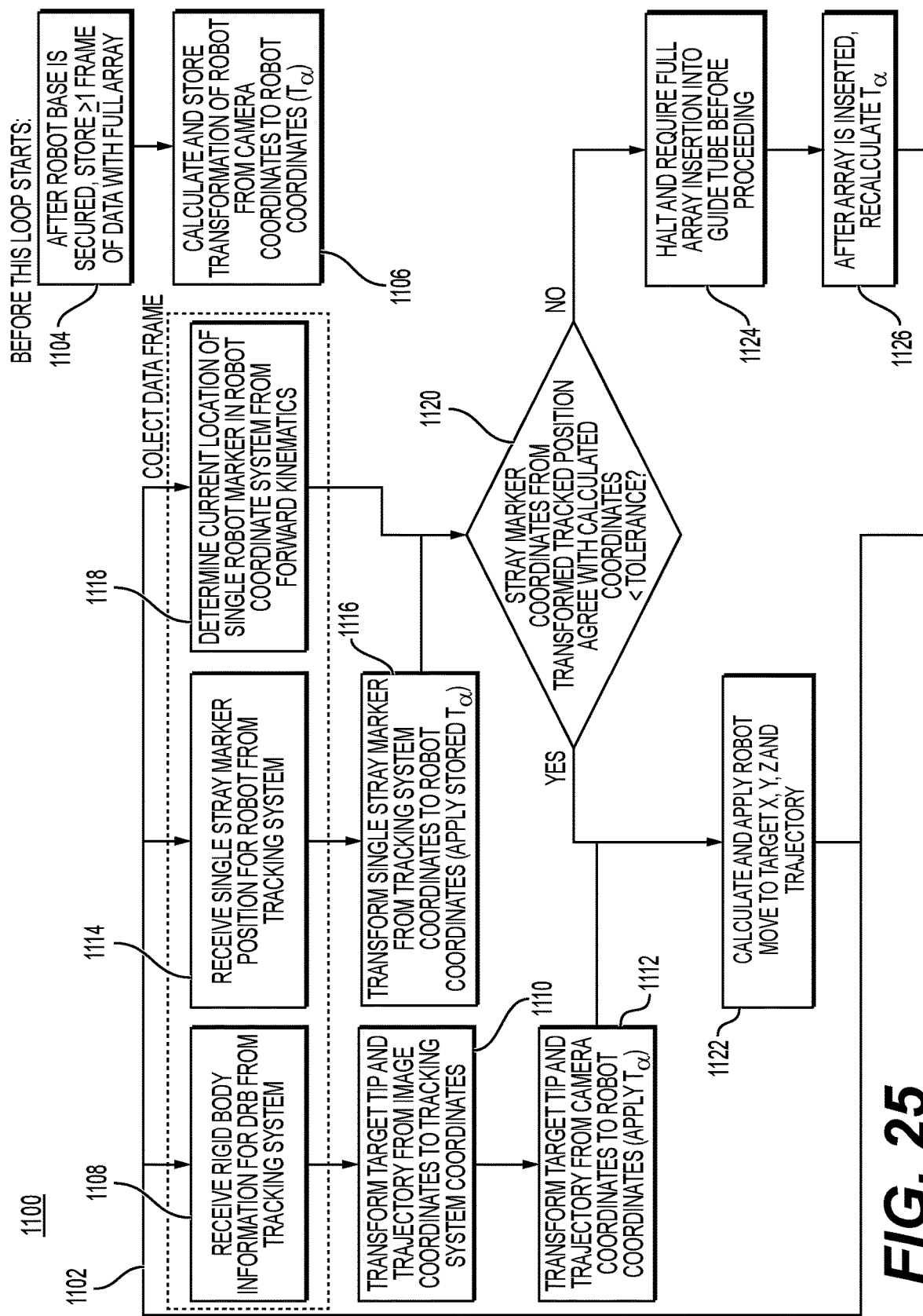
Figure 26A:
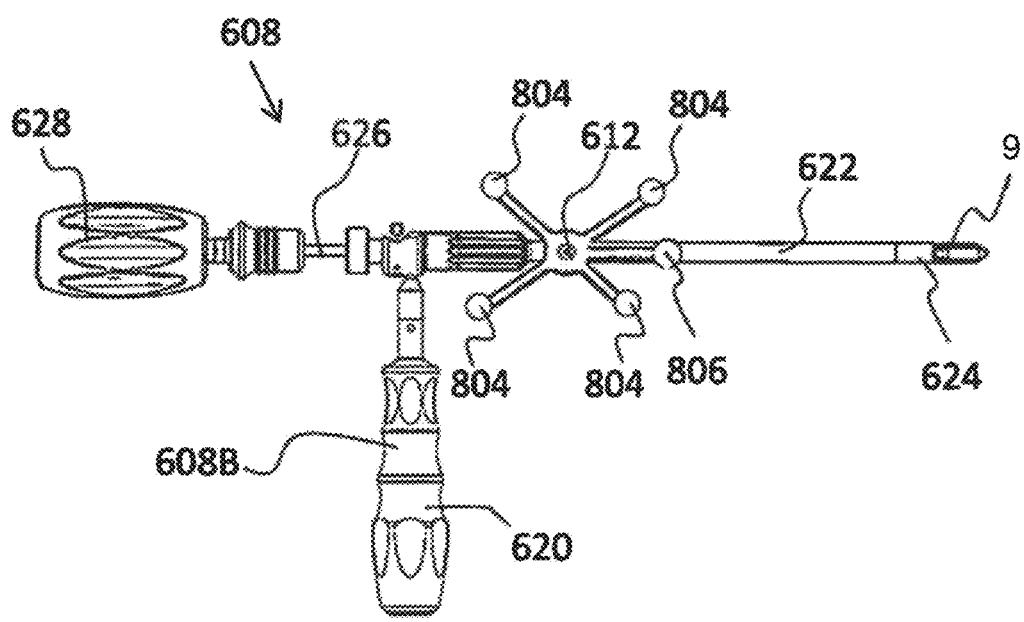
Figure 26B:
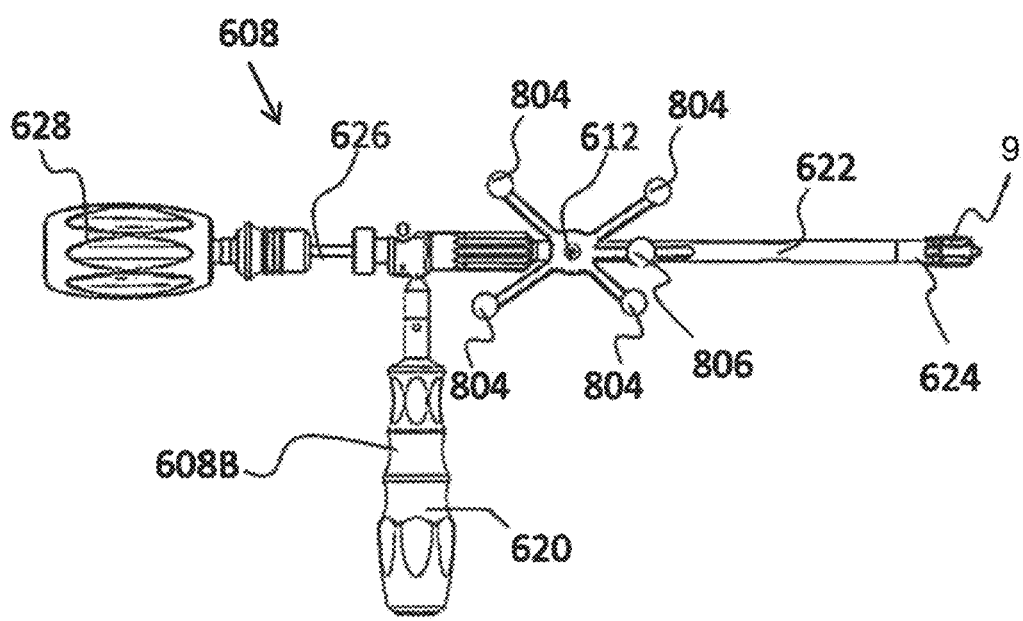
Figure 27A:
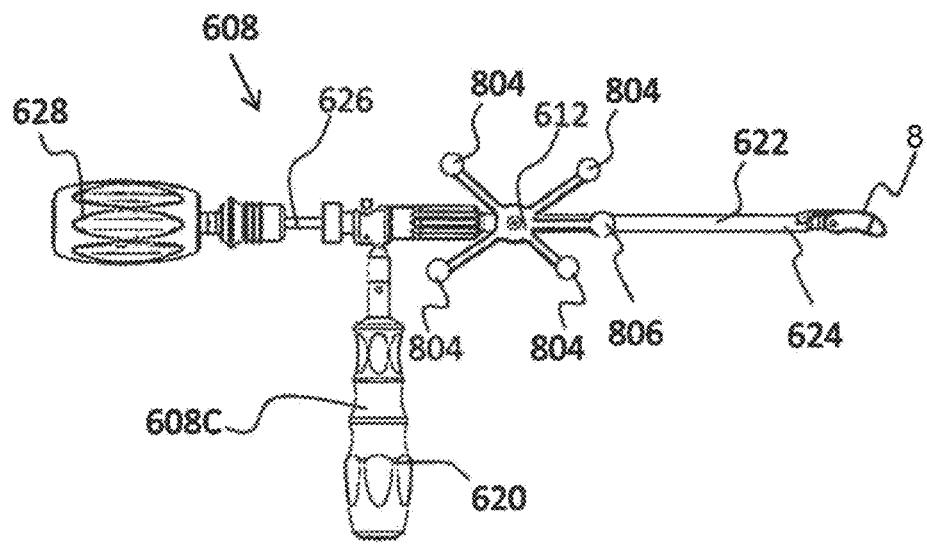
Figure 27B:
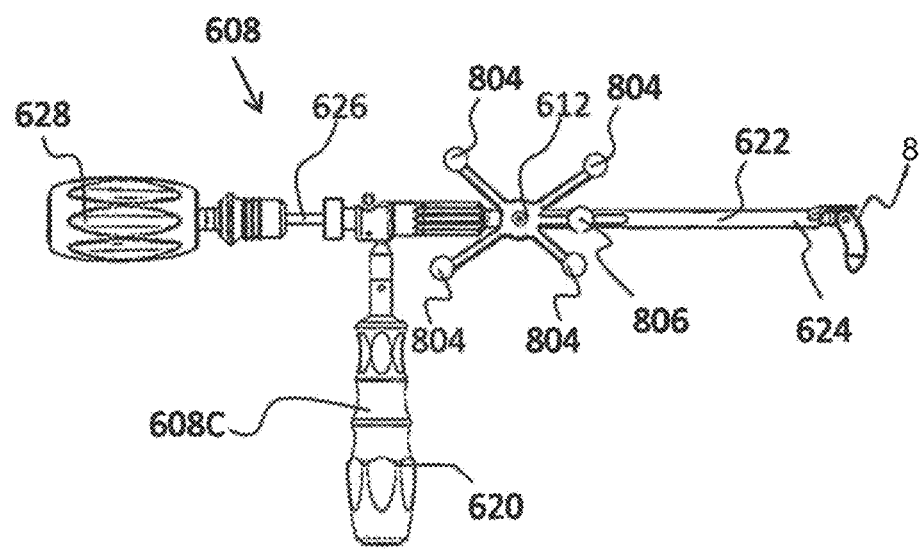

FIG. 13 illustrates a portion of a surgical robot in accordance with an exemplary embodiment;

FIG. 14 illustrates a block diagram of a surgical robot in accordance with an exemplary embodiment;

FIG. 15 illustrates a surgical robot in accordance with an exemplary embodiment;

FIGS. 16A-16C illustrate an end-effector in accordance with an exemplary embodiment;

FIG. 17 illustrates a surgical instrument and the end-effector, before and after, inserting the surgical instrument into the guide tube of the end-effector according to one embodiment;

FIGS. 18A-18C illustrate portions of an end-effector and robot arm in accordance with an exemplary embodiment;

FIG. 19 illustrates a dynamic reference array, an imaging array, and other components in accordance with an exemplary embodiment;

FIG. 20 illustrates a method of registration in accordance with an exemplary embodiment;

FIG. 21A-21B illustrate embodiments of imaging devices according to exemplary embodiments;

FIG. 22A illustrates a portion of a robot including the robot arm and an end-effector in accordance with an exemplary embodiment;

FIG. 22B is a close-up view of the end-effector, with a plurality of tracking markers rigidly affixed thereon, shown in FIG. 22A;

FIG. 22C is a tool or instrument with a plurality of tracking markers rigidly affixed thereon according to one embodiment;

FIG. 23A is an alternative version of an end-effector with moveable tracking markers in a first configuration;

FIG. 23B is the end-effector shown in FIG. 23A with the moveable tracking markers in a second configuration;

FIG. 23C shows the template of tracking markers in the first configuration from FIG. 23A;

FIG. 23D shows the template of tracking markers in the second configuration from FIG. 23B;

FIG. 24A shows an alternative version of the end-effector having only a single tracking marker affixed thereto;

FIG. 24B shows the end-effector of FIG. 24A with an instrument disposed through the guide tube;

FIG. 24C shows the end-effector of FIG. 24A with the instrument in two different positions, and the resulting logic to determine if the instrument is positioned within the guide tube or outside of the guide tube;

FIG. 24D shows the end-effector of FIG. 24A with the instrument in the guide tube at two different frames and its relative distance to the single tracking marker on the guide tube;

FIG. 24E shows the end-effector of FIG. 24A relative to a coordinate system;

FIG. 25 is a block diagram of a method for navigating and moving the end-effector of the robot to a desired target trajectory;

FIGS. 26A-26B depict an instrument for inserting an expandable implant having fixed and moveable tracking markers in contracted and expanded positions, respectively; and FIGS. 27A-27B depict an instrument for inserting an articulating implant having fixed and moveable tracking markers in insertion and angled positions, respectively.

Figure 28:
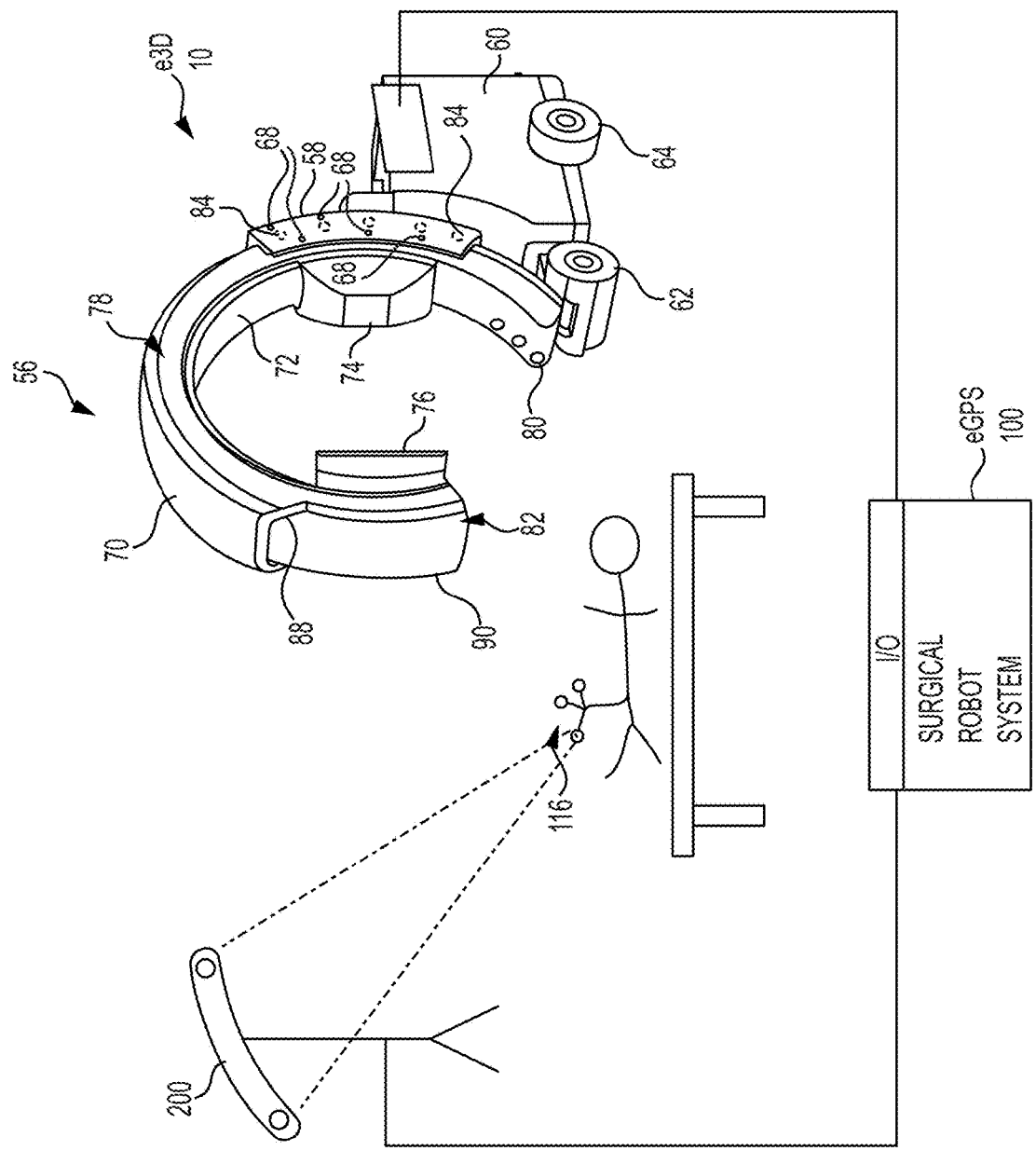

FIG. 28 illustrates a system for registering a patient image in an imaging space to a physical patient in a camera space, preferably without using any embedded radiopaque fiducials in images, according to an aspect of the present invention.

Figure 29:
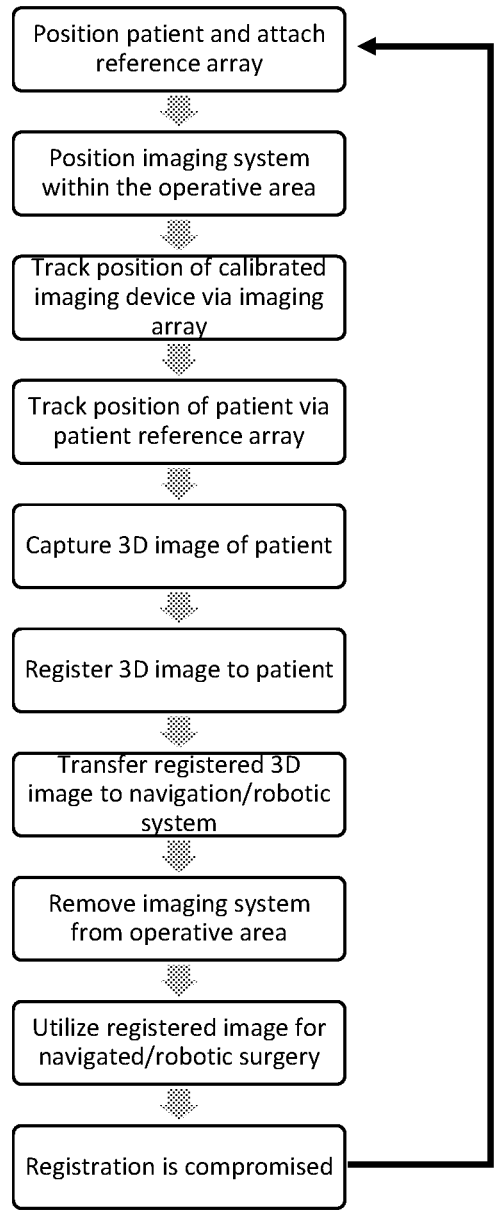

FIG. 29 is a flowchart of a method of registering an intra-op 3D image of a patient in an imaging space to the physical patient in a physical space, preferably without using any embedded radiopaque fiducials in images, according to another aspect of the present invention.

Figure 30:
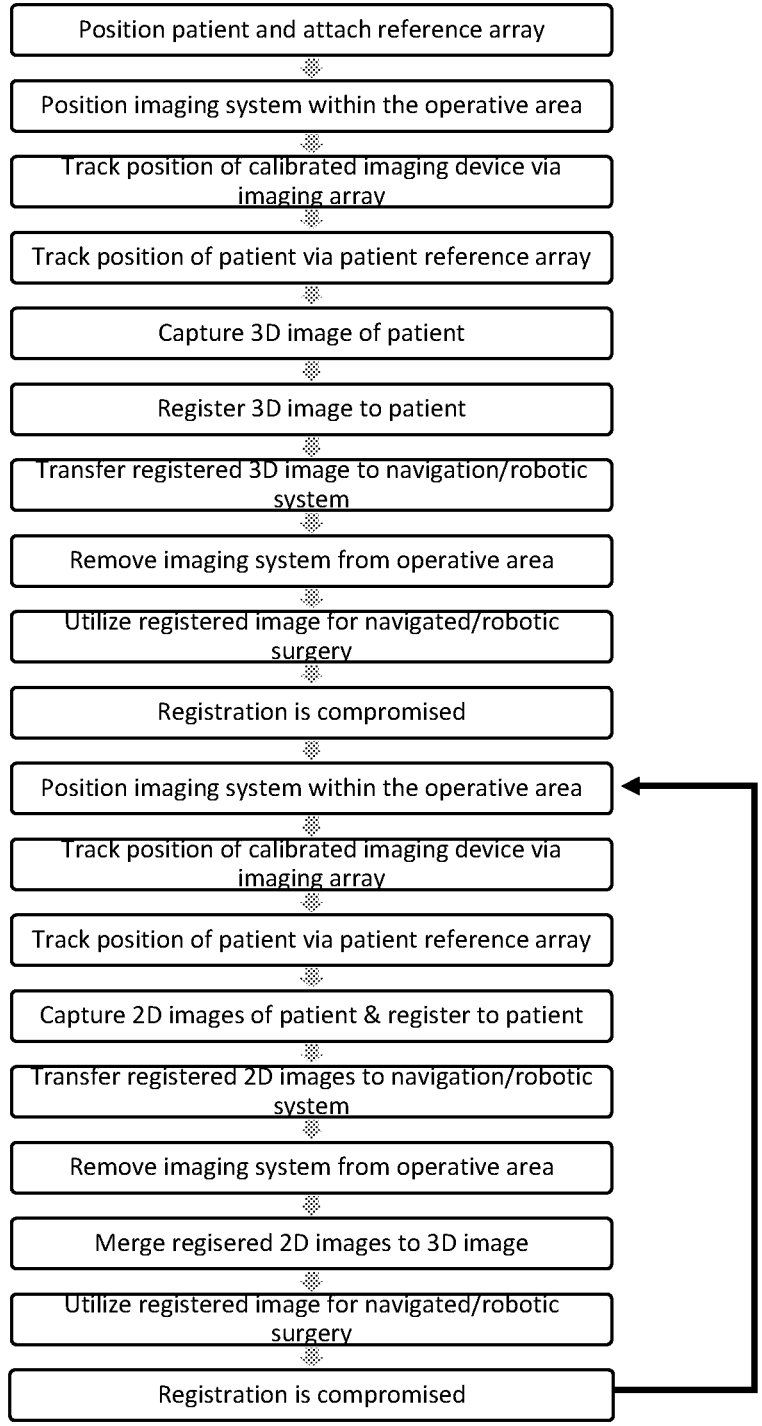

FIG. 30 is a flowchart of a method of registering an intra-op 3D image of a patient in an imaging space to the physical patient in a physical space and recovering registration of the 3D image with intra-op 2D images, preferably without using any embedded radiopaque fiducials in images according to another aspect of the present invention.

Figure 31:
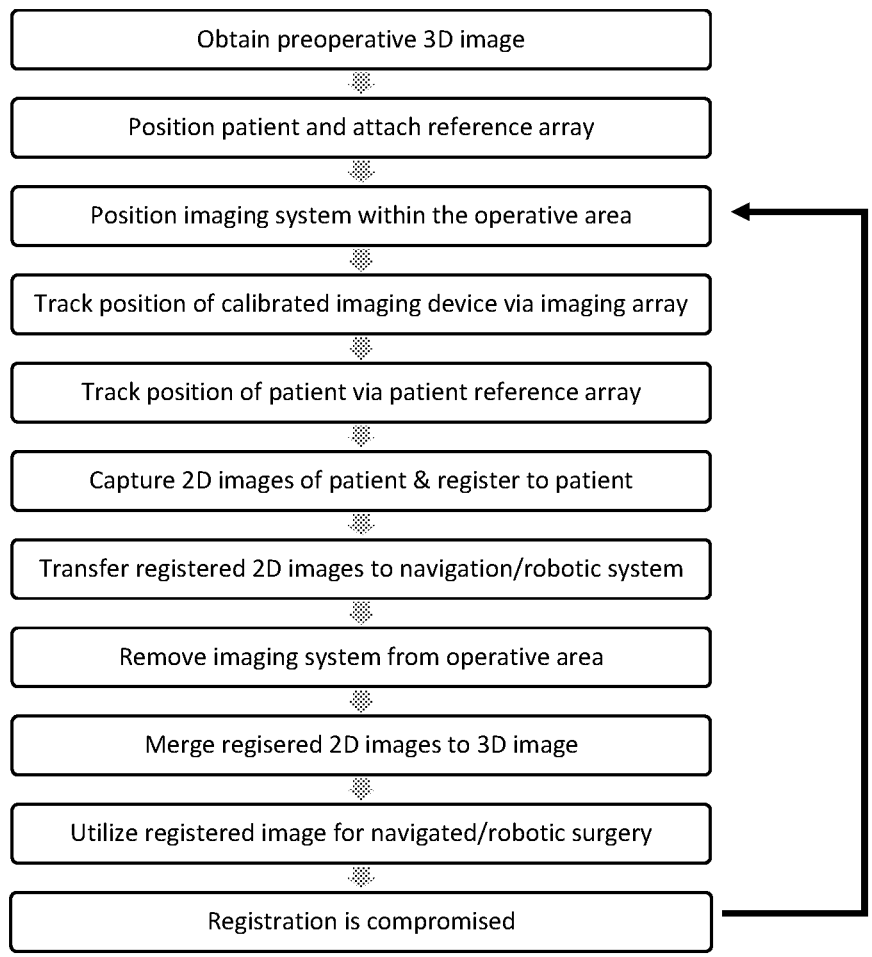

FIG. 31 is a flowchart of a method of registering a pre-op 3D image of a patient in an imaging space to the physical patient in a physical space and recovering registration of the 3D image with intra-op 2D images, preferably without using any embedded radiopaque fiducials in images, according to another aspect of the present invention.

Figure 32:
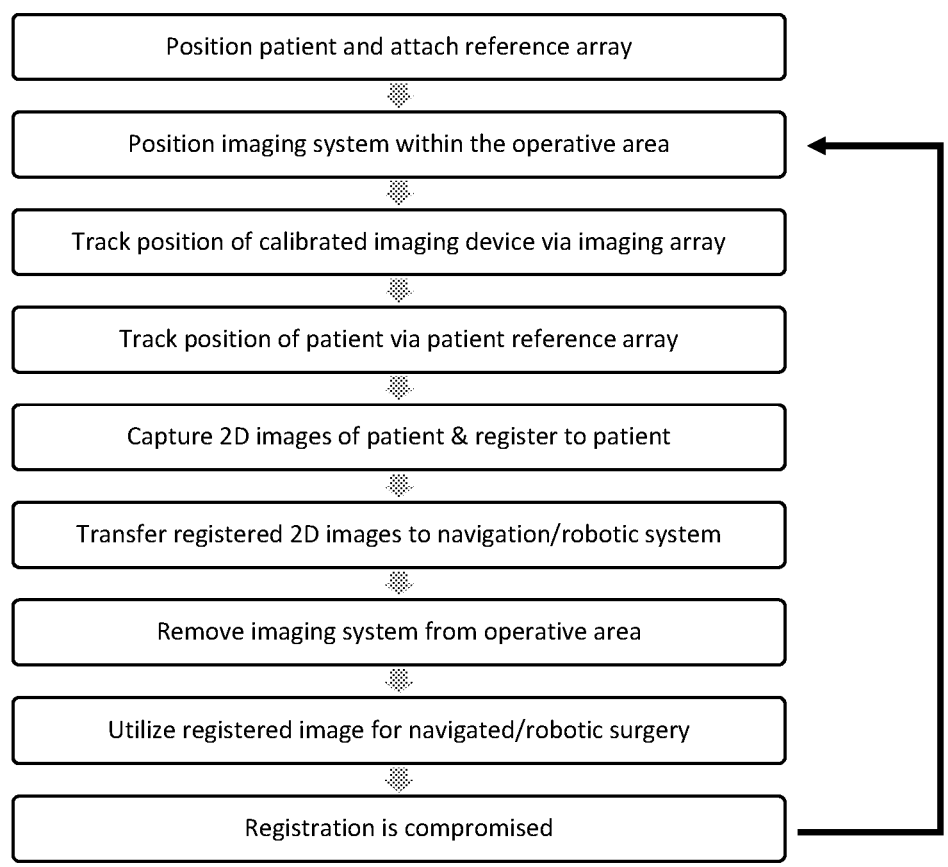

FIG. 32 is a flowchart of a method of registering intra-op 2D image of a patient in an imaging space to the physical patient in a physical space and recovering registration of the 2D images with another set of intra-op 2D images, preferably without using any embedded radiopaque fiducials in images, according to another aspect of the present invention.

Figure 33:
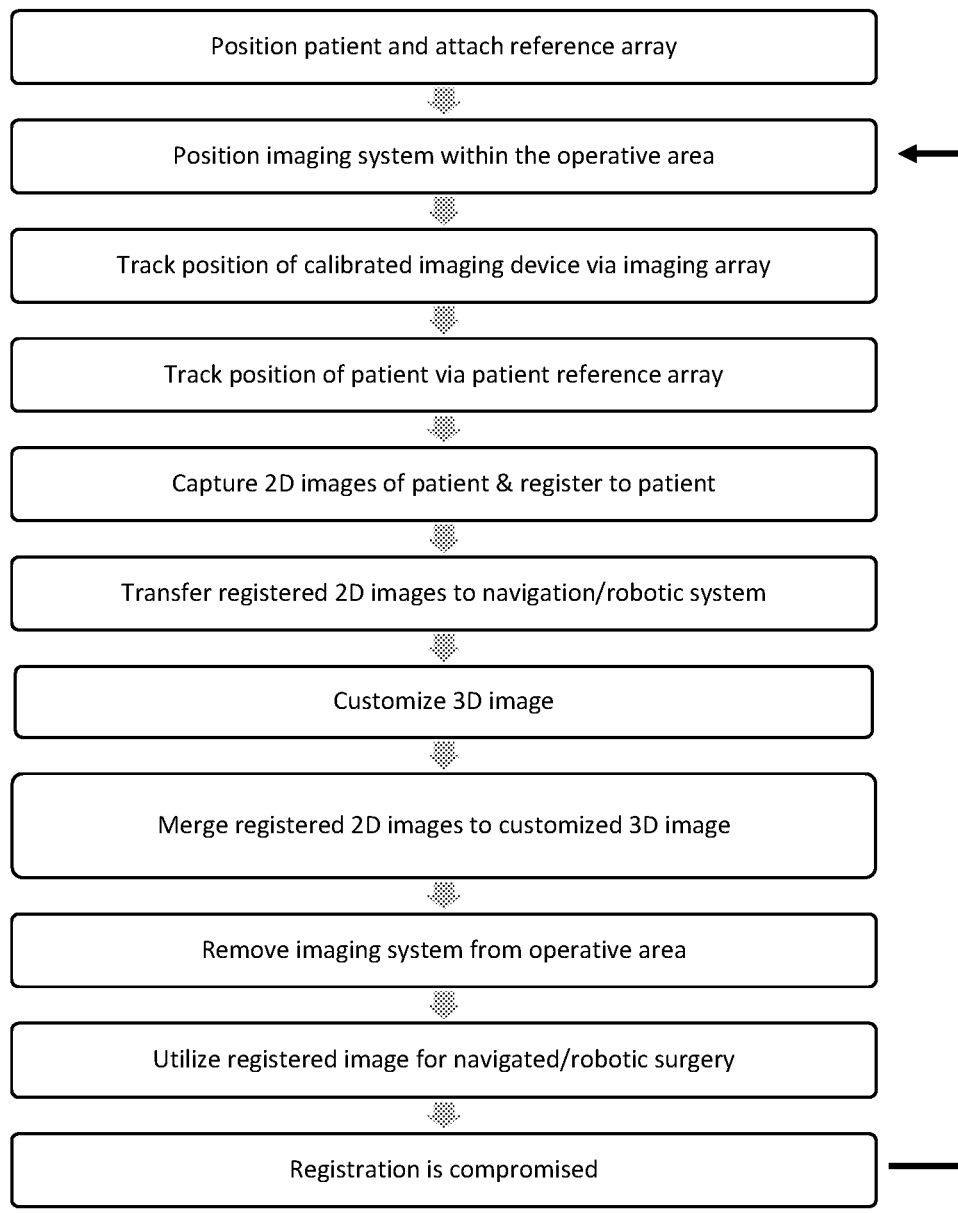

FIG. 33 is a flowchart of a method of registering a synthetically created 3D image based on an intra-op 2D image of a patient, preferably without using any embedded radiopaque fiducials in images.

FIG. 34 is a perspective view of a calibration fixture for calibrating the imaging device according to another aspect of the present invention.

DETAILED DESCRIPTION OF THE DISCLOSURE

For purposes of this application, the terms "code", "software", "program", "application", "software code", "software module", "module" and "software program" are used interchangeably to mean software instructions that are executable by a processor. A "user" can be a physician or other medical professional.

Figure 1:
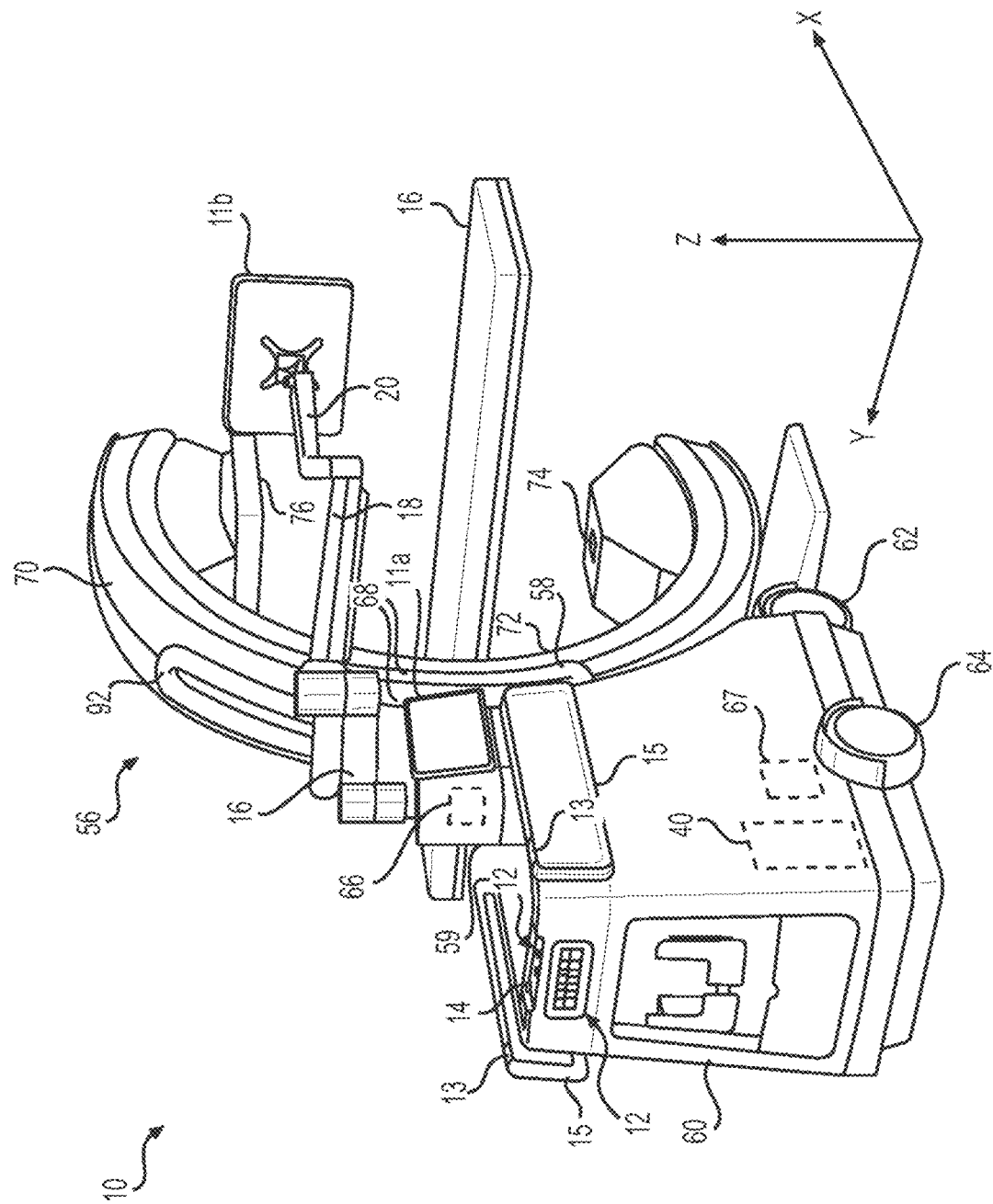
FIG. 1 is a perspective rear view of an imaging system according to one embodiment of the present invention.

FIG. 1 is a schematic diagram showing an imaging system 10, such as a computerized tomographic (CT) x-ray scanner, in accordance with one embodiment of the invention. The imaging system 10 includes a movable station 60 and a gantry 56. The movable station includes a vertical shaft 59 and a gantry mount 58 which is rotatably attached to the vertical shaft. The movable station 60 includes two front omni-directional wheels 62 and two rear omni-directional wheels 64, which together provide movement of the movable station 60 in any direction in an X-Y plane. The omni-directional wheels 62,64 can be obtained, for example, from Active Robots Limited of Somerset, U.K. A pair of handles 13 mounted to the housing of the movable station 60 allow a user to manually maneuver the station.

A motor 66 attached to the vertical shaft 59 is designed to rotate the gantry mount 58 full 360 degrees about the X-axis and a motor 67 moves the gantry mount 58 vertically along the z-axis under the control of the control module 51.

The gantry 56 includes a first C-arm 70 slidably coupled to the gantry mount 58 and a second C-arm 72 which is slidably coupled to the first C-arm. In the embodiment shown, the first and second C-arms 70,72 are outer and inner C-arms, respectively. In the embodiment shown, the outer and inner C-arms 70,72 are circular in shape and rotate circumferentially about a central axis so as to allow imaging of a patient who is lying in bed 16 without the need to transfer the patient.

An imaging signal transmitter 74 such as an X-ray beam transmitter is mounted to one side of the second C-arm 72 while an imaging sensor 74 such as an X-ray detector array is mounted to the other side of the second C-arm and faces the transmitter. In operation, the X-ray transmitter 74 transmits an X-ray beam which is received by the X-ray detector 76 after passing through a relevant portion of a patient (not shown).

In one embodiment, the system 10 is a multi-modality x-ray imaging system designed with surgery in mind. The three imaging modalities include fluoroscopy, 2D Radiography, and Cone-beam CT. Fluoroscopy is a medical imaging technique that shows a continuous X-ray image on a monitor, much like an X-ray movie. 2D Radiography is an imaging technique that uses X-rays to view the internal structure of a non-uniformly composed and opaque object such as the human body. CBCT (cone beam 3D imaging or cone beam computer tomography) also referred to as C-arm CT, is a medical imaging technique consisting of X-ray computed tomography where the X-rays are divergent, forming a cone.

The movable station 60 includes an imaging controller system 40 which serves a dual function of (1) controlling the movement of the omni-directional wheels 62,64, gantry mount 58 and the gantry 56 to position the imaging signal transmitter 74 in relation to the patient, and (2) controlling imaging functions for imaging the patient once the gantry 56 has been properly positioned.

Figure 2:
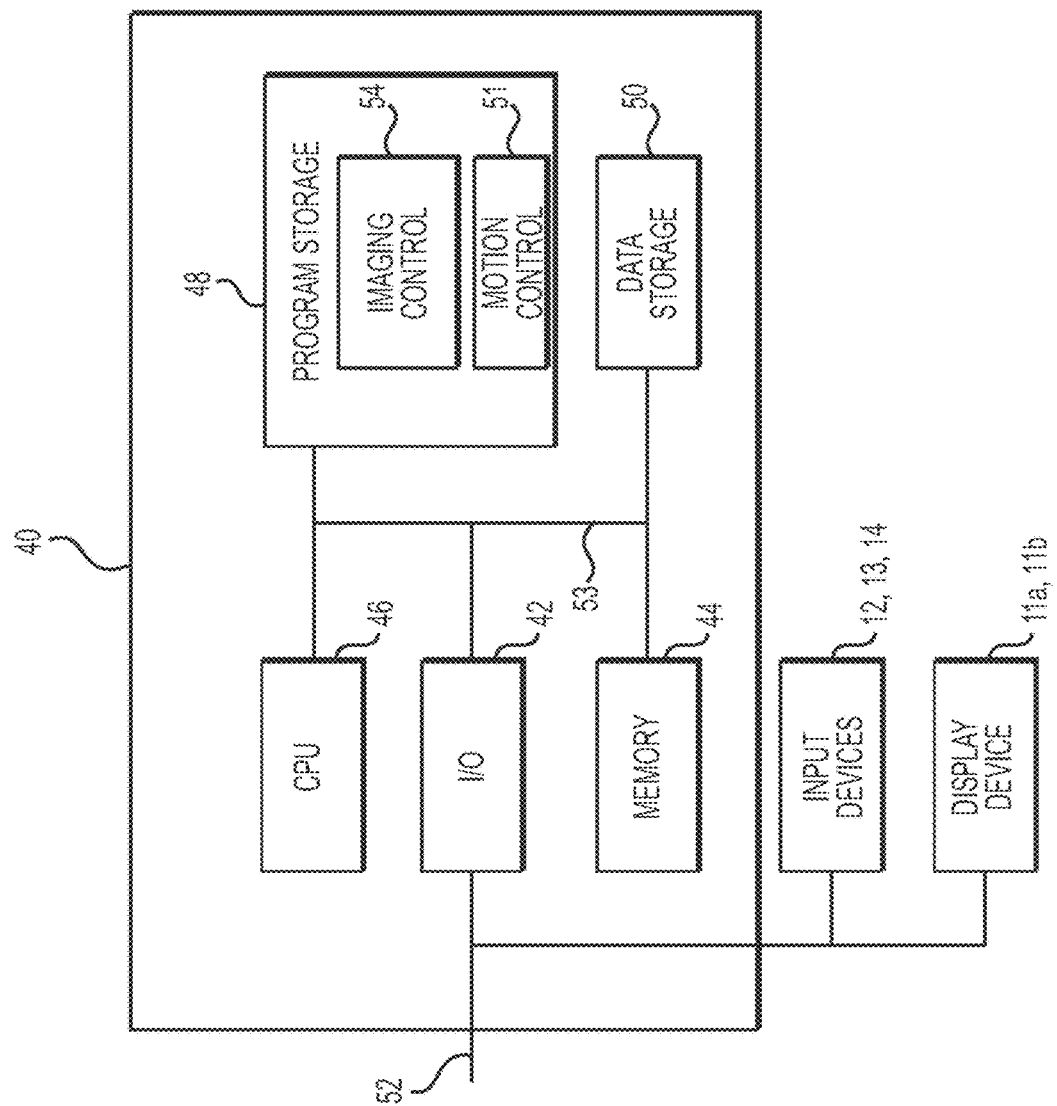
FIG. 2 is a schematic diagram of an imaging controller system 40 according to one embodiment of the present invention.

Referring now to FIG. 2, the imaging controller system 40 of the present invention is connected to a communication link 52 through an I/O interface 42 such as a USB (universal serial bus) interface, which receives information from and sends information over the communication link 52. The imaging controller system 40 includes memory storage 44 such as RAM (random access memory), processor (CPU) 46, program storage 48 such as ROM or EEPROM, and data storage 50 such as a hard disk, all commonly connected to each other through a bus 53. The program storage 48 stores, among others, imaging control module 54 and motion control module 51, each containing software to be executed by the processor 46. The motion control module 51 executed by the processor 46 controls the wheels 62,64 of the movable station 60 and various motors in the gantry mount 58 and gantry 56 to position the station 60 near the patient and position the gantry in an appropriate position for imaging a relevant part of the patient.

The imaging control module 54 executed by the processor 46 controls the imaging signal transmitter 74 and detector array 76 to image the patient body. In one embodiment, the imaging control module images different planar layers of the body and stores them in the memory 44. In addition, the imaging control module 54 can process the stack of images stored in the memory 44 and generate a three dimensional image. Alternatively, the stored images can be transmitted to a host system (not shown) for image processing.

The motion control module 51 and imaging control module 54 include a user interface module that interacts with the user through the display devices 11a and 11b and input devices such as keyboard and buttons 12 and joy stick 14. Strain gauges 13 mounted to the handles 15 are coupled to the I/O device 42 and conveniently provide movement of the movable station 12 in any direction (X, Y, Wag) while the user is holding the handles 15 by hand as will be discussed in more detail below. The user interface module assists the user in positioning the gantry 56. Any of the software program modules in the program storage 48 and data from the data storage 50 can be transferred to the memory 44 as needed and is executed by the CPU 46. The display device 11a is attached to the housing of the movable station 60 near the gantry mount 58 and display device 11b is coupled to the movable station through three rotatable display arms 16, 18 and 20. First display arm 16 is rotatably attached to the movable station 60, second display arm 18 is rotatably attached to the first arm 16 and third display arm 20 is rotatably attached to the second display arm. The display devices 11a,11b can have touch screens to also serve as input devices through the use of user interface modules in the modules 51 and 54 to provide maximum flexibility for the user.

Navigation markers 68 placed on the gantry mount 58 are connected to the imaging controller system 40 through the link 52. Under the control of the motion control module 51, the markers 68 allow automatic or semi-automatic positioning of the gantry 56 in relation to the patient bed or OR (operating room) table via a navigation system (not shown). The markers 68 can be optical, electromagnetic or the like.

Information can be provided by the navigation system to command the gantry 56 or system 10 to precise locations. One example would be a surgeon holding a navigated probe at a desired orientation that tells the imaging system 10 to acquire a Fluoro or Radiographic image along that specified trajectory. Advantageously, this will remove the need for scout shots thus reducing x-ray exposure to the patient and OR staff. The navigation markers 68 on the gantry 56 will also allow for automatic registration of 2D or 3D images acquired by the system 10. The markers 68 will also allow for precise repositioning of the system 10 in the event the patient has moved.

In the embodiment shown, the system 10 provides a large range of motion in all 6-degrees of freedom ("DOF"). Under the control of the motion control module 51, there are two main modes of motion: positioning of the movable station 60 and positioning of the gantry 56.

The movable station 60 positioning is accomplished via the four omni-directional wheels 62,64. These wheels 62,64 allow the movable station 60 to be positioned in all three DOF about the horizontal plane (X,Y,Wag). "Wag" is a system 10 rotation about the vertical axis (Z-axis), "X" is a system forward and backward positioning along the X-axis, and "Y" is system 10 lateral motion along the Y-axis. Under the control of the control module 51, the system 10 can be positioned in any combination of X, Y, and Wag (Wag about any arbitrary Z-axis due to use of omnidirectional wheels 62,64) with unlimited range of motion. In particular, the omni-directional wheels 62,64 allow for positioning in tight spaces, narrow corridors, or for precisely traversing up and down the length of an OR table or patient bed.

The gantry 56 positioning is accomplished about (Z, Tilt, Rotor). "Z" is gantry 56 vertical positioning, "Tilt" is rotation about the horizontal axis parallel to the X-axis as described above, and "Rotor" is rotation about the horizontal axis parallel to the Y-axis as described above.

Together with the movable station 60 positioning and gantry 56 positioning, the system 10 provides a range of motion in all 6 DOF (X, Y, Wag, Z, Tilt and Rotor) to place the movable station 60 and the imaging transmitter 74 and sensor 76 precisely where they are needed. Advantageously, 3-D imaging can be performed regardless of whether the patient is standing up, sitting up or lying in bed and without having to move the patient.

Precise positions of the system 10 can be stored in the storage memory 50 and recalled at any time by the motion control module 51. This is not limited to gantry 56 positioning but also includes system 10 positioning due to the omni-directional wheels 62,64.

Figure 3:
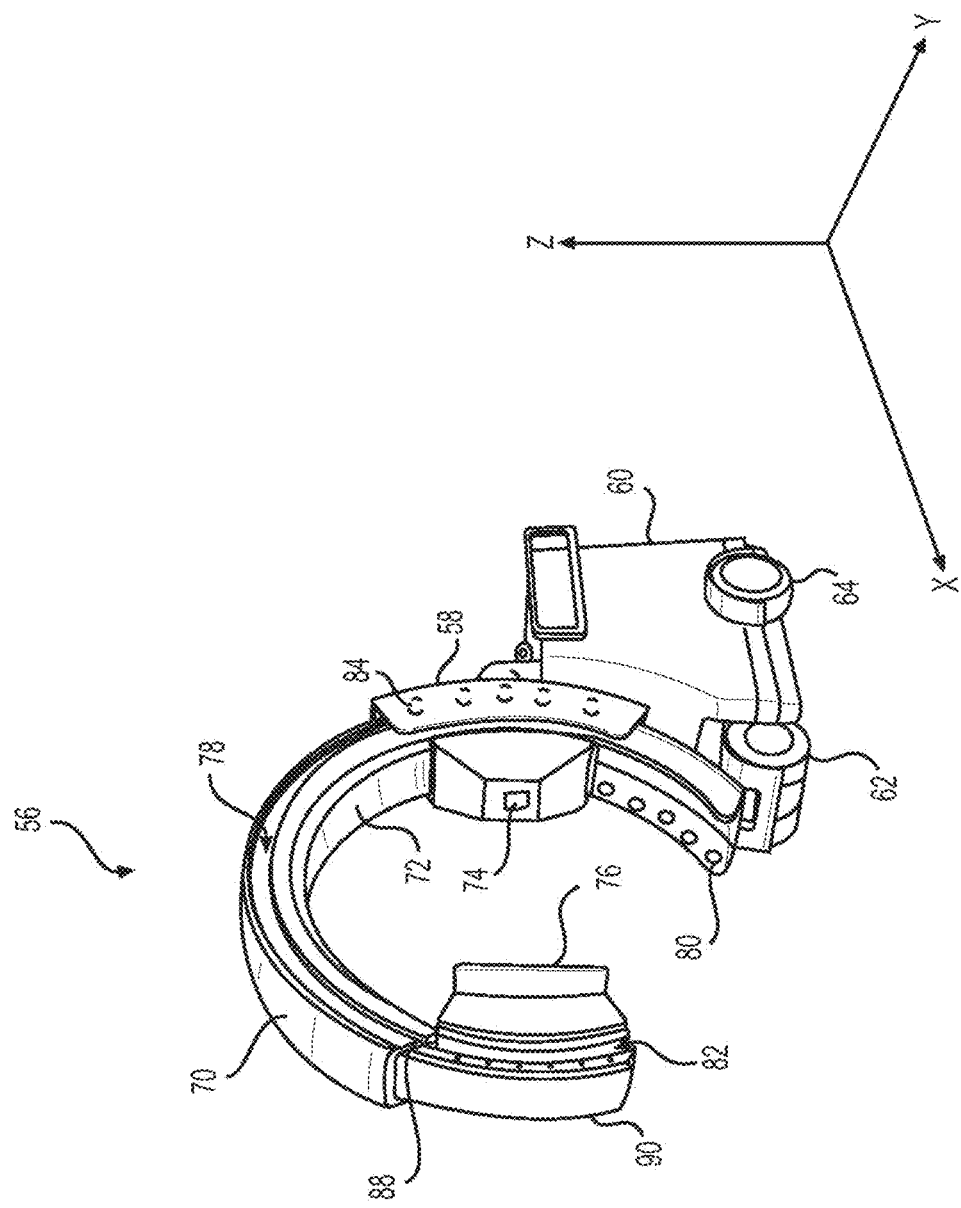
FIG. 3 is a perspective front view of the imaging system of FIG. 1.
Figure 4:
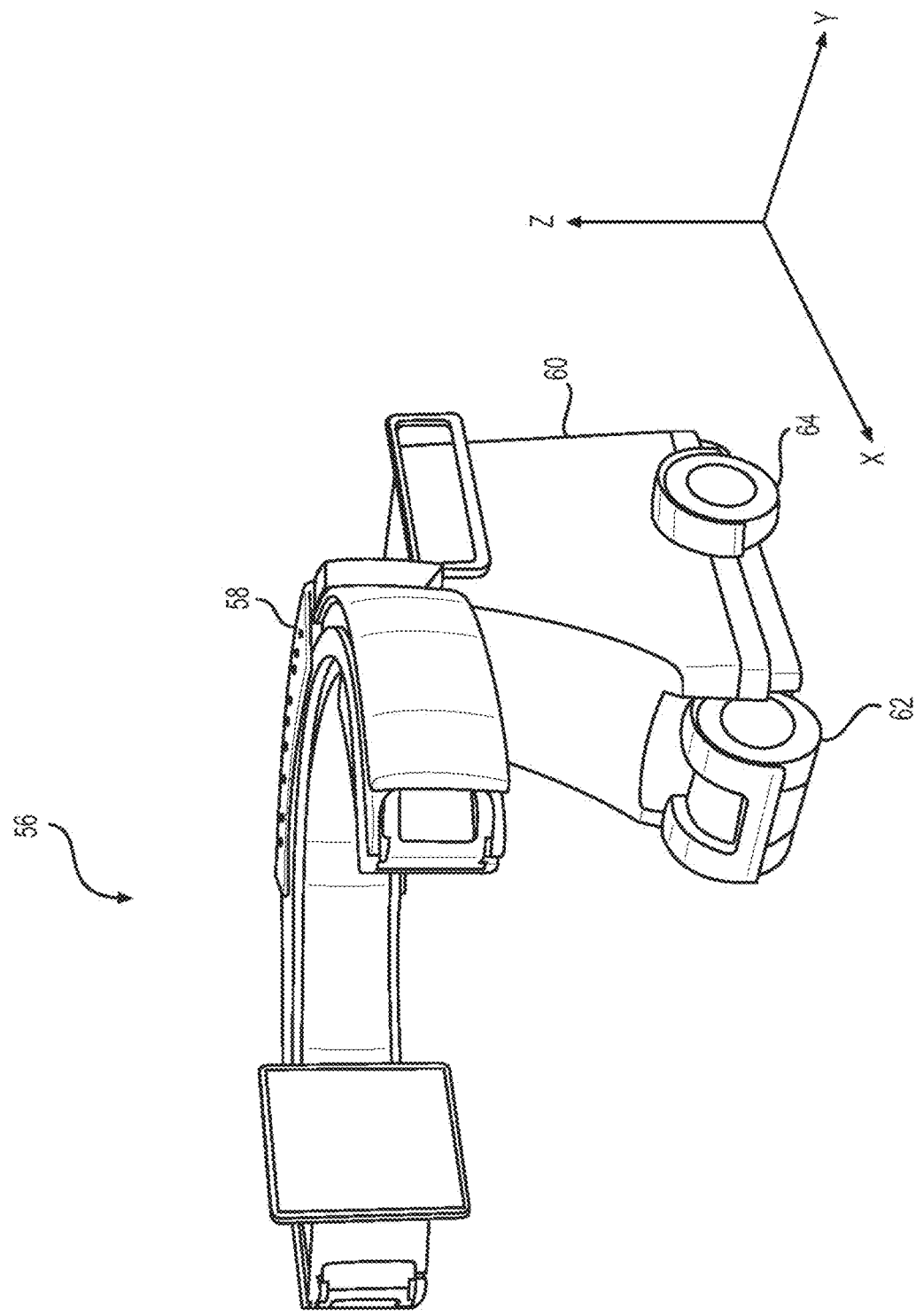
FIG. 4 is a perspective view of the imaging system of FIG. 1 in which the gantry has been rotated about the X-axis by 90 degrees.

As shown in FIG. 3, each of the gantry mount 58, outer C-arm 70 and inner C-arm 72 respectively has a pair of side frames 86, 88,90 that face each other. A plurality of uniformly spaced rollers 84 are mounted on the inner sides of the side frames 86 of the gantry mount 58. The outer C-arm 70 has a pair of guide rails 78 on the outer sides of the side frames 88. The rollers 84 are coupled to the guide rails 78.

As shown, the rollers 84 and the guide rails 78 are designed to allow the outer C-arm 78 to telescopically slide along the gantry mount 58 so as to allow at least 180 degree rotation of the C-arm about its central axis relative to the gantry mount.

A plurality of uniformly spaced rollers 80 are mounted on the inner sides of the side frames 88 of the outer C-arm 70. The inner C-arm 72 has a pair of guide rails 82 on the outer sides of the side frames 90. The rollers 80 are coupled to the guide rails 82. As shown, the rollers 80 and the guide rails 82 are designed to allow the inner C-arm 72 to telescopically slide along the outer C-arm 70 so as to allow at least 180 degree rotation of the C-arm about its central axis relative to the outer C-arm.

Thus, the present invention as disclosed herein advantageously allows the gantry 56 to rotate about its central axis a full 360 degrees to provide the maximum flexibility in positioning the imaging system 10 with minimum disturbance of the patient.

Figure 5:
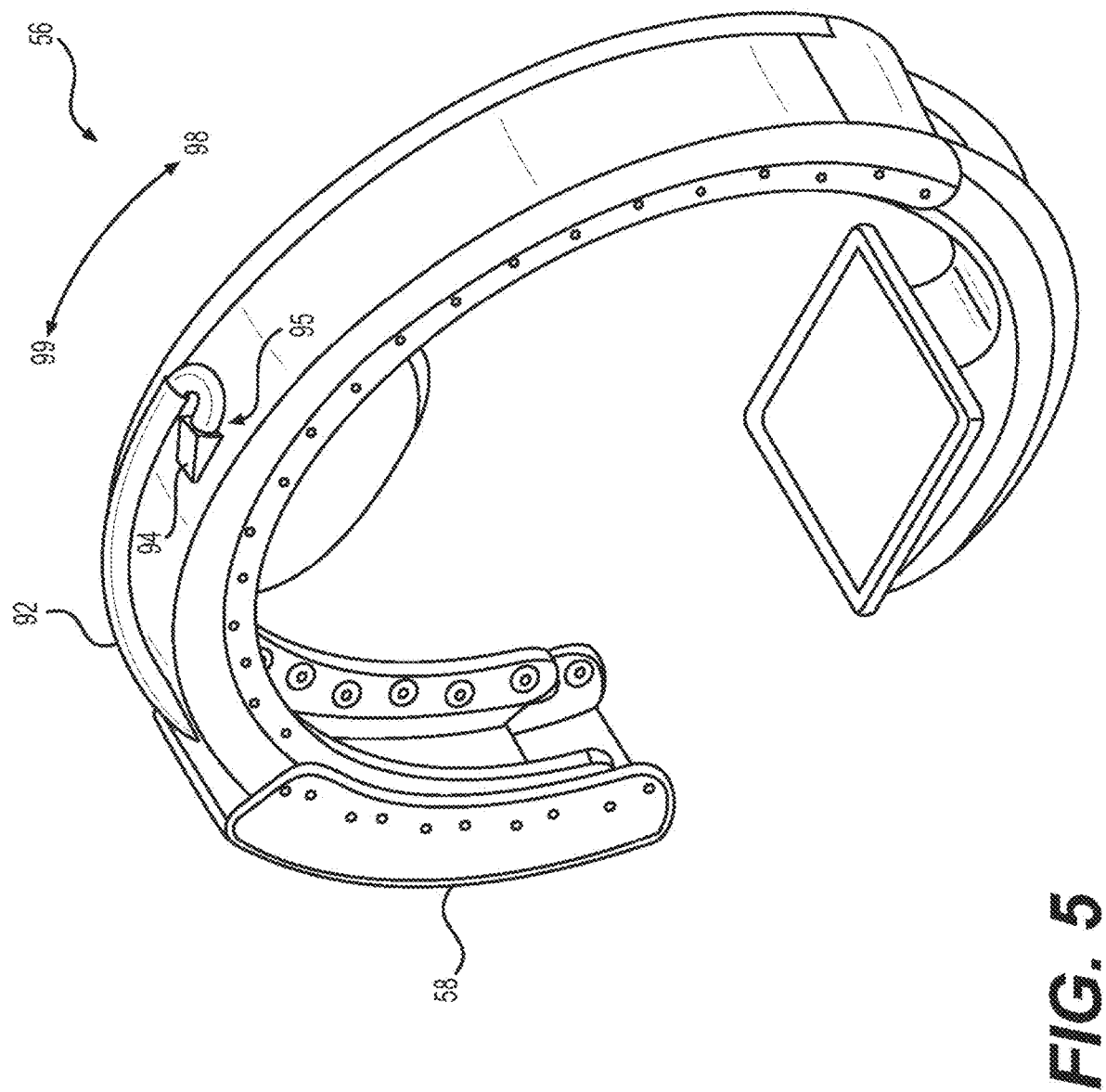
FIG. 5 is a perspective view of the gantry partially showing a cabling arrangement.
Figure 6:
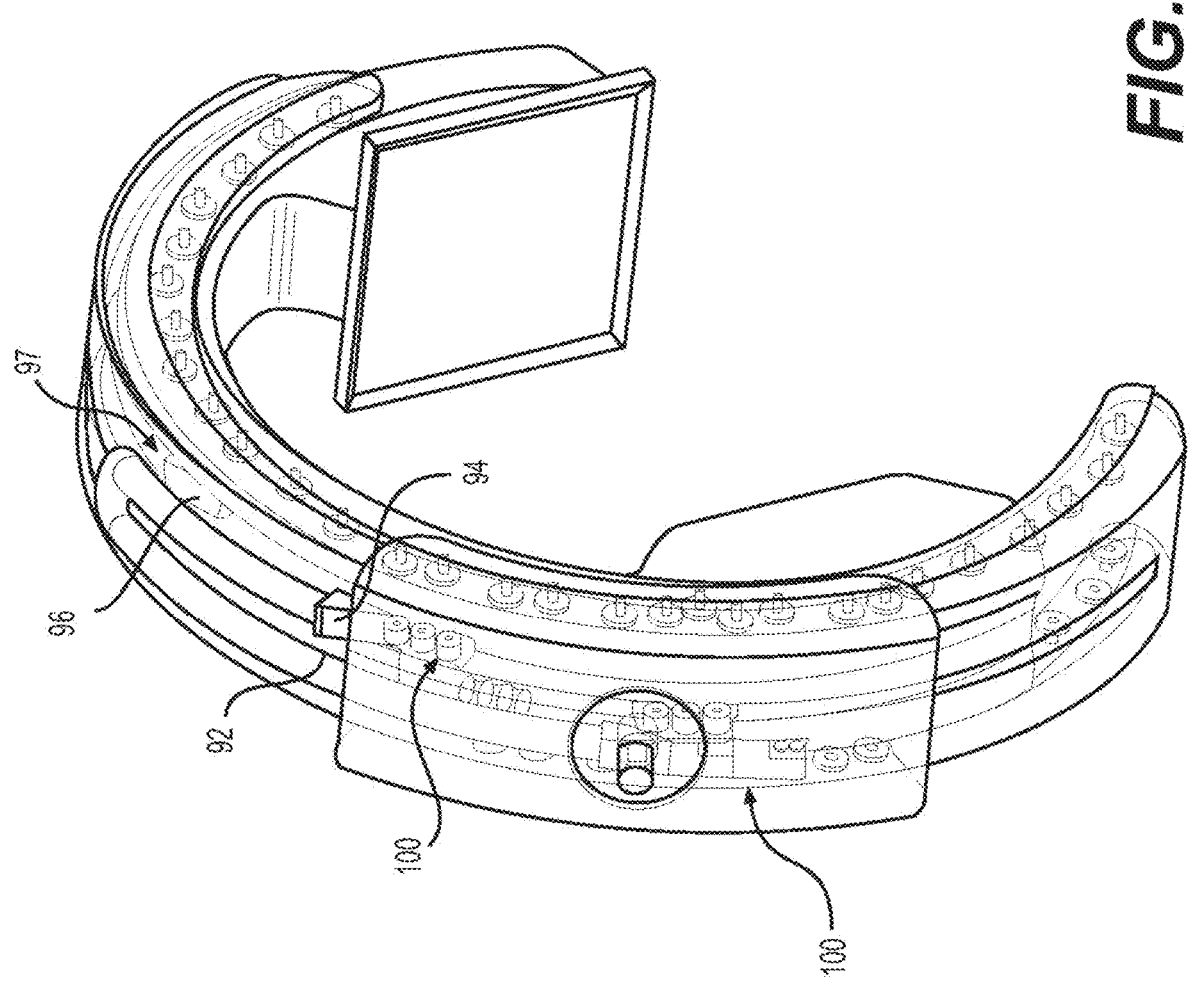
FIG. 6 is a perspective view of the gantry showing the cabling arrangement.
Figure 7:
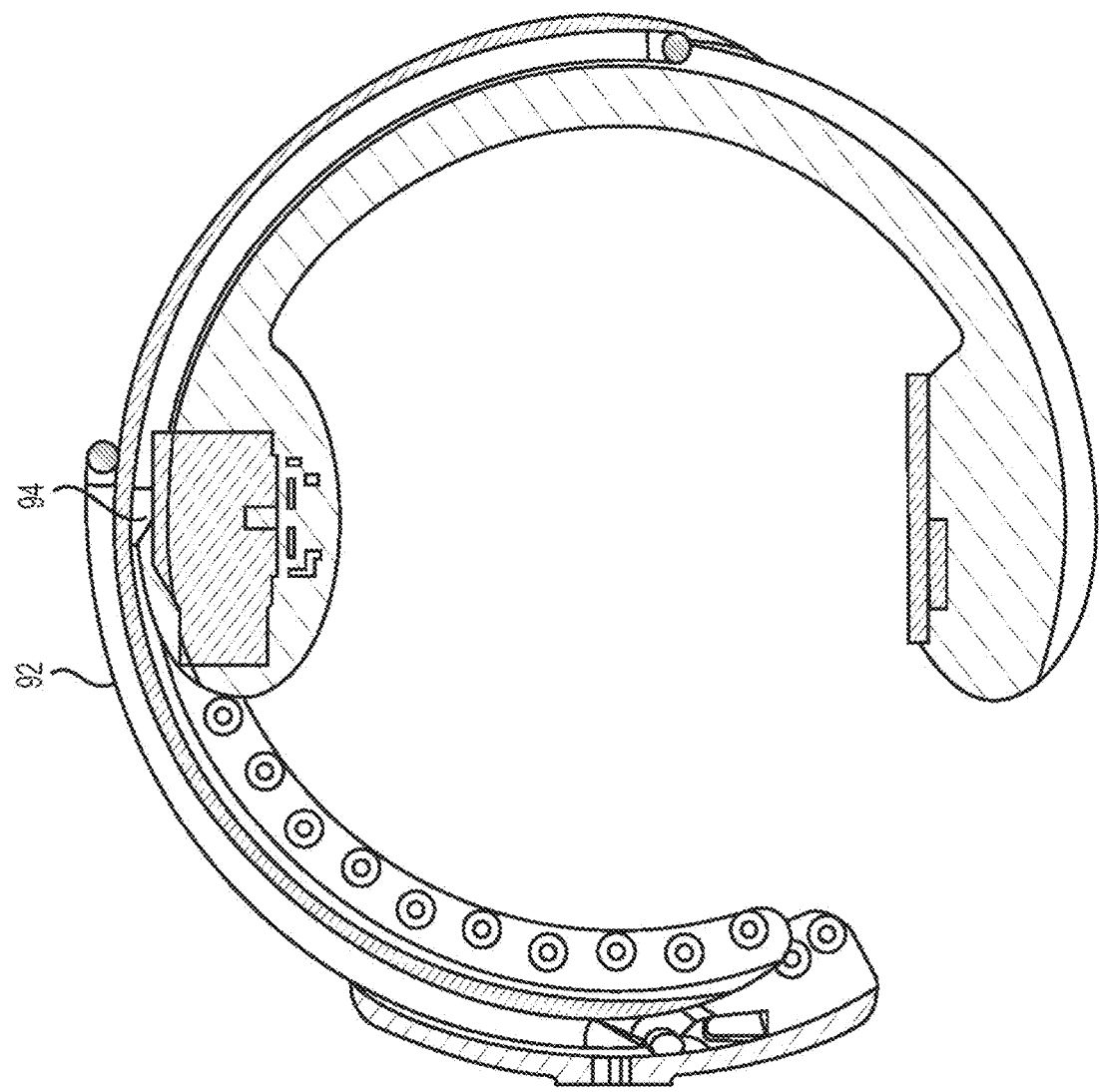
FIG. 7 is a side view of the gantry showing the cabling arrangement.

In another aspect of the present invention, a unique cabling arrangement is provided to make the imaging system 10 more compact and visually more appealing. As shown in FIGS. 5 and 6, a cable carrier/harness 92 contains electrical cables to carry signals between the imaging controller system 40 and various motors, X-ray transmitter 74, imaging sensor 76 and various electronic circuits in the gantry 56. A first cable router 94 is mounted to the outer surface of the outer C-arm 70 and a second cable router 96 is mounted to the outer surface of the inner C-arm 72. Each cable router 94,96 has a through-hole 95,97 through which the cable carrier 92 passes.

The cable carrier 92 extends from the gantry mount 56 over the outer surface of the first C-arm 70, through the through-hole 95 of the first cable router 94 and over an outer surface of the second C-arm 72. The cable carrier 92 overlying the first C-arm 70 extends in a first circumferential direction (clock-wise as shown) 98 and enters the first cable router 94 in a second circumferential direction (counter clock-wise as shown) 99 opposite to the first circumferential direction to create a 180 degree service loop over the outer surface of the first C-arm.

From there, the cable carrier 92 extends in the first circumferential direction 98 and enters the second cable router in the second circumferential direction 99 to create another service loop over the outer surface of the second C-arm 72.

The particular locations of the first and second cable routers 94,96 combined with the service loops allow slack in the cable carrier 92 to provide the gantry 56 with full 360 degrees rotation without tangling or causing stress in the cable carrier. In the embodiment shown, the routers are mounted near the midpoint of the C-arms.

Figure 8:
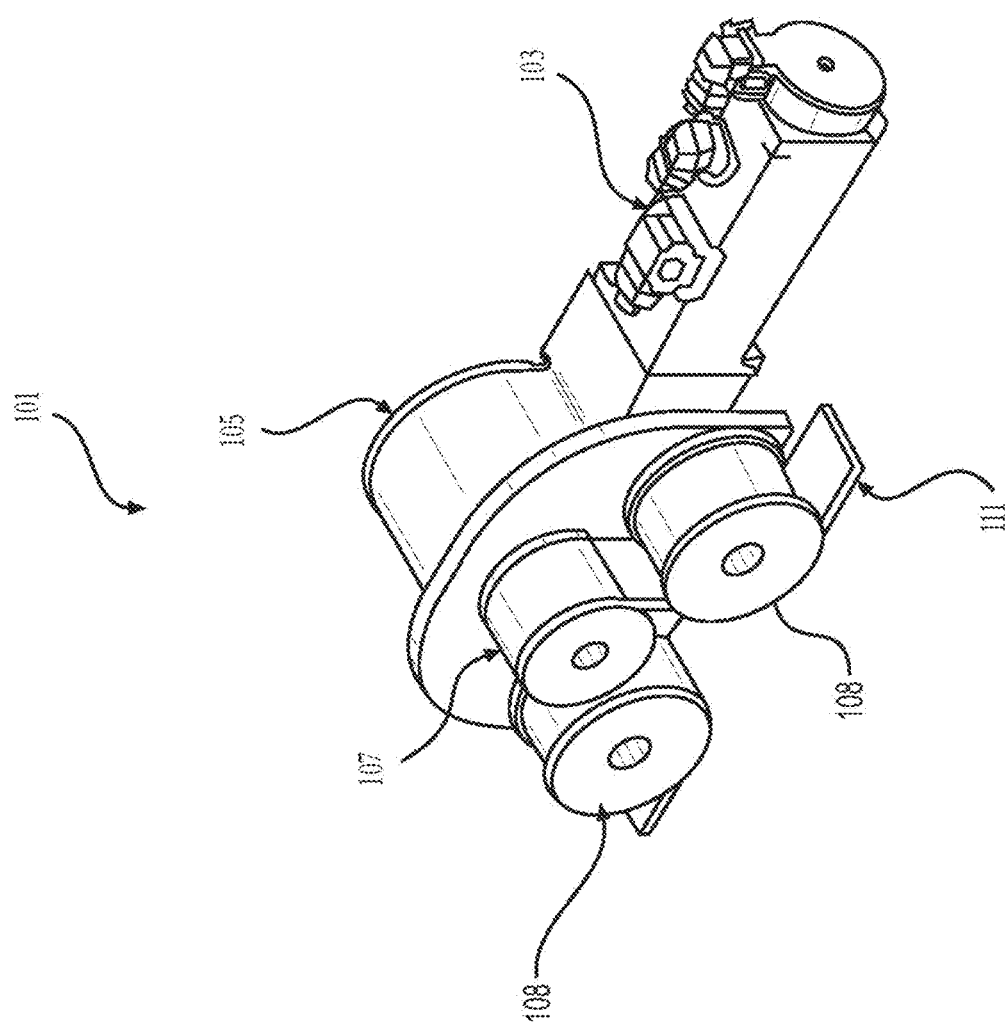
FIG. 8 illustrates a motor assembly for telescopically controlling the C-arms of the gantry.

FIG. 8 illustrates one embodiment of a motor assembly 101 that could be used to telescopically rotate the outer C-arm 70 relative to the gantry mount 58 and inner C-arm 72 relative to the outer C-arm. Each motor assembly 101 includes a servo motor 103 with encoder feedback, gear box 105 to change the turning ratio, drive pulley 107, idler pulleys 108 and belt 111 threaded between the drive pulley and the idler pulleys. One motor assembly 101 is mounted to the gantry mount to move the outer C-arm 70 relative to the gantry mount and another motor assembly is mounted to the outer C-arm near the center of the arm to move the inner C-arm 70 relative to the outer C-arm.

Figure 9A:
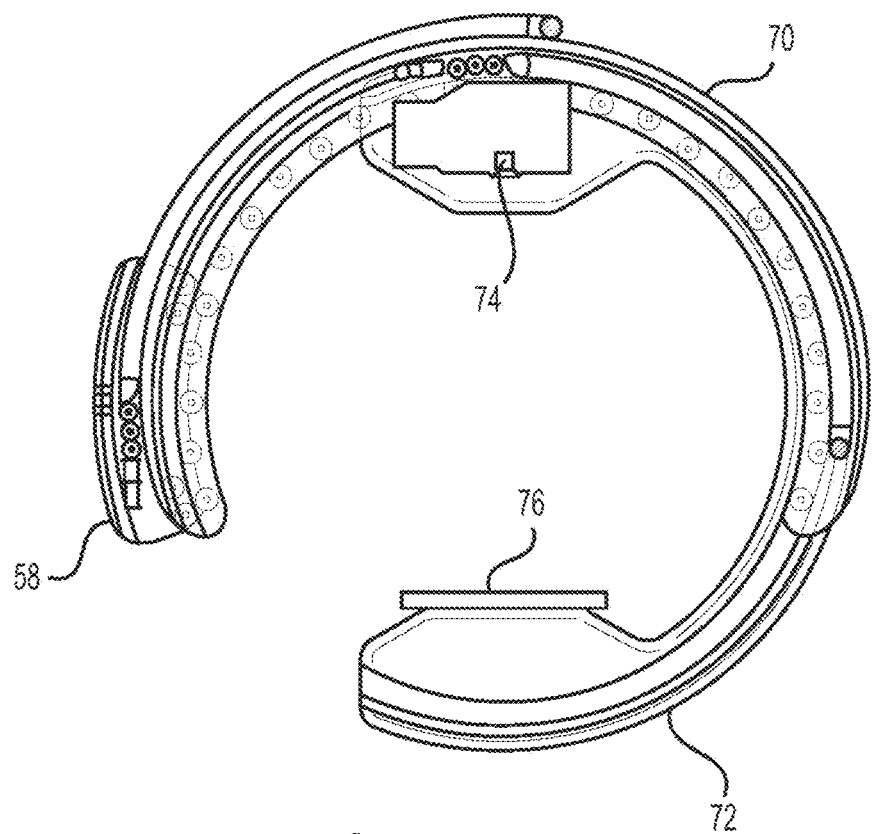
Figure 9B:
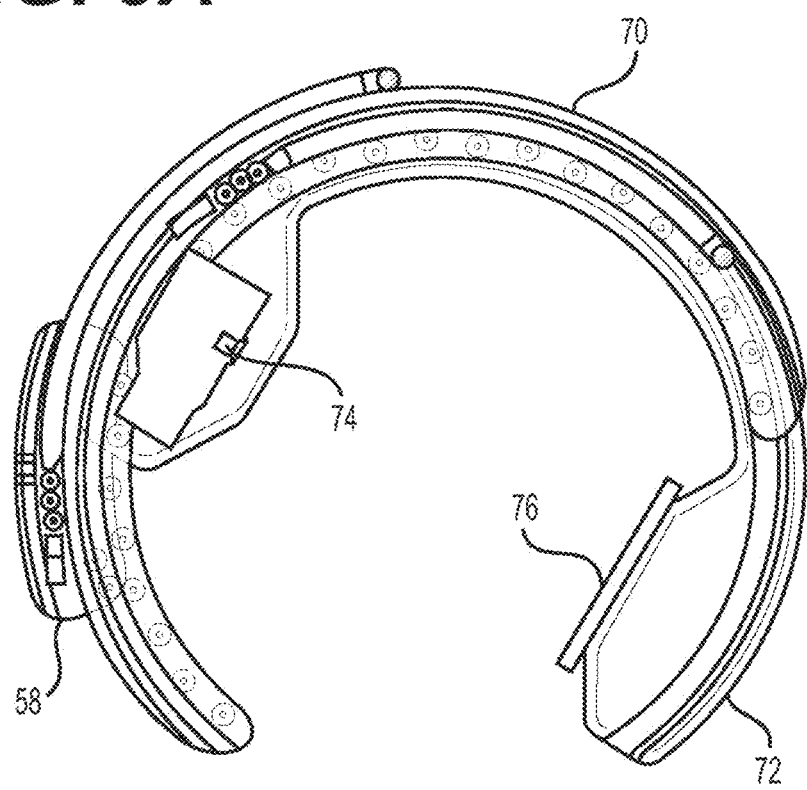
Figure 9C:
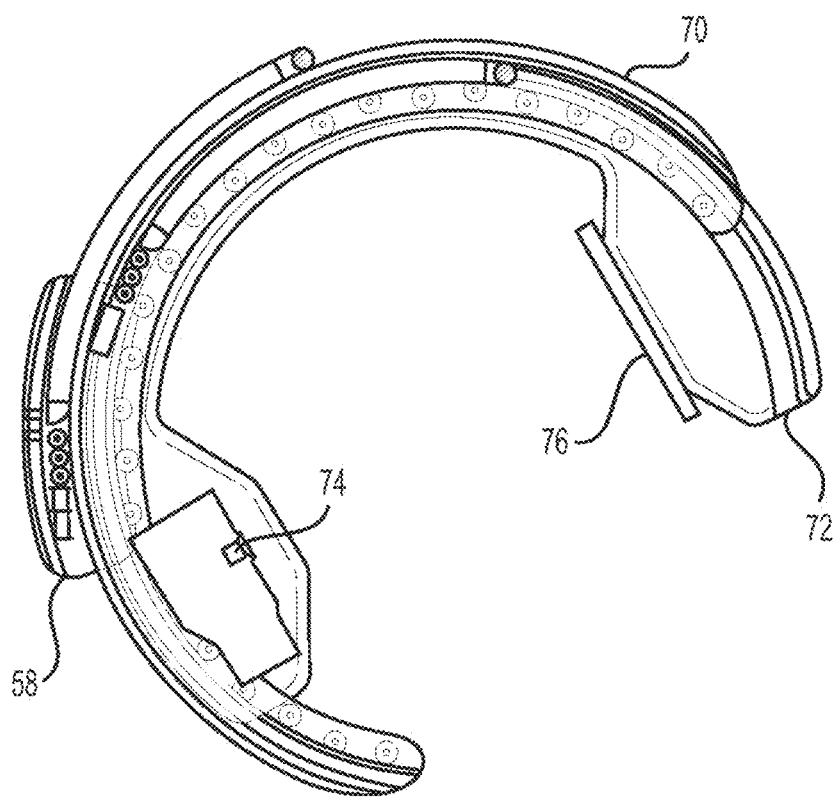
Figure 9D:
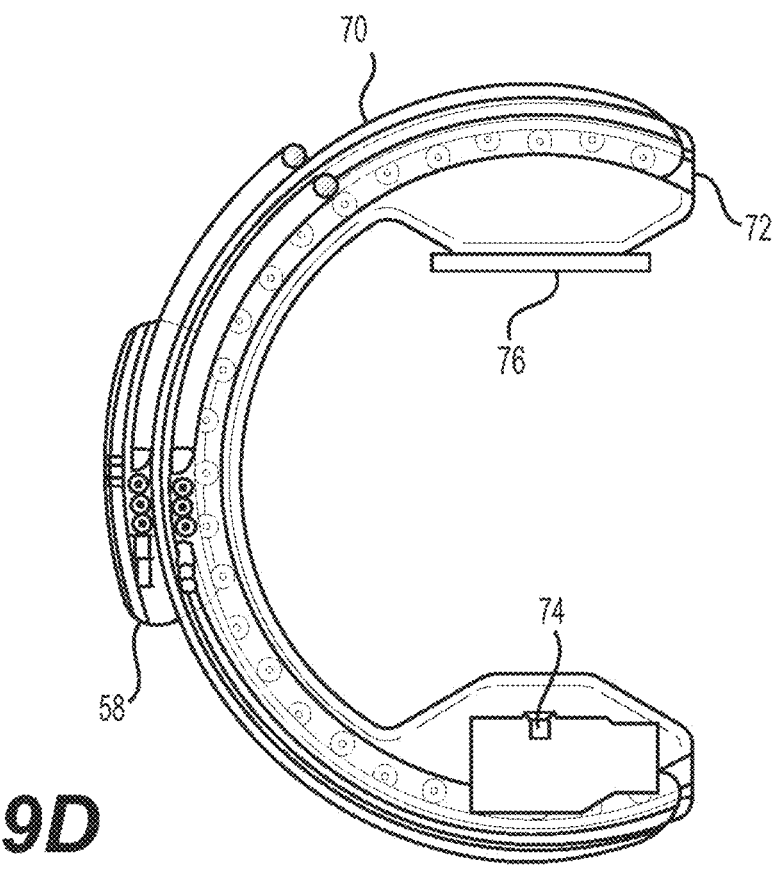
Figure 9E:
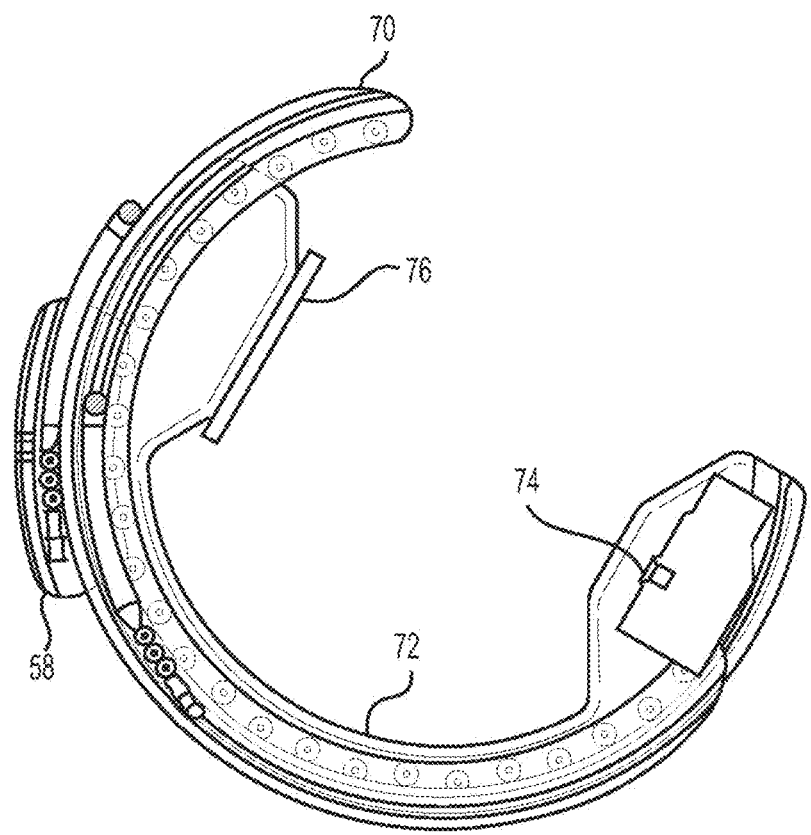
Figure 9F:
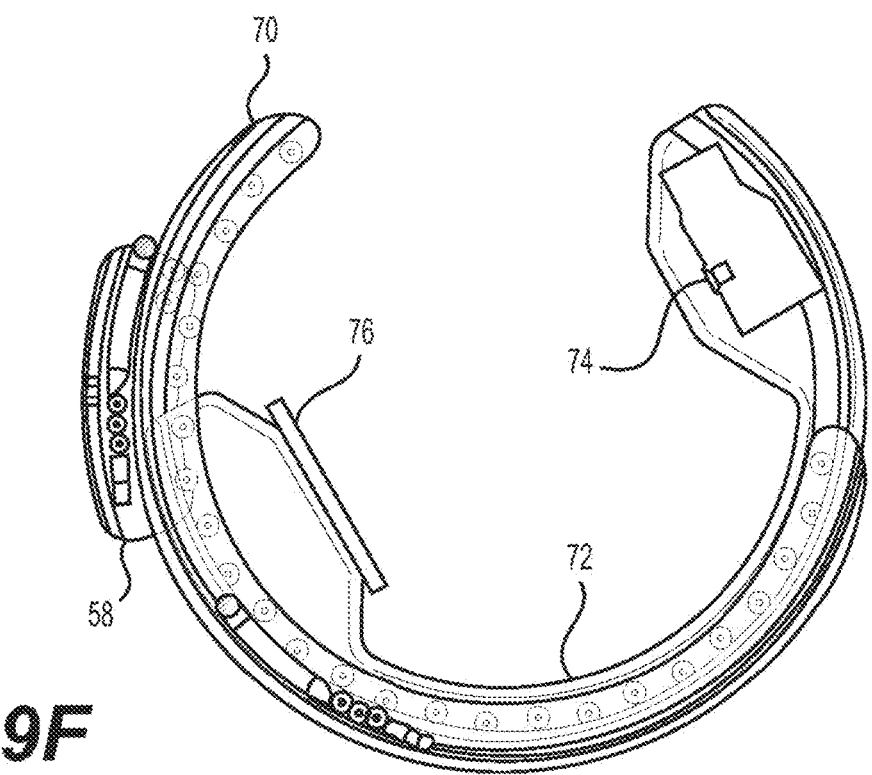
Figure 9G:
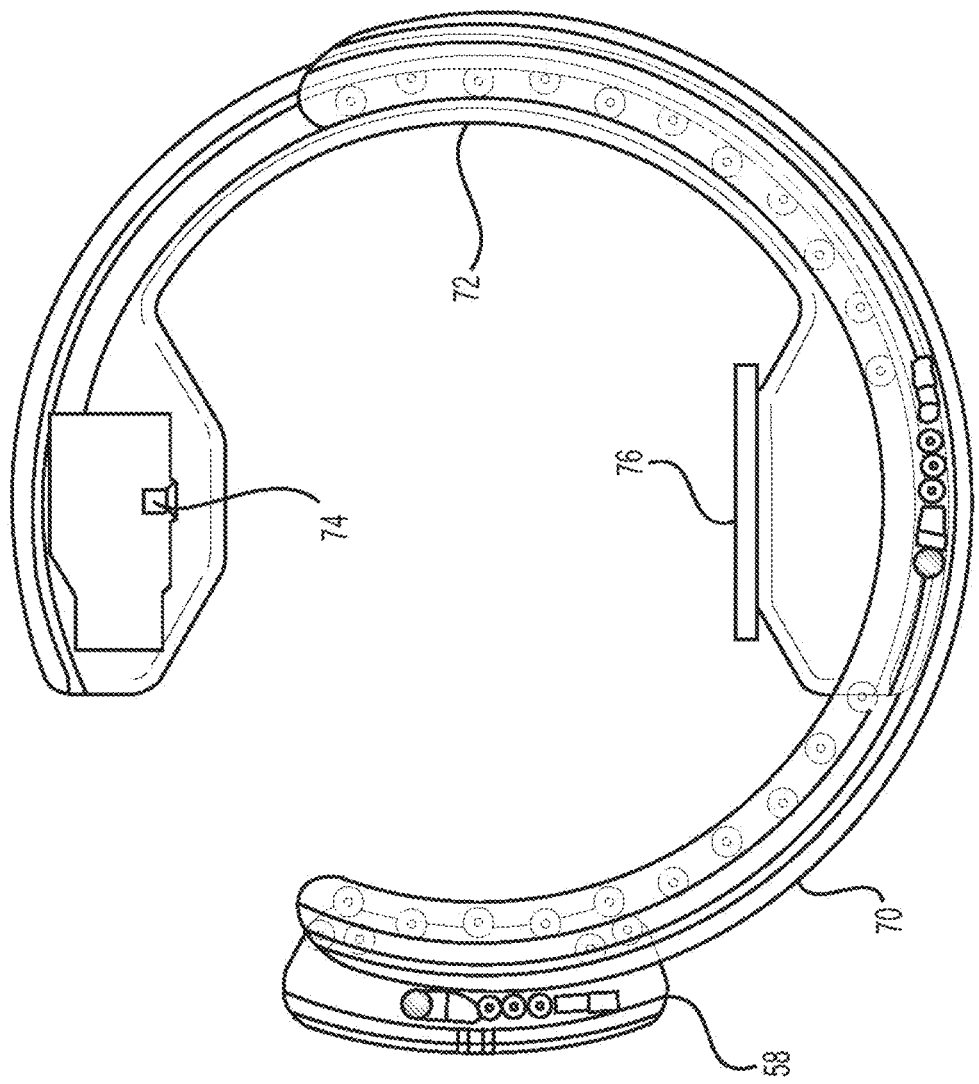

FIGS. 9A-9G illustrate the 360 degree rotation of the gantry 56 in the counter-clockwise direction in 60 degree increments with FIG. 9A representing a zero degree position of the imaging sensor 76 and transmitter 74. FIG. 9B represents a 60 degree turn/position of the gantry 56. For each 60 degree turn of the gantry 56, the motor assemblies 101, under the control of the motion control module 51, turn the inner C-arm 72 by 30 degrees counter-clock wise and also turn the outer C-arm 70 by 30 degrees counter-clock wise for a combined 60 degree turn. FIG. 9G represents a full 360 degree turn of the gantry 56. As can be seen, the outer C-arm 70 and inner C-arm 72 have each moved 180 degrees from the original zero degree position of FIG. 9A.

As described above in detail, the present invention in various embodiments provide the following benefits: (1) movement of the system in any X-Y direction with Wag about any Z-axis from the use of omni-directional wheels 62,64; (2) double telescoping C-gantry for full 360-degree imaging beam rotation; (3) imaging while lying in bed, sitting or standing such as standing CBCT; (4) storage and recall of system 10 and gantry 56 positions; (5) quasi-simultaneous multi-planar x-ray imaging; (6) recall of positions via robotics or navigation coordinates.

Turning now to the drawing, FIGS. 10 and 11 illustrate a surgical robot system 100 in accordance with an exemplary embodiment. Surgical robot system 100 may include, for example, a surgical robot 102, one or more robot arms 104, a base 106, a display 110, an end-effector 112, for example, including a guide tube 114, and one or more tracking markers 118. The surgical robot system 100 may include a patient tracking device 116 also including one or more tracking markers 118, which is adapted to be secured directly to the patient 210 (e.g., to the bone of the patient 210). The surgical robot system 100 may also utilize a camera 200, for example, positioned on a camera stand 202. The camera stand 202 can have any suitable configuration to move, orient, and support the camera 200 in a desired position. The camera 200 may include any suitable camera or cameras, such as one or more infrared cameras (e.g., bifocal or stereophotogrammetric cameras), able to identify, for example, active and passive tracking markers 118 in a given measurement volume viewable from the perspective of the camera 200. The camera 200 may scan the given measurement volume and detect the light that comes from the markers 118 in order to identify and determine the position of the markers 118 in three-dimensions. For example, active markers 118 may include infrared-emitting markers that are activated by an electrical signal (e.g., infrared light emitting diodes (LEDs)), and passive markers 118 may include retro-reflective markers that reflect infrared light (e.g., they reflect incoming IR radiation into the direction of the incoming light), for example, emitted by illuminators on the camera 200 or other suitable device.

FIGS. 10 and 11 illustrate a potential configuration for the placement of the surgical robot system 100 in an operating room environment. For example, the robot 102 may be positioned near or next to patient 210. Although depicted near the head of the patient 210, it will be appreciated that the robot 102 can be positioned at any suitable location near the patient 210 depending on the area of the patient 210 undergoing the operation. The camera 200 may be separated from the robot system 100 and positioned at the foot of patient 210. This location allows the camera 200 to have a direct visual line of sight to the surgical field 208. Again, it is contemplated that the camera 200 may be located at any suitable position having line of sight to the surgical field 208. In the configuration shown, the surgeon 120 may be positioned across from the robot 102, but is still able to manipulate the end-effector 112 and the display 110. A surgical assistant 126 may be positioned across from the surgeon 120 again with access to both the end-effector 112 and the display 110. If desired, the locations of the surgeon 120 and the assistant 126 may be reversed. The traditional areas for the anesthesiologist 122 and the nurse or scrub tech 124 remain unimpeded by the locations of the robot 102 and camera 200.

With respect to the other components of the robot 102, the display 110 can be attached to the surgical robot 102 and in other exemplary embodiments, display 110 can be detached from surgical robot 102, either within a surgical room with the surgical robot 102, or in a remote location. End-effector 112 may be coupled to the robot arm 104 and controlled by at least one motor. In exemplary embodiments, end-effector 112 can comprise a guide tube 114, which is able to receive and orient a surgical instrument 608 (described further herein) used to perform surgery on the patient 210. As used herein, the term "end-effector" is used interchangeably with the terms "end-effectuator" and "effectuator element." Although generally shown with a guide tube 114, it will be appreciated that the end-effector 112 may be replaced with any suitable instrumentation suitable for use in surgery. In some embodiments, end-effector 112 can comprise any known structure for effecting the movement of the surgical instrument 608 in a desired manner.

The surgical robot 102 is able to control the translation and orientation of the end-effector 112. The robot 102 is able to move end-effector 112 along x-, y-, and z-axes, for example. The end-effector 112 can be configured for selective rotation about one or more of the x-, y-, and z-axis, and a Z Frame axis (such that one or more of the Euler Angles (e.g., roll, pitch, and/or yaw) associated with end-effector 112 can be selectively controlled). In some exemplary embodiments, selective control of the translation and orientation of end-effector 112 can permit performance of medical procedures with significantly improved accuracy compared to conventional robots that utilize, for example, a six degree of freedom robot arm comprising only rotational axes. For example, the surgical robot system 100 may be used to operate on patient 210, and robot arm 104 can be positioned above the body of patient 210, with end-effector 112 selectively angled relative to the z-axis toward the body of patient 210.

In some exemplary embodiments, the position of the surgical instrument 608 can be dynamically updated so that surgical robot 102 can be aware of the location of the surgical instrument 608 at all times during the procedure. Consequently, in some exemplary embodiments, surgical robot 102 can move the surgical instrument 608 to the desired position quickly without any further assistance from a physician (unless the physician so desires). In some further embodiments, surgical robot 102 can be configured to correct the path of the surgical instrument 608 if the surgical instrument 608 strays from the selected, preplanned trajectory. In some exemplary embodiments, surgical robot 102 can be configured to permit stoppage, modification, and/or manual control of the movement of end-effector 112 and/or the surgical instrument 608. Thus, in use, in exemplary embodiments, a physician or other user can operate the system 100, and has the option to stop, modify, or manually control the autonomous movement of end-effector 112 and/or the surgical instrument 608. Further details of surgical robot system 100 including the control and movement of a surgical instrument 608 by surgical robot 102 can be found in co-pending U.S. patent application Ser. No. 13/924,505, which is incorporated herein by reference in its entirety.

The robotic surgical system 100 can comprise one or more tracking markers 118 configured to track the movement of robot arm 104, end-effector 112, patient 210, and/or the surgical instrument 608 in three dimensions. In exemplary embodiments, a plurality of tracking markers 118 can be mounted (or otherwise secured) thereon to an outer surface of the robot 102, such as, for example and without limitation, on base 106 of robot 102, on robot arm 104, or on the end-effector 112. In exemplary embodiments, at least one tracking marker 118 of the plurality of tracking markers 118 can be mounted or otherwise secured to the end-effector 112. One or more tracking markers 118 can further be mounted (or otherwise secured) to the patient 210. In exemplary embodiments, the plurality of tracking markers 118 can be positioned on the patient 210 spaced apart from the surgical field 208 to reduce the likelihood of being obscured by the surgeon, surgical tools, or other parts of the robot 102. Further, one or more tracking markers 118 can be further mounted (or otherwise secured) to the surgical tools 608 (e.g., a screw driver, dilator, implant inserter, or the like). Thus, the tracking markers 118 enable each of the marked objects (e.g., the end-effector 112, the patient 210, and the surgical tools 608) to be tracked by the robot 102. In exemplary embodiments, system 100 can use tracking information collected from each of the marked objects to calculate the orientation and location, for example, of the end-effector 112, the surgical instrument 608 (e.g., positioned in the tube 114 of the end-effector 112), and the relative position of the patient 210.

In exemplary embodiments, one or more of markers 118 may be optical markers. In some embodiments, the positioning of one or more tracking markers 118 on end-effector 112 can maximize the accuracy of the positional measurements by serving to check or verify the position of end-effector 112. Further details of surgical robot system 100 including the control, movement and tracking of surgical robot 102 and of a surgical instrument 608 can be found in co-pending U.S. patent application Ser. No. 13/924,505, which is incorporated herein by reference in its entirety.

Exemplary embodiments include one or more markers 118 coupled to the surgical instrument 608. In exemplary embodiments, these markers 118, for example, coupled to the patient 210 and surgical instruments 608, as well as markers 118 coupled to the end-effector 112 of the robot 102 can comprise conventional infrared light-emitting diodes (LEDs) or an Optotrak® diode capable of being tracked using a commercially available infrared optical tracking system such as Optotrak®. Optotrak® is a registered trademark of Northern Digital Inc., Waterloo, Ontario, Canada. In other embodiments, markers 118 can comprise conventional reflective spheres capable of being tracked using a commercially available optical tracking system such as Polaris Spectra. Polaris Spectra is also a registered trademark of Northern Digital, Inc. In an exemplary embodiment, the markers 118 coupled to the end-effector 112 are active markers which comprise infrared light-emitting diodes which may be turned on and off, and the markers 118 coupled to the patient 210 and the surgical instruments 608 comprise passive reflective spheres.

In exemplary embodiments, light emitted from and/or reflected by markers 118 can be detected by camera 200 and can be used to monitor the location and movement of the marked objects. In alternative embodiments, markers 118 can comprise a radio-frequency and/or electromagnetic reflector or transceiver and the camera 200 can include or be replaced by a radio-frequency and/or electromagnetic transceiver.

Similar to surgical robot system 100, FIG. 12 illustrates a surgical robot system 300 and camera stand 302, in a docked configuration, consistent with an exemplary embodiment of the present disclosure. Surgical robot system 300 may comprise a robot 301 including a display 304, upper arm 306, lower arm 308, end-effector 310, vertical column 312, casters 314, cabinet 316, tablet drawer 318, connector panel 320, control panel 322, and ring of information 324. Camera stand 302 may comprise camera 326. These components are described in greater with respect to FIG. 14. FIG. 12 illustrates the surgical robot system 300 in a docked configuration where the camera stand 302 is nested with the robot 301, for example, when not in use. It will be appreciated by those skilled in the art that the camera 326 and robot 301 may be separated from one another and positioned at any appropriate location during the surgical procedure, for example, as shown in FIGS. 10 and 11.

FIG. 13 illustrates a base 400 consistent with an exemplary embodiment of the present disclosure. Base 400 may be a portion of surgical robot system 300 and comprise cabinet 316. Cabinet 316 may house certain components of surgical robot system 300 including but not limited to a battery 402, a power distribution module 404, a platform interface board module 406, a computer 408, a handle 412, and a tablet drawer 414. The connections and relationship between these components is described in greater detail with respect to FIG. 14.

FIG. 14 illustrates a block diagram of certain components of an exemplary embodiment of surgical robot system 300. Surgical robot system 300 may comprise platform subsystem 502, computer subsystem 504, motion control subsystem 506, and tracking subsystem 532. Platform subsystem 502 may further comprise battery 402, power distribution module 404, platform interface board module 406, and tablet charging station 534. Computer subsystem 504 may further comprise computer 408, display 304, and speaker 536. Motion control subsystem 506 may further comprise driver circuit 508, motors 510, 512, 514, 516, 518, stabilizers 520, 522, 524, 526, end-effector 310, and controller 538. Tracking subsystem 532 may further comprise position sensor 540 and camera converter 542. System 300 may also comprise a foot pedal 544 and tablet 546.

Input power is supplied to system 300 via a power source 548 which may be provided to power distribution module 404. Power distribution module 404 receives input power and is configured to generate different power supply voltages that are provided to other modules, components, and subsystems of system 300. Power distribution module 404 may be configured to provide different voltage supplies to platform interface module 406, which may be provided to other components such as computer 408, display 304, speaker 536, driver 508 to, for example, power motors 512, 514, 516, 518 and end-effector 310, motor 510, ring 324, camera converter 542, and other components for system 300 for example, fans for cooling the electrical components within cabinet 316.

Power distribution module 404 may also provide power to other components such as tablet charging station 534 that may be located within tablet drawer 318. Tablet charging station 534 may be in wireless or wired communication with tablet 546 for charging table 546. Tablet 546 may be used by a surgeon consistent with the present disclosure and described herein.

Power distribution module 404 may also be connected to battery 402, which serves as temporary power source in the event that power distribution module 404 does not receive power from input power 548. At other times, power distribution module 404 may serve to charge battery 402 if necessary.

Other components of platform subsystem 502 may also include connector panel 320, control panel 322, and ring 324. Connector panel 320 may serve to connect different devices and components to system 300 and/or associated components and modules. Connector panel 320 may contain one or more ports that receive lines or connections from different components. For example, connector panel 320 may have a ground terminal port that may ground system 300 to other equipment, a port to connect foot pedal 544 to system 300, a port to connect to tracking subsystem 532, which may comprise position sensor 540, camera converter 542, and cameras 326 associated with camera stand 302. Connector panel 320 may also include other ports to allow USB, Ethernet, HDMI communications to other components, such as computer 408.

Control panel 322 may provide various buttons or indicators that control operation of system 300 and/or provide information regarding system 300. For example, control panel 322 may include buttons to power on or off system 300, lift or lower vertical column 312, and lift or lower stabilizers 520-526 that may be designed to engage casters 314 to lock system 300 from physically moving. Other buttons may stop system 300 in the event of an emergency, which may remove all motor power and apply mechanical brakes to stop all motion from occurring. Control panel 322 may also have indicators notifying the user of certain system conditions such as a line power indicator or status of charge for battery 402.

Ring 324 may be a visual indicator to notify the user of system 300 of different modes that system 300 is operating under and certain warnings to the user.

Computer subsystem 504 includes computer 408, display 304, and speaker 536. Computer 504 includes an operating system and software to operate system 300. Computer 504 may receive and process information from other components (for example, tracking subsystem 532, platform subsystem 502, and/or motion control subsystem 506) in order to display information to the user. Further, computer subsystem 504 may also include speaker 536 to provide audio to the user.

Tracking subsystem 532 may include position sensor 504 and converter 542. Tracking subsystem 532 may correspond to camera stand 302 including camera 326 as described with respect to FIG. 12. Position sensor 504 may be camera 326. Tracking subsystem may track the location of certain markers that are located on the different components of system 300 and/or instruments used by a user during a surgical procedure. This tracking may be conducted in a manner consistent with the present disclosure including the use of infrared technology that tracks the location of active or passive elements, such as LEDs or reflective markers, respectively. The location, orientation, and position of structures having these types of markers may be provided to computer 408 which may be shown to a user on display 304. For example, a surgical instrument 608 having these types of markers and tracked in this manner (which may be referred to as a navigational space) may be shown to a user in relation to a three dimensional image of a patient's anatomical structure.

Motion control subsystem 506 may be configured to physically move vertical column 312, upper arm 306, lower arm 308, or rotate end-effector 310. The physical movement may be conducted through the use of one or more motors 510-518. For example, motor 510 may be configured to vertically lift or lower vertical column 312. Motor 512 may be configured to laterally move upper arm 308 around a point of engagement with vertical column 312 as shown in FIG. 12. Motor 514 may be configured to laterally move lower arm 308 around a point of engagement with upper arm 308 as shown in FIG. 12. Motors 516 and 518 may be configured to move end-effector 310 in a manner such that one may control the roll and one may control the tilt, thereby providing multiple angles that end-effector 310 may be moved. These movements may be achieved by controller 538 which may control these movements through load cells disposed on end-effector 310 and activated by a user engaging these load cells to move system 300 in a desired manner.

Moreover, system 300 may provide for automatic movement of vertical column 312, upper arm 306, and lower arm 308 through a user indicating on display 304 (which may be a touchscreen input device) the location of a surgical instrument or component on three dimensional image of the patient's anatomy on display 304. The user may initiate this automatic movement by stepping on foot pedal 544 or some other input means.

FIG. 15 illustrates a surgical robot system 600 consistent with an exemplary embodiment. Surgical robot system 600 may comprise end-effector 602, robot arm 604, guide tube 606, instrument 608, and robot base 610. Instrument tool 608 may be attached to a tracking array 612 including one or more tracking markers (such as markers 118) and have an associated trajectory 614. Trajectory 614 may represent a path of movement that instrument tool 608 is configured to travel once it is positioned through or secured in guide tube 606, for example, a path of insertion of instrument tool 608 into a patient. In an exemplary operation, robot base 610 may be configured to be in electronic communication with robot arm 604 and end-effector 602 so that surgical robot system 600 may assist a user (for example, a surgeon) in operating on the patient 210. Surgical robot system 600 may be consistent with previously described surgical robot system 100 and 300.

A tracking array 612 may be mounted on instrument 608 to monitor the location and orientation of instrument tool 608. The tracking array 612 may be attached to an instrument 608 and may comprise tracking markers 804. As best seen in FIG. 17, tracking markers 804 may be, for example, light emitting diodes and/or other types of reflective markers (e.g., markers 118 as described elsewhere herein). The tracking devices may be one or more line of sight devices associated with the surgical robot system. As an example, the tracking devices may be one or more cameras 200, 326 associated with the surgical robot system 100, 300 and may also track tracking array 612 for a defined domain or relative orientations of the instrument 608 in relation to the robot arm 604, the robot base 610, end-effector 602, and/or the patient 210. The tracking devices may be consistent with those structures described in connection with camera stand 302 and tracking subsystem 532.

FIGS. 16A, 16B, and 16C illustrate a top view, front view, and side view, respectively, of end-effector 602 consistent with an exemplary embodiment. End-effector 602 may comprise one or more tracking markers 702. Tracking markers 702 may be light emitting diodes or other types of active and passive markers, such as tracking markers 118 that have been previously described. In an exemplary embodiment, the tracking markers 702 are active infrared-emitting markers that are activated by an electrical signal (e.g., infrared light emitting diodes (LEDs)). Thus, tracking markers 702 may be activated such that the infrared markers 702 are visible to the camera 200, 326 or may be deactivated such that the infrared markers 702 are not visible to the camera 200, 326. Thus, when the markers 702 are active, the end-effector 602 may be controlled by the system 100, 300, 600, and when the markers 702 are deactivated, the end-effector 602 may be locked in position and unable to be moved by the system 100, 300, 600.

Markers 702 may be disposed on or within end-effector 602 in a manner such that the markers 702 are visible by one or more cameras 200, 326 or other tracking devices associated with the surgical robot system 100, 300, 600. The camera 200, 326 or other tracking devices may track end-effector 602 as it moves to different positions and viewing angles by following the movement of tracking markers 702. The location of markers 702 and/or end-effector 602 may be shown on a display 110, 304 associated with the surgical robot system 100, 300, 600, for example, display 110 as shown in FIG. 11 and/or display 304 shown in FIG. 12. This display 110, 304 may allow a user to ensure that end-effector 602 is in a desirable position in relation to robot arm 604, robot base 610, the patient 210, and/or the user.

For example, as shown in FIG. 16A, markers 702 may be placed around the surface of end-effector 602 so that a tracking device placed away from the surgical field 208 and facing toward the robot 102, 301 and the camera 200, 326 is able to view at least 3 of the markers 702 through a range of common orientations of the end-effector 602 relative to the tracking device 100, 300, 600. For example, distribution of markers 702 in this way allows end-effector 602 to be monitored by the tracking devices when end-effector 602 is translated and rotated in the surgical field 208.

In addition, in exemplary embodiments, end-effector 602 may be equipped with infrared (IR) receivers that can detect when an external camera 200, 326 is getting ready to read markers 702. Upon this detection, end-effector 602 may then illuminate markers 702. The detection by the IR receivers that the external camera 200, 326 is ready to read markers 702 may signal the need to synchronize a duty cycle of markers 702, which may be light emitting diodes, to an external camera 200, 326. This may also allow for lower power consumption by the robotic system as a whole, whereby markers 702 would only be illuminated at the appropriate time instead of being illuminated continuously. Further, in exemplary embodiments, markers 702 may be powered off to prevent interference with other navigation tools, such as different types of surgical instruments 608.

FIG. 17 depicts one type of surgical instrument 608 including a tracking array 612 and tracking markers 804. Tracking markers 804 may be of any type described herein including but not limited to light emitting diodes or reflective spheres. Markers 804 are monitored by tracking devices associated with the surgical robot system 100, 300, 600 and may be one or more of the line of sight cameras 200, 326. The cameras 200, 326 may track the location of instrument 608 based on the position and orientation of tracking array 612 and markers 804. A user, such as a surgeon 120, may orient instrument 608 in a manner so that tracking array 612 and markers 804 are sufficiently recognized by the tracking device or camera 200, 326 to display instrument 608 and markers 804 on, for example, display 110 of the exemplary surgical robot system.

The manner in which a surgeon 120 may place instrument 608 into guide tube 606 of the end-effector 602 and adjust the instrument 608 is evident in FIG. 17. The hollow tube or guide tube 114, 606 of the end-effector 112, 310, 602 is sized and configured to receive at least a portion of the surgical instrument 608. The guide tube 114, 606 is configured to be oriented by the robot arm 104 such that insertion and trajectory for the surgical instrument 608 is able to reach a desired anatomical target within or upon the body of the patient 210. The surgical instrument 608 may include at least a portion of a generally cylindrical instrument. Although a screw driver is exemplified as the surgical tool 608, it will be appreciated that any suitable surgical tool 608 may be positioned by the end-effector 602. By way of example, the surgical instrument 608 may include one or more of a guide wire, cannula, a retractor, a drill, a reamer, a screw driver, an insertion tool, a removal tool, or the like. Although the hollow tube 114, 606 is generally shown as having a cylindrical configuration, it will be appreciated by those of skill in the art that the guide tube 114, 606 may have any suitable shape, size and configuration desired to accommodate the surgical instrument 608 and access the surgical site.

FIGS. 18A-18C illustrate end-effector 602 and a portion of robot arm 604 consistent with an exemplary embodiment. End-effector 602 may further comprise body 1202 and clamp 1204. Clamp 1204 may comprise handle 1206, balls 1208, spring 1210, and lip 1212. Robot arm 604 may further comprise depressions 1214, mounting plate 1216, lip 1218, and magnets 1220.

End-effector 602 may mechanically interface and/or engage with the surgical robot system and robot arm 604 through one or more couplings. For example, end-effector 602 may engage with robot arm 604 through a locating coupling and/or a reinforcing coupling. Through these couplings, end-effector 602 may fasten with robot arm 604 outside a flexible and sterile barrier. In an exemplary embodiment, the locating coupling may be a magnetically kinematic mount and the reinforcing coupling may be a five bar over center clamping linkage.

With respect to the locating coupling, robot arm 604 may comprise mounting plate 1216, which may be non-magnetic material, one or more depressions 1214, lip 1218, and magnets 1220. Magnet 1220 is mounted below each of depressions 1214. Portions of clamp 1204 may comprise magnetic material and be attracted by one or more magnets 1220. Through the magnetic attraction of clamp 1204 and robot arm 604, balls 1208 become seated into respective depressions 1214. For example, balls 1208 as shown in FIG. 18B would be seated in depressions 1214 as shown in FIG. 18A. This seating may be considered a magnetically-assisted kinematic coupling. Magnets 1220 may be configured to be strong enough to support the entire weight of end-effector 602 regardless of the orientation of end-effector 602. The locating coupling may be any style of kinematic mount that uniquely restrains six degrees of freedom.

With respect to the reinforcing coupling, portions of clamp 1204 may be configured to be a fixed ground link and as such clamp 1204 may serve as a five bar linkage. Closing clamp handle 1206 may fasten end-effector 602 to robot arm 604 as lip 1212 and lip 1218 engage clamp 1204 in a manner to secure end-effector 602 and robot arm 604. When clamp handle 1206 is closed, spring 1210 may be stretched or stressed while clamp 1204 is in a locked position. The locked position may be a position that provides for linkage past center. Because of a closed position that is past center, the linkage will not open absent a force applied to clamp handle 1206 to release clamp 1204. Thus, in a locked position end-effector 602 may be robustly secured to robot arm 604.

Spring 1210 may be a curved beam in tension. Spring 1210 may be comprised of a material that exhibits high stiffness and high yield strain such as virgin PEEK (poly-ether-ether-ketone). The linkage between end-effector 602 and robot arm 604 may provide for a sterile barrier between end-effector 602 and robot arm 604 without impeding fastening of the two couplings.

The reinforcing coupling may be a linkage with multiple spring members. The reinforcing coupling may latch with a cam or friction based mechanism. The reinforcing coupling may also be a sufficiently powerful electromagnet that will support fastening end-effector 102 to robot arm 604. The reinforcing coupling may be a multi-piece collar completely separate from either end-effector 602 and/or robot arm 604 that slips over an interface between end-effector 602 and robot arm 604 and tightens with a screw mechanism, an over center linkage, or a cam mechanism.

Referring to FIGS. 10 and 11, prior to or during a surgical procedure, certain registration procedures may be conducted in order to track objects and a target anatomical structure of the patient 210 both in a navigation space and an image space. In order to conduct such registration, a registration system 1400 may be used as illustrated in FIG. 19.

In order to track the position of the patient 210, a patient tracking device 116 may include a patient fixation instrument 1402 to be secured to a rigid anatomical structure of the patient 210 and a dynamic reference base (DRB) 1404 may be securely attached to the patient fixation instrument 1402. For example, patient fixation instrument 1402 may be inserted into opening 1406 of dynamic reference base 1404. Dynamic reference base 1404 may contain markers 1408 that are visible to tracking devices, such as tracking subsystem 532. These markers 1408 may be optical markers or reflective spheres, such as tracking markers 118, as previously discussed herein.

Patient fixation instrument 1402 is attached to a rigid anatomy of the patient 210 and may remain attached throughout the surgical procedure. In an exemplary embodiment, patient fixation instrument 1402 is attached to a rigid area of the patient 210, for example, a bone that is located away from the targeted anatomical structure subject to the surgical procedure. In order to track the targeted anatomical structure, dynamic reference base 1404 is associated with the targeted anatomical structure through the use of a registration fixture that is temporarily placed on or near the targeted anatomical structure in order to register the dynamic reference base 1404 with the location of the targeted anatomical structure.

A registration fixture 1410 is attached to patient fixation instrument 1402 through the use of a pivot arm 1412. Pivot arm 1412 is attached to patient fixation instrument 1402 by inserting patient fixation instrument 1402 through an opening 1414 of registration fixture 1410. Pivot arm 1412 is attached to registration fixture 1410 by, for example, inserting a knob 1416 through an opening 1418 of pivot arm 1412.

Using pivot arm 1412, registration fixture 1410 may be placed over the targeted anatomical structure and its location may be determined in an image space and navigation space using tracking markers 1420 and/or fiducials 1422 on registration fixture 1410. Registration fixture 1410 may contain a collection of markers 1420 that are visible in a navigational space (for example, markers 1420 may be detectable by tracking subsystem 532). Tracking markers 1420 may be optical markers visible in infrared light as previously described herein. Registration fixture 1410 may also contain a collection of fiducials 1422, for example, such as bearing balls, that are visible in an imaging space (for example, a three dimension CT image). As described in greater detail with respect to FIG. 20, using registration fixture 1410, the targeted anatomical structure may be associated with dynamic reference base 1404 thereby allowing depictions of objects in the navigational space to be overlaid on images of the anatomical structure. Dynamic reference base 1404, located at a position away from the targeted anatomical structure, may become a reference point thereby allowing removal of registration fixture 1410 and/or pivot arm 1412 from the surgical area.

FIG. 20 provides an exemplary method 1500 for registration consistent with the present disclosure. Method 1500 begins at step 1502 wherein a graphical representation (or image(s)) of the targeted anatomical structure may be imported into system 100, 300 600, for example computer 408. The graphical representation may be three dimensional CT or a fluoroscope scan of the targeted anatomical structure of the patient 210 which includes registration fixture 1410 and a detectable imaging pattern of fiducials 1420.

At step 1504, an imaging pattern of fiducials 1420 is detected and registered in the imaging space and stored in computer 408. Optionally, at this time at step 1506, a graphical representation of the registration fixture 1410 may be overlaid on the images of the targeted anatomical structure.

At step 1508, a navigational pattern of registration fixture 1410 is detected and registered by recognizing markers 1420. Markers 1420 may be optical markers that are recognized in the navigation space through infrared light by tracking subsystem 532 via position sensor 540. Thus, the location, orientation, and other information of the targeted anatomical structure is registered in the navigation space. Therefore, registration fixture 1410 may be recognized in both the image space through the use of fiducials 1422 and the navigation space through the use of markers 1420. At step 1510, the registration of registration fixture 1410 in the image space is transferred to the navigation space. This transferal is done, for example, by using the relative position of the imaging pattern of fiducials 1422 compared to the position of the navigation pattern of markers 1420.

At step 1512, registration of the navigation space of registration fixture 1410 (having been registered with the image space) is further transferred to the navigation space of dynamic registration array 1404 attached to patient fixture instrument 1402. Thus, registration fixture 1410 may be removed and dynamic reference base 1404 may be used to track the targeted anatomical structure in both the navigation and image space because the navigation space is associated with the image space.

At steps 1514 and 1516, the navigation space may be overlaid on the image space and objects with markers visible in the navigation space (for example, surgical instruments 608 with optical markers 804). The objects may be tracked through graphical representations of the surgical instrument 608 on the images of the targeted anatomical structure.

FIGS. 21A-21B illustrate imaging devices 1304 that may be used in conjunction with robot systems 100, 300, 600 to acquire pre-operative, intra-operative, post-operative, and/or real-time image data of patient 210. Any appropriate subject matter may be imaged for any appropriate procedure using the imaging system 1304. The imaging system 1304 may be any imaging device such as imaging device 1306 and/or a C-arm 1308 device. It may be desirable to take x-rays of patient 210 from a number of different positions, without the need for frequent manual repositioning of patient 210 which may be required in an x-ray system. As illustrated in FIG. 21A, the imaging system 1304 may be in the form of a C-arm 1308 that includes an elongated C-shaped member terminating in opposing distal ends 1312 of the "C" shape. C-shaped member 1130 may further comprise an x-ray source 1314 and an image receptor 1316. The space within C-arm 1308 of the arm may provide room for the physician to attend to the patient substantially free of interference from x-ray support structure 1318. As illustrated in FIG. 21B, the imaging system may include imaging device 1306 having a gantry housing 1324 attached to a support structure imaging device support structure 1328, such as a wheeled mobile cart 1330 with wheels 1332, which may enclose an image capturing portion, not illustrated. The image capturing portion may include an x-ray source and/or emission portion and an x-ray receiving and/or image receiving portion, which may be disposed about one hundred and eighty degrees from each other and mounted on a rotor (not illustrated) relative to a track of the image capturing portion. The image capturing portion may be operable to rotate three hundred and sixty degrees during image acquisition. The image capturing portion may rotate around a central point and/or axis, allowing image data of patient 210 to be acquired from multiple directions or in multiple planes. Although certain imaging systems 1304 are exemplified herein, it will be appreciated that any suitable imaging system may be selected by one of ordinary skill in the art.

Turning now to FIGS. 22A-22C, the surgical robot system 100, 300, 600 relies on accurate positioning of the end-effector 112, 602, surgical instruments 608, and/or the patient 210 (e.g., patient tracking device 116) relative to the desired surgical area. In the embodiments shown in FIGS. 22A-22C, the tracking markers 118, 804 are rigidly attached to a portion of the instrument 608 and/or end-effector 112.

FIG. 22A depicts part of the surgical robot system 100 with the robot 102 including base 106, robot arm 104, and end-effector 112. The other elements, not illustrated, such as the display, cameras, etc. may also be present as described herein. FIG. 22B depicts a close-up view of the end-effector 112 with guide tube 114 and a plurality of tracking markers 118 rigidly affixed to the end-effector 112. In this embodiment, the plurality of tracking markers 118 are attached to the guide tube 112. FIG. 22C depicts an instrument 608 (in this case, a probe 608A) with a plurality of tracking markers 804 rigidly affixed to the instrument 608. As described elsewhere herein, the instrument 608 could include any suitable surgical instrument, such as, but not limited to, guide wire, cannula, a retractor, a drill, a reamer, a screw driver, an insertion tool, a removal tool, or the like.

When tracking an instrument 608, end-effector 112, or other object to be tracked in 3D, an array of tracking markers 118, 804 may be rigidly attached to a portion of the tool 608 or end-effector 112. Preferably, the tracking markers 118, 804 are attached such that the markers 118, 804 are out of the way (e.g., not impeding the surgical operation, visibility, etc.). The markers 118, 804 may be affixed to the instrument 608, end-effector 112, or other object to be tracked, for example, with an array 612. Usually three or four markers 118, 804 are used with an array 612. The array 612 may include a linear section, a cross piece, and may be asymmetric such that the markers 118, 804 are at different relative positions and locations with respect to one another. For example, as shown in FIG. 22C, a probe 608A with a 4-marker tracking array 612 is shown, and FIG. 22B depicts the end-effector 112 with a different 4-marker tracking array 612.

In FIG. 22C, the tracking array 612 functions as the handle 620 of the probe 608A. Thus, the four markers 804 are attached to the handle 620 of the probe 608A, which is out of the way of the shaft 622 and tip 624. Stereophotogrammetric tracking of these four markers 804 allows the instrument 608 to be tracked as a rigid body and for the tracking system 100, 300, 600 to precisely determine the position of the tip 624 and the orientation of the shaft 622 while the probe 608A is moved around in front of tracking cameras 200, 326.

To enable automatic tracking of one or more tools 608, end-effector 112, or other object to be tracked in 3D (e.g., multiple rigid bodies), the markers 118, 804 on each tool 608, end-effector 112, or the like, are arranged asymmetrically with a known inter-marker spacing. The reason for asymmetric alignment is so that it is unambiguous which marker 118, 804 corresponds to a particular location on the rigid body and whether markers 118, 804 are being viewed from the front or back, i.e., mirrored. For example, if the markers 118, 804 were arranged in a square on the tool 608 or end-effector 112, it would be unclear to the system 100, 300, 600 which marker 118, 804 corresponded to which corner of the square. For example, for the probe 608A, it would be unclear which marker 804 was closest to the shaft 622. Thus, it would be unknown which way the shaft 622 was extending from the array 612. Accordingly, each array 612 and thus each tool 608, end-effector 112, or other object to be tracked should have a unique marker pattern to allow it to be distinguished from other tools 608 or other objects being tracked. Asymmetry and unique marker patterns allow the system 100, 300, 600 to detect individual markers 118, 804 then to check the marker spacing against a stored template to determine which tool 608, end effector 112, or other object they represent. Detected markers 118, 804 can then be sorted automatically and assigned to each tracked object in the correct order. Without this information, rigid body calculations could not then be performed to extract key geometric information, for example, such as tool tip 624 and alignment of the shaft 622, unless the user manually specified which detected marker 118, 804 corresponded to which position on each rigid body. These concepts are commonly known to those skilled in the methods of 3D optical tracking.

Turning now to FIGS. 23A-23D, an alternative version of an end-effector 912 with moveable tracking markers 918A-918D is shown. In FIG. 23A, an array with moveable tracking markers 918A-918D are shown in a first configuration, and in FIG. 23B the moveable tracking markers 918A-918D are shown in a second configuration, which is angled relative to the first configuration. FIG. 23C shows the template of the tracking markers 918A-918D, for example, as seen by the cameras 200, 326 in the first configuration of FIG. 23A; and FIG. 23D shows the template of tracking markers 918A-918D, for example, as seen by the cameras 200, 326 in the second configuration of FIG. 23B.

In this embodiment, 4-marker array tracking is contemplated wherein the markers 918A-918D are not all in fixed position relative to the rigid body and instead, one or more of the array markers 918A-918D can be adjusted, for example, during testing, to give updated information about the rigid body that is being tracked without disrupting the process for automatic detection and sorting of the tracked markers 918A-918D.

When tracking any tool, such as a guide tube 914 connected to the end effector 912 of a robot system 100, 300, 600, the tracking array's primary purpose is to update the position of the end effector 912 in the camera coordinate system. When using the rigid system, for example, as shown in FIG. 22B, the array 612 of reflective markers 118 rigidly extend from the guide tube 114. Because the tracking markers 118 are rigidly connected, knowledge of the marker locations in the camera coordinate system also provides exact location of the centerline, tip, and tail of the guide tube 114 in the camera coordinate system. Typically, information about the position of the end effector 112 from such an array 612 and information about the location of a target trajectory from another tracked source are used to calculate the required moves that must be input for each axis of the robot 102 that will move the guide tube 114 into alignment with the trajectory and move the tip to a particular location along the trajectory vector.

Sometimes, the desired trajectory is in an awkward or unreachable location, but if the guide tube 114 could be swiveled, it could be reached. For example, a very steep trajectory pointing away from the base 106 of the robot 102 might be reachable if the guide tube 114 could be swiveled upward beyond the limit of the pitch (wrist up-down angle) axis, but might not be reachable if the guide tube 114 is attached parallel to the plate connecting it to the end of the wrist. To reach such a trajectory, the base 106 of the robot 102 might be moved or a different end effector 112 with a different guide tube attachment might be exchanged with the working end effector. Both of these solutions may be time consuming and cumbersome.

As best seen in FIGS. 23A and 23B, if the array 908 is configured such that one or more of the markers 918A-918D are not in a fixed position and instead, one or more of the markers 918A-918D can be adjusted, swiveled, pivoted, or moved, the robot 102 can provide updated information about the object being tracked without disrupting the detection and tracking process. For example, one of the markers 918A-918D may be fixed in position and the other markers 918A-918D may be moveable; two of the markers 918A-918D may be fixed in position and the other markers 918A-918D may be moveable; three of the markers 918A-918D may be fixed in position and the other marker 918A-918D may be moveable; or all of the markers 918A-918D may be moveable.

In the embodiment shown in FIGS. 23A and 23B, markers 918A, 918 B are rigidly connected directly to a base 906 of the end-effector 912, and markers 918C, 918D are rigidly connected to the tube 914. Similar to array 612, array 908 may be provided to attach the markers 918A-918D to the end-effector 912, instrument 608, or other object to be tracked. In this case, however, the array 908 is comprised of a plurality of separate components. For example, markers 918A, 918B may be connected to the base 906 with a first array 908A, and markers 918C, 918D may be connected to the guide tube 914 with a second array 908B. Marker 918A may be affixed to a first end of the first array 908A and marker 918B may be separated a linear distance and affixed to a second end of the first array 908A. While first array 908 is substantially linear, second array 908B has a bent or V-shaped configuration, with respective root ends, connected to the guide tube 914, and diverging therefrom to distal ends in a V-shape with marker 918C at one distal end and marker 918D at the other distal end. Although specific configurations are exemplified herein, it will be appreciated that other asymmetric designs including different numbers and types of arrays 908A, 908B and different arrangements, numbers, and types of markers 918A-918D are contemplated.

The guide tube 914 may be moveable, swivelable, or pivotable relative to the base 906, for example, across a hinge 920 or other connector to the base 906. Thus, markers 918C, 918D are moveable such that when the guide tube 914 pivots, swivels, or moves, markers 918C, 918D also pivot, swivel, or move. As best seen in FIG. 23A, guide tube 914 has a longitudinal axis 916 which is aligned in a substantially normal or vertical orientation such that markers 918A-918D have a first configuration. Turning now to FIG. 23B, the guide tube 914 is pivoted, swiveled, or moved such that the longitudinal axis 916 is now angled relative to the vertical orientation such that markers 918A-918D have a second configuration, different from the first configuration.

In contrast to the embodiment described for FIGS. 23A-23D, if a swivel existed between the guide tube 914 and the arm 104 (e.g., the wrist attachment) with all four markers 918A-918D remaining attached rigidly to the guide tube 914 and this swivel was adjusted by the user, the robotic system 100, 300, 600 would not be able to automatically detect that the guide tube 914 orientation had changed. The robotic system 100, 300, 600 would track the positions of the marker array 908 and would calculate incorrect robot axis moves assuming the guide tube 914 was attached to the wrist (the robot arm 104) in the previous orientation. By keeping one or more markers 918A-918D (e.g., two markers 918C, 918D) rigidly on the tube 914 and one or more markers 918A-918D (e.g., two markers 918A, 918B) across the swivel, automatic detection of the new position becomes possible and correct robot moves are calculated based on the detection of a new tool or end-effector 112, 912 on the end of the robot arm 104.

One or more of the markers 918A-918D are configured to be moved, pivoted, swiveled, or the like according to any suitable means. For example, the markers 918A-918D may be moved by a hinge 920, such as a clamp, spring, lever, slide, toggle, or the like, or any other suitable mechanism for moving the markers 918A-918D individually or in combination, moving the arrays 908A, 908B individually or in combination, moving any portion of the end-effector 912 relative to another portion, or moving any portion of the tool 608 relative to another portion.

As shown in FIGS. 23A and 23B, the array 908 and guide tube 914 may become reconfigurable by simply loosening the clamp or hinge 920, moving part of the array 908A, 908B relative to the other part 908A, 908B, and retightening the hinge 920 such that the guide tube 914 is oriented in a different position. For example, two markers 918C, 918D may be rigidly interconnected with the tube 914 and two markers 918A, 918B may be rigidly interconnected across the hinge 920 to the base 906 of the end-effector 912 that attaches to the robot arm 104. The hinge 920 may be in the form of a clamp, such as a wing nut or the like, which can be loosened and retightened to allow the user to quickly switch between the first configuration (FIG. 23A) and the second configuration (FIG. 23B).

The cameras 200, 326 detect the markers 918A-918D, for example, in one of the templates identified in FIGS. 23C and 23D. If the array 908 is in the first configuration (FIG. 23A) and tracking cameras 200, 326 detect the markers 918A-918D, then the tracked markers match Array Template 1 as shown in FIG. 23C. If the array 908 is the second configuration (FIG. 23B) and tracking cameras 200, 326 detect the same markers 918A-918D, then the tracked markers match Array Template 2 as shown in FIG. 23D. Array Template 1 and Array Template 2 are recognized by the system 100, 300, 600 as two distinct tools, each with its own uniquely defined spatial relationship between guide tube 914, markers 918A-918D, and robot attachment. The user could therefore adjust the position of the end-effector 912 between the first and second configurations without notifying the system 100, 300, 600 of the change and the system 100, 300, 600 would appropriately adjust the movements of the robot 102 to stay on trajectory.

In this embodiment, there are two assembly positions in which the marker array matches unique templates that allow the system 100, 300, 600 to recognize the assembly as two different tools or two different end effectors. In any position of the swivel between or outside of these two positions (namely, Array Template 1 and Array Template 2 shown in FIGS. 23C and 23D, respectively), the markers 918A-918D would not match any template and the system 100, 300, 600 would not detect any array present despite individual markers 918A-918D being detected by cameras 200, 326, with the result being the same as if the markers 918A-918D were temporarily blocked from view of the cameras 200, 326. It will be appreciated that other array templates may exist for other configurations, for example, identifying different instruments 608 or other end-effectors 112, 912, etc.

In the embodiment described, two discrete assembly positions are shown in FIGS. 23A and 23B. It will be appreciated, however, that there could be multiple discrete positions on a swivel joint, linear joint, combination of swivel and linear joints, pegboard, or other assembly where unique marker templates may be created by adjusting the position of one or more markers 918A-918D of the array relative to the others, with each discrete position matching a particular template and defining a unique tool 608 or end-effector 112, 912 with different known attributes. In addition, although exemplified for end effector 912, it will be appreciated that moveable and fixed markers 918A-918D may be used with any suitable instrument 608 or other object to be tracked.

When using an external 3D tracking system 100, 300, 600 to track a full rigid body array of three or more markers attached to a robot's end effector 112 (for example, as depicted in FIGS. 22A and 22B), it is possible to directly track or to calculate the 3D position of every section of the robot 102 in the coordinate system of the cameras 200, 326. The geometric orientations of joints relative to the tracker are known by design, and the linear or angular positions of joints are known from encoders for each motor of the robot 102, fully defining the 3D positions of all of the moving parts from the end effector 112 to the base 116. Similarly, if a tracker were mounted on the base 106 of the robot 102 (not shown), it is likewise possible to track or calculate the 3D position of every section of the robot 102 from base 106 to end effector 112 based on known joint geometry and joint positions from each motor's encoder.

In some situations, it may be desirable to track the positions of all segments of the robot 102 from fewer than three markers 118 rigidly attached to the end effector 112. Specifically, if a tool 608 is introduced into the guide tube 114, it may be desirable to track full rigid body motion of the robot 902 with only one additional marker 118 being tracked.

Turning now to FIGS. 24A-24E, an alternative version of an end-effector 1012 having only a single tracking marker 1018 is shown. End-effector 1012 may be similar to the other end-effectors described herein, and may include a guide tube 1014 extending along a longitudinal axis 1016. A single tracking marker 1018, similar to the other tracking markers described herein, may be rigidly affixed to the guide tube 1014. This single marker 1018 can serve the purpose of adding missing degrees of freedom to allow full rigid body tracking and/or can serve the purpose of acting as a surveillance marker to ensure that assumptions about robot and camera positioning are valid.

The single tracking marker 1018 may be attached to the robotic end effector 1012 as a rigid extension to the end effector 1012 that protrudes in any convenient direction and does not obstruct the surgeon's view. The tracking marker 1018 may be affixed to the guide tube 1014 or any other suitable location of on the end-effector 1012. When affixed to the guide tube 1014, the tracking marker 1018 may be positioned at a location between first and second ends of the guide tube 1014. For example, in FIG. 24A, the single tracking marker 1018 is shown as a reflective sphere mounted on the end of a narrow shaft 1017 that extends forward from the guide tube 1014 and is positioned longitudinally above a mid-point of the guide tube 1014 and below the entry of the guide tube 1014. This position allows the marker 1018 to be generally visible by cameras 200, 326 but also would not obstruct vision of the surgeon 120 or collide with other tools or objects in the vicinity of surgery. In addition, the guide tube 1014 with the marker 1018 in this position is designed for the marker array on any tool 608 introduced into the guide tube 1014 to be visible at the same time as the single marker 1018 on the guide tube 1014 is visible.

As shown in FIG. 24B, when a snugly fitting tool or instrument 608 is placed within the guide tube 1014, the instrument 608 becomes mechanically constrained in 4 of 6 degrees of freedom. That is, the instrument 608 cannot be rotated in any direction except about the longitudinal axis 1016 of the guide tube 1014 and the instrument 608 cannot be translated in any direction except along the longitudinal axis 1016 of the guide tube 1014. In other words, the instrument 608 can only be translated along and rotated about the centerline of the guide tube 1014. If two more parameters are known, such as (1) an angle of rotation about the longitudinal axis 1016 of the guide tube 1014; and (2) a position along the guide tube 1014, then the position of the end effector 1012 in the camera coordinate system becomes fully defined.

Referring now to FIG. 24C, the system 100, 300, 600 should be able to know when a tool 608 is actually positioned inside of the guide tube 1014 and is not instead outside of the guide tube 1014 and just somewhere in view of the cameras 200, 326. The tool 608 has a longitudinal axis or centerline 616 and an array 612 with a plurality of tracked markers 804. The rigid body calculations may be used to determine where the centerline 616 of the tool 608 is located in the camera coordinate system based on the tracked position of the array 612 on the tool 608.

The fixed normal (perpendicular) distance DF from the single marker 1018 to the centerline or longitudinal axis 1016 of the guide tube 1014 is fixed and is known geometrically, and the position of the single marker 1018 can be tracked. Therefore, when a detected distance DD from tool centerline 616 to single marker 1018 matches the known fixed distance DF from the guide tube centerline 1016 to the single marker 1018, it can be determined that the tool 608 is either within the guide tube 1014 (centerlines 616, 1016 of tool 608 and guide tube 1014 coincident) or happens to be at some point in the locus of possible positions where this distance DD matches the fixed distance DF. For example, in FIG. 24C, the normal detected distance DD from tool centerline 616 to the single marker 1018 matches the fixed distance DF from guide tube centerline 1016 to the single marker 1018 in both frames of data (tracked marker coordinates) represented by the transparent tool 608 in two positions, and thus, additional considerations may be needed to determine when the tool 608 is located in the guide tube 1014.

Turning now to FIG. 24D, programmed logic can be used to look for frames of tracking data in which the detected distance DD from tool centerline 616 to single marker 1018 remains fixed at the correct length despite the tool 608 moving in space by more than some minimum distance relative to the single sphere 1018 to satisfy the condition that the tool 608 is moving within the guide tube 1014. For example, a first frame F1 may be detected with the tool 608 in a first position and a second frame F2 may be detected with the tool 608 in a second position (namely, moved linearly with respect to the first position). The markers 804 on the tool array 612 may move by more than a given amount (e.g., more than 5 mm total) from the first frame F1 to the second frame F2. Even with this movement, the detected distance DD from the tool centerline vector C' to the single marker 1018 is substantially identical in both the first frame F1 and the second frame F2.

Logistically, the surgeon 120 or user could place the tool 608 within the guide tube 1014 and slightly rotate it or slide it down into the guide tube 1014 and the system 100, 300, 600 would be able to detect that the tool 608 is within the guide tube 1014 from tracking of the five markers (four markers 804 on tool 608 plus single marker 1018 on guide tube 1014). Knowing that the tool 608 is within the guide tube 1014, all 6 degrees of freedom may be calculated that define the position and orientation of the robotic end effector 1012 in space. Without the single marker 1018, even if it is known with certainty that the tool 608 is within the guide tube 1014, it is unknown where the guide tube 1014 is located along the tool's centerline vector C' and how the guide tube 1014 is rotated relative to the centerline vector C'.

With emphasis on FIG. 24E, the presence of the single marker 1018 being tracked as well as the four markers 804 on the tool 608, it is possible to construct the centerline vector C' of the guide tube 1014 and tool 608 and the normal vector through the single marker 1018 and through the centerline vector C'. This normal vector has an orientation that is in a known orientation relative to the forearm of the robot distal to the wrist (in this example, oriented parallel to that segment) and intersects the centerline vector C' at a specific fixed position. For convenience, three mutually orthogonal vectors k', j', i' can be constructed, as shown in FIG. 24E, defining rigid body position and orientation of the guide tube 1014. One of the three mutually orthogonal vectors k' is constructed from the centerline vector C', the second vector j' is constructed from the normal vector through the single marker 1018, and the third vector i' is the vector cross product of the first and second vectors k', j'. The robot's joint positions relative to these vectors k', j', i' are known and fixed when all joints are at zero, and therefore rigid body calculations can be used to determine the location of any section of the robot relative to these vectors k', j', i' when the robot is at a home position. During robot movement, if the positions of the tool markers 804 (while the tool 608 is in the guide tube 1014) and the position of the single marker 1018 are detected from the tracking system, and angles/linear positions of each joint are known from encoders, then position and orientation of any section of the robot can be determined.

In some embodiments, it may be useful to fix the orientation of the tool 608 relative to the guide tube 1014. For example, the end effector guide tube 1014 may be oriented in a particular position about its axis 1016 to allow machining or implant positioning. Although the orientation of anything attached to the tool 608 inserted into the guide tube 1014 is known from the tracked markers 804 on the tool 608, the rotational orientation of the guide tube 1014 itself in the camera coordinate system is unknown without the additional tracking marker 1018 (or multiple tracking markers in other embodiments) on the guide tube 1014. This marker 1018 provides essentially a "clock position" from −180° to +180° based on the orientation of the marker 1018 relative to the centerline vector C'. Thus, the single marker 1018 can provide additional degrees of freedom to allow full rigid body tracking and/or can act as a surveillance marker to ensure that assumptions about the robot and camera positioning are valid.

FIG. 25 is a block diagram of a method 1100 for navigating and moving the end-effector 1012 (or any other end-effector described herein) of the robot 102 to a desired target trajectory. Another use of the single marker 1018 on the robotic end effector 1012 or guide tube 1014 is as part of the method 1100 enabling the automated safe movement of the robot 102 without a full tracking array attached to the robot 102. This method 1100 functions when the tracking cameras 200, 326 do not move relative to the robot 102 (i.e., they are in a fixed position), the tracking system's coordinate system and robot's coordinate system are co-registered, and the robot 102 is calibrated such that the position and orientation of the guide tube 1014 can be accurately determined in the robot's Cartesian coordinate system based only on the encoded positions of each robotic axis.

For this method 1100, the coordinate systems of the tracker and the robot must be co-registered, meaning that the coordinate transformation from the tracking system's Cartesian coordinate system to the robot's Cartesian coordinate system is needed. For convenience, this coordinate transformation can be a 4×4 matrix of translations and rotations that is well known in the field of robotics. This transformation will be termed Tcr to refer to "transformation—camera to robot". Once this transformation is known, any new frame of tracking data, which is received as x,y,z coordinates in vector form for each tracked marker, can be multiplied by the 4×4 matrix and the resulting x,y,z coordinates will be in the robot's coordinate system. To obtain Tcr, a full tracking array on the robot is tracked while it is rigidly attached to the robot at a location that is known in the robot's coordinate system, then known rigid body methods are used to calculate the transformation of coordinates. It should be evident that any tool 608 inserted into the guide tube 1014 of the robot 102 can provide the same rigid body information as a rigidly attached array when the additional marker 1018 is also read. That is, the tool 608 need only be inserted to any position within the guide tube 1014 and at any rotation within the guide tube 1014, not to a fixed position and orientation. Thus, it is possible to determine Tcr by inserting any tool 608 with a tracking array 612 into the guide tube 1014 and reading the tool's array 612 plus the single marker 1018 of the guide tube 1014 while at the same time determining from the encoders on each axis the current location of the guide tube 1014 in the robot's coordinate system.

Logic for navigating and moving the robot 102 to a target trajectory is provided in the method 1100 of FIG. 25. Before entering the loop 1102, it is assumed that the transformation Tcr was previously stored. Thus, before entering loop 1102, in step 1104, after the robot base 106 is secured, greater than or equal to one frame of tracking data of a tool inserted in the guide tube while the robot is static is stored; and in step 1106, the transformation of robot guide tube position from camera coordinates to robot coordinates Tcr is calculated from this static data and previous calibration data. Tcr should remain valid as long as the cameras 200, 326 do not move relative to the robot 102. If the cameras 200, 326 move relative to the robot 102, and Tcr needs to be re-obtained, the system 100, 300, 600 can be made to prompt the user to insert a tool 608 into the guide tube 1014 and then automatically perform the necessary calculations.

In the flowchart of method 1100, each frame of data collected consists of the tracked position of the DRB 1404 on the patient 210, the tracked position of the single marker 1018 on the end effector 1014, and a snapshot of the positions of each robotic axis. From the positions of the robot's axes, the location of the single marker 1018 on the end effector 1012 is calculated. This calculated position is compared to the actual position of the marker 1018 as recorded from the tracking system. If the values agree, it can be assured that the robot 102 is in a known location. The transformation Tcr is applied to the tracked position of the DRB 1404 so that the target for the robot 102 can be provided in terms of the robot's coordinate system. The robot 102 can then be commanded to move to reach the target.

After steps 1104, 1106, loop 1102 includes step 1108 receiving rigid body information for DRB 1404 from the tracking system; step 1110 transforming target tip and trajectory from image coordinates to tracking system coordinates; and step 1112 transforming target tip and trajectory from camera coordinates to robot coordinates (apply Tcr). Loop 1102 further includes step 1114 receiving a single stray marker position for robot from tracking system; and step 1116 transforming the single stray marker from tracking system coordinates to robot coordinates (apply stored Tcr). Loop 1102 also includes step 1118 determining current location of the single robot marker 1018 in the robot coordinate system from forward kinematics. The information from steps 1116 and 1118 is used to determine step 1120 whether the stray marker coordinates from transformed tracked position agree with the calculated coordinates being less than a given tolerance. If yes, proceed to step 1122, calculate and apply robot move to target x, y, z and trajectory. If no, proceed to step 1124, halt and require full array insertion into guide tube 1014 before proceeding; step 1126 after array is inserted, recalculate Tcr; and then proceed to repeat steps 1108, 1114, and 1118.

This method 1100 has advantages over a method in which the continuous monitoring of the single marker 1018 to verify the location is omitted. Without the single marker 1018, it would still be possible to determine the position of the end effector 1012 using Tcr and to send the end-effector 1012 to a target location but it would not be possible to verify that the robot 102 was actually in the expected location. For example, if the cameras 200, 326 had been bumped and Tcr was no longer valid, the robot 102 would move to an erroneous location. For this reason, the single marker 1018 provides value with regard to safety.

For a given fixed position of the robot 102, it is theoretically possible to move the tracking cameras 200, 326 to a new location in which the single tracked marker 1018 remains unmoved since it is a single point, not an array. In such a case, the system 100, 300, 600 would not detect any error since there would be agreement in the calculated and tracked locations of the single marker 1018. However, once the robot's axes caused the guide tube 1012 to move to a new location, the calculated and tracked positions would disagree and the safety check would be effective.

The term "surveillance marker" may be used, for example, in reference to a single marker that is in a fixed location relative to the DRB 1404. In this instance, if the DRB 1404 is bumped or otherwise dislodged, the relative location of the surveillance marker changes and the surgeon 120 can be alerted that there may be a problem with navigation. Similarly, in the embodiments described herein, with a single marker 1018 on the robot's guide tube 1014, the system 100, 300, 600 can continuously check whether the cameras 200, 326 have moved relative to the robot 102. If registration of the tracking system's coordinate system to the robot's coordinate system is lost, such as by cameras 200, 326 being bumped or malfunctioning or by the robot malfunctioning, the system 100, 300, 600 can alert the user and corrections can be made. Thus, this single marker 1018 can also be thought of as a surveillance marker for the robot 102.

It should be clear that with a full array permanently mounted on the robot 102 (e.g., the plurality of tracking markers 702 on end-effector 602 shown in FIGS. 16A-16C) such functionality of a single marker 1018 as a robot surveillance marker is not needed because it is not required that the cameras 200, 326 be in a fixed position relative to the robot 102, and Tcr is updated at each frame based on the tracked position of the robot 102. Reasons to use a single marker 1018 instead of a full array are that the full array is more bulky and obtrusive, thereby blocking the surgeon's view and access to the surgical field 208 more than a single marker 1018, and line of sight to a full array is more easily blocked than line of sight to a single marker 1018.

Turning now to FIGS. 26A-26B and 27A-27B, instruments 608, such as implant holders 608B, 608C, are depicted which include both fixed and moveable tracking markers 804, 806. The implant holders 608B, 608C may have a handle 620 and an outer shaft 622 extending from the handle 620. The shaft 622 may be positioned substantially perpendicular to the handle 620, as shown, or in any other suitable orientation. An inner shaft 626 may extend through the outer shaft 622 with a knob 628 at one end. Implant 10, 12 connects to the shaft 622, at the other end, at tip 624 of the implant holder 608B, 608C using typical connection mechanisms known to those of skill in the art. The knob 628 may be rotated, for example, to expand or articulate the implant 10, 12. U.S. Pat. Nos. 8,709,086 and 8,491,659, which are incorporated by reference herein, describe expandable fusion devices and methods of installation.

When tracking the tool 608, such as implant holder 608B, 608C, the tracking array 612 may contain a combination of fixed markers 804 and one or more moveable markers 806 which make up the array 612 or is otherwise attached to the implant holder 608B, 608C. The navigation array 612 may include at least one or more (e.g., at least two) fixed position markers 804, which are positioned with a known location relative to the implant holder instrument 608B, 608C. These fixed markers 804 would not be able to move in any orientation relative to the instrument geometry and would be useful in defining where the instrument 608 is in space. In addition, at least one marker 806 is present which can be attached to the array 612 or the instrument itself which is capable of moving within a pre-determined boundary (e.g., sliding, rotating, etc.) relative to the fixed markers 804. The system 100, 300, 600 (e.g., the software) correlates the position of the moveable marker 806 to a particular position, orientation, or other attribute of the implant 10 (such as height of an expandable interbody spacer shown in FIGS. 26A-26B or angle of an articulating interbody spacer shown in FIGS. 27A-27B). Thus, the system and/or the user can determine the height or angle of the implant 10, 12 based on the location of the moveable marker 806.

In the embodiment shown in FIGS. 26A-26B, four fixed markers 804 are used to define the implant holder 608B and a fifth moveable marker 806 is able to slide within a pre-determined path to provide feedback on the implant height (e.g., a contracted position or an expanded position). FIG. 26A shows the expandable spacer 10 at its initial height, and FIG. 26B shows the spacer 10 in the expanded state with the moveable marker 806 translated to a different position. In this case, the moveable marker 806 moves closer to the fixed markers 804 when the implant 10 is expanded, although it is contemplated that this movement may be reversed or otherwise different. The amount of linear translation of the marker 806 would correspond to the height of the implant 10. Although only two positions are shown, it would be possible to have this as a continuous function whereby any given expansion height could be correlated to a specific position of the moveable marker 806.

Turning now to FIGS. 27A-27B, four fixed markers 804 are used to define the implant holder 608C and a fifth, moveable marker 806 is configured to slide within a predetermined path to provide feedback on the implant articulation angle. FIG. 27A shows the articulating spacer 12 at its initial linear state, and FIG. 27B shows the spacer 12 in an articulated state at some offset angle with the moveable marker 806 translated to a different position. The amount of linear translation of the marker 806 would correspond to the articulation angle of the implant 12. Although only two positions are shown, it would be possible to have this as a continuous function whereby any given articulation angle could be correlated to a specific position of the moveable marker 806.

In these embodiments, the moveable marker 806 slides continuously to provide feedback about an attribute of the implant 10, 12 based on position. It is also contemplated that there may be discreet positions that the moveable marker 806 must be in which would also be able to provide further information about an implant attribute. In this case, each discreet configuration of all markers 804, 806 correlates to a specific geometry of the implant holder 608B, 608C and the implant 10, 12 in a specific orientation or at a specific height. In addition, any motion of the moveable marker 806 could be used for other variable attributes of any other type of navigated implant.

Although depicted and described with respect to linear movement of the moveable marker 806, the moveable marker 806 should not be limited to just sliding as there may be applications where rotation of the marker 806 or other movements could be useful to provide information about the implant 10, 12. Any relative change in position between the set of fixed markers 804 and the moveable marker 806 could be relevant information for the implant 10, 12 or other device. In addition, although expandable and articulating implants 10, 12 are exemplified, the instrument 608 could work with other medical devices and materials, such as spacers, cages, plates, fasteners, nails, screws, rods, pins, wire structures, sutures, anchor clips, staples, stents, bone grafts, biologics, or the like.

According to principles of the present invention, a system 420 is provided for registering patient images from a navigated imaging device 10 in an imaging space to the actual patient anatomy in a camera space without the use of any radiopaque fiducials embedded in the images. General embodiments of the invention include an intraoperative imaging system 10, a navigation and/or robotic guidance system 100, and an imaging transferring and data tracking device (I/O) 42,52.

The intraoperative imaging system 10 is capable of: (1) capturing 3-Dimensional (3D) images (e.g., CT, CBCT, MCT, PET, Angiogram, MRI, ultrasound, etc.), (2) capturing 2-Dimensional (2D) images (e.g., fluoroscopy, digital radiography, ultrasound, etc.), and (3) containing an integrated or detachable navigation array 68 having tracking markers (e.g., NIR retroreflective, NIR LED, visible, etc.), which is calibrated to the image space of the 2D and 3D images.

The navigation and/or robotic guidance system 100 is capable of: (1) using registered 2D and/or 3D images for surgical planning, navigation, and guidance in a variety of workflows (e.g., intraoperative 3D, intraoperative 2D, preoperative 3D to 2D, and intraoperative 3D to 2D, etc.), (2) containing an integrated or detachable stereoscopic tracking camera 200 capable of tracking markers 116, 68, 702. 612, 804 (e.g., NIR retroreflective, NIR LED, visible, etc.).

The patient reference array (DRB 116) is (1) capable of rigidly attaching to the patient anatomy, and (2) contains an array of tracking markers (e.g., NIR retroreflective, NIR LED, visible, etc.).

The imaging transferring and data tracking device (I/O) 42,52 connected between the imaging system 10 and navigation system 100 (e.g., wired data transfer, wireless data transfer, data transfer via portable storage device, etc.) is (1) capable of transferring complete patient registration information and associated images, and (2) capable of identifying and establishing unique peer-to-peer connection based on system type compatibility of sender of images (intraoperative imaging system) and receiver of images (navigation and/or robotic guidance system).

The motors 66, 67, 102 that move the gantry have encoders that track the position of the inner and outer C-arms 70,72, and therefore the position of the detector panel that detects the x-ray transmission. Specifically, the system tracks the pitch (rainbow), roll (tilt), and even yaw (using the encoder in the motor that rotates the vertical shaft 59). Alternatively, a separate tracking array can be attached to either the x-ray transmitter or the detector panel at known locations to track the detector position.

In the embodiment as shown in FIG. 28, the registration is performed using a transform matrix, in particular a homogeneous transform matrix T, discussed below although any other processing methods could be used.

As used herein, a homogeneous transform matrix T has four rows and four columns representing the 3-dimensional geometric positioning between two rigid bodies, an example of which is shown below.

| r1x | r2x | r3x | px |
|-----|-----|-----|-----|
| r1y | r2y | r3y | py |
| r1z | r2z | r3z | pz |
| 0   | 0   | 0   | 1  |

Encoded within this matrix T is both the relative rotation/orientation and position/translation. Orientation is represented as a rotation matrix consisting of three rows and three columns, as shown above, with each column defining to the rotation about x,y, and z axes and consisting of a 3-dimensional mutually orthogonal unit vectors having x,y, and z components. The relative position/translation is represented as a 3-dimensional vector consisting of x, y, and z component (as shown above with 'px', 'py' and 'pz') of these two bodies. The last row of [0,0,0,1] is an optional row and is used to simplify the math to allow an entire transformation (both rotation and translation) in a single matrix operation. This transform matrix T can then be used to wholly define the shift in 3-dimensional pose (position and orientation) between two bodies in 3-dimensional space.

Assume that there are two similar bodies (body A and body B) in space or two positions of the same body (position A and position B). the homogeneous transform T defining the shift from the pose of B relative to the pose of A can be denoted as A_X_B. If there is a third body or position, C and its pose relative to B is defined as B_X_C, the pose of C relative to A can then be computed by multiplying these two transforms together: A_X_B*B_X_C=A_X_C.

In the context of registration in a navigated surgery, one objective can be defined as computing the homogeneous transform T between the patient and the image IM taken by the imaging device 10. For the patient pose, the DRB 116 can be used as it is firmly attached to the patient. Thus, the transform between the patient and the image IM can be represented as "DRB_X_IM", i.e., a transform that defines the relative position and orientation of DRB 116 at the time of imaging relative to the position and orientation of the x-ray image IM.

As discussed previously, the DRB 116 includes an array of image tracking markers and serves as the optical tracker denoting the coordinate system of the patient. Image IM is the coordinate system of the image captured by the imaging system 10 such as Excelsius3D (hereinafter "E3D"), available at Globus Medical, Inc. of Audubon, PA. The image IM may be a 3D scan (e.g., CT scan or MRI) or 2D Fluoroscopy/Radiography shots.

With the above introduction to the homogeneous transform T between rigid bodies, a method of registering a patient image IM in an imaging space to the physical patient in a physical space, preferably without the use of any radiopaque fiducials embedded in the patient image will now be described.

DRB_X_Image is a transform between the origin of the DRB's coordinate system and the origin of the image's coordinate system. There are many different standards in terms of defining the location and directionality of the coordinate system of medical images. For example, an LPS (left, posterior, superior) standard may be used which puts the origin at the anterior, inferior, patient right corner of the image space. The axes of this 3D coordinate system point posteriorly, superiorly, and towards patient left from the origin (hence the LPS shorthand).

This DRB_X_Image transform (transform C) thus yields the relative pose between the patient's physical coordinate system via patient reference array DRB 116 in the physical space and the patient's virtual coordinate system embedded in the image IM in the image space. This is defined as the "patient registration". This transform process is what allows the surgical robot system 100 to virtually track tools on a 3D scan/2D shot and also provide navigated guidance to the robotic arm 104 and end effector 112 to know where to move relative to the patient based on a trajectory plan in the virtual image IM space. This registration is computed automatically by a processor of the imaging system 10 at the time the image IM is captured.

To compute DRB_X_Image (transform C), a few intermediate transforms (transforms A and B) are computed at the time that the image IM is taken. The tracking device 200 (camera system) includes a computing system which is similar to the system of FIG. 2 and is able to track the optical tracking markers of both the DRB 116 and E3D array 68 (denoted as "E3D" for the sake of transform notation) mounted to the gantry mount 58 and gather their relative pose with respect to the camera: DRB_X_Camera and E3D_X_Camera. E3D_X_Camera can be inverted (the mathematical operation of matrix inversion) to yield Camera_X_E3D. Multiplying these two matrices together yields: DRB_X_Camera*Camera_X_E3D=DRB_X_E3D. This transform (transform A), DRB_X_E3D, thus denotes the pose of the E3D 68 relative to the DRB 116.

A second transform (transform B), E3D_X_Image, is also calculated. E3D_X_Image is derived in a two-fold operation: E3D_X_Detector 76, and Detector_X_Image ("Detector" denotes the coordinate system of the x-ray detector panel 76 on the E3D).

E3D_X_Detector is computed from the kinematic configuration of the E3D 10. This is mechanical in nature, and represents the geometric configuration between the E3D array 68 and the detector panel 76. The position and orientation of the detector panel 76 relative to the array 68 is derived from information from encoders in the motors 66, 67, 102, and other motors in the gantry mount 58 and gantry 56. Alternatively, a separate optical array fixture mounted to either the detector panel 76 or the x-ray transmitter 74 may be used.

Detector_X_Image is gathered from the image construction process and is a property of the layout of the x-ray detector/transmitter and how the imaging device 10 constructs the resulting image. Multiplying these two transforms together yields: E3D_X_Detector*Detector_X_Image=E3D_X_Image (transform B).

To compute the overall patient registration, the two previously computed transforms, DRB_X_E3D (transform A) and E3D_X_Image (transform B), are multiplied together to yield: DRB_X_E3D*E3D_X_Image=DRB_X_Image (transform C, which represents the overall patient registration transform).

In determining E3D_X_Detector as part of deriving transform B, the imaging device 10 may need to be calibrated as the C-arms flex in varying amounts depending on their orientation. When the E3D 10 tilts the gantry 70 to non-zero angles, there is a certain amount of mechanical flex of the gantry due to gravity pulling down on the gantry. This flex may cause minor discrepancies in the E3D_X_Detector transform, as the kinematic configuration of these two mechanical pieces changes (on the order of several millimeters in some cases). The amount of flex is dependent on the system itself as well as how much gantry tilt is used. Thus, this calibration process is completed for each individual system 10 and over a grid of gantry tilt and rotor angles. This calibration process involves a radiotranslucent calibration fixture 416 with embedded radiopaque fiducials 418 (e.g., BBs), which are visible under x-ray. The fixture 416 also has optical markers 420 on one side, which are visible to the camera 200, yielding a Fixture_X_Camera transform. The location of the fiducials 418 relative to the markers 420 on the fixture 416 is a known transform based on the manufacturing of the fixture itself. This transform is mechanical in nature, and yields BBs_X_Fixture. Multiplying these two transforms together yields: BBs_X_Fixture*Fixture_X_Camera=BBs_X_Camera. Since the position of the E3D (or its array 68) with respect to the camera 200, E3D_X_Camera, is known, the BBs_X_Camera transform can be inverted and the following can me computed: E3D_X_Camera*Camera_X_BBs=E3D_X_BBs. This E3D_X_BBs transform represents the true flex-compensated physical pose of the fixture BBs 416 relative to the E3D array 68.

When an x-ray image/CT scan of the calibration fixture 416 is taken with the E3D 10, the radiopaque BBs 416 appear in the image. Their position within the image can be detected utilizing image processing algorithms. Combining this positioning with the known E3D_X_Image yields: E3D_X_Detector*Detector_X_Image*Image_X_DetectedBBs=E3D_X_DetectedBBs. This E3D_X_DetectedBBs transform represents the detected physical pose of the BBs 418 relative to the E3D array 68, following the registration pathway of computation, thus including potential errors via way of the E3D_X_Detector transform.

There is now two transforms representing the same physical pose between the BBs 418 and the E3D array 68: E3D_X_BBs and E3D_X_DetectedBBs. E3D_X_BBs represents the true pose (control value) and E3D_X_DetectedBBs represents the detected, potentially error prone, pose. The differences, both in terms of orientation and translation, between E3D_X_BBs and E3D_X_DetectedBBs is analyzed. This difference is stored in the memory of the imaging device 10 as an offset to be applied to E3D_X_Detector to account for the mechanical flex caused by gravity. This offset ensures that E3D_X_BBs and E3D_X_DetectedBBs will have the same resultant transform, ensuring sufficient accuracy in utilizing the E3D_X_Detector transform in the patient registration process.

This calibration process is completed across a large combination of tilt & rotor angles for the gantry 56 and preferably is completed separately for each individual system 10. The offset calibration data are stored on the system 10 memory and are utilized when completing the registration process, ensuring accuracy in the computed DRB_X_Image patient registration transform.

As an example, during a calibration procedure, the system 10 takes an image of a calibration frame/fixture 416 for every 10 degree rotation at a particular pitch angle, which means 36 images are taken. The same procedure is repeated at 10 degrees higher in pitch. Thus, 1,296 images are taken all together to calibrate the C-arms and stored. When the imaging system 10 is used to image an actual patient at angles other than at 10 degree increments, interpolation between two surrounding calibration data at degrees apart is used to fine tune the calibration data on the fly and is used to determine a patient registration transform which has been compensated for the mechanical flex of the gantry 56 at a particular position and orientation.

In one embodiment, for 2D calibrations, the E3D_X_FocalSpot (focal spot of the transmitter/imaging device 10) and E3D_X_Detector (detector panel of the imaging device) are stored in the memory. For a given acquired image, a camera model is used to calculate the location of the focal spot and detector panel with respect to the E3D 10 imaging markers 68. These calibration locations are determined for a series of tilt angles and rainbow angles and stored in a memory/file for future use. During use, the desired registration location is captured and the bounding calibration points are determined. There will be four corners. The focal spot and detector panel transforms are spherically bi-linearly interpolated to the resultant focal spot and detector positions and these are used to calculate the 4×4 projection matrix used by the navigation/robot system 100.

In one embodiment, for 3D calibrations, the E3D_X_image3D (3D image) transform at a series of tilt angles and stored in a memory/file for future use. During use, the desired registration location is captured and the bounding calibration points are determined. There will be two calibration transforms. These transforms will be spherically interpolated to create the desired E3D_X_image3D transform of the current location. This is the registration information (calculated by the imaging device 10) which is sent from the imaging device to the navigation/robotic system 100.

FIG. 29 is a flowchart of a method of registering an intra-op 3D image of a patient in an imaging space to the physical patient in a physical space, preferably without using any embedded radiopaque fiducials in images. This method does not require any pre-op images for patient registration purposes.

The steps of FIG. 29 and all other flowcharts in other figures are executed primarily by the imaging control module 54 of the imaging device 10, except where noted.

In step 422, the patient 210 is positioned on an operating table and a dynamic reference base ("DRB") 116 having an array of patient tracking markers 118 is securely attached to the patient anatomy (e.g., to the pelvic bone of the patient).

In step 424, the imaging system 10 is positioned within the operating area such that the cameras 200 has good visibility to the DRB 116 and an array of imaging tracking markers 68 on either side of the gantry mount 58.

In step 426, a tracking system/processor 532 of the robot system 100 begins to continuously track the calibrated pose (i.e., position and orientation) of the imaging device 10 from the imaging tracking markers 68 contained in optical images coming from the cameras 200.

In step 428, the tracking system 532 of the robot system 100 also begins to continuously track the patient pose via the DRB 116.

Once robotic system 100 to imaging device 10 connection is established through the I/O of the robotic system, the processor 408 of the robotic system starts sending camera frame data to the imaging device 10 through the communication link 52, which contains the relative location from the imaging tracking markers 68 to the DRB 116 in camera space (e.g., the continuously tracked data of the imaging device 10 and the DRB 116). The camera 200 uses whatever reference array 68 is visible (left or right arrays on both sides of the gantry mount 58).

In step 430, a 3D image of the patient anatomy of interest is captured by the imaging device 10 while the cameras 200 are tracking the DRB 116 and imaging tracking markers 68. As discussed earlier, the imaging device 10 is capable of rotating the inner and outer c-arms 70,72 to image the patient with a full 360 degree rotation. For example, the imaging device performs a full 3D x-ray CT scan, which is then converted into a 3D image or image volume based on a well-known CT conversion process, in which a series of X-ray images taken from different angles around the patient anatomy are processed by the processor 46 to create a series of cross-sectional slices of the patient anatomy. The series of cross-sectional slices are stored in the memory as a DICOM (digital imaging and communications in medicine) file which contains a header file and a series of image data each typically representing a corresponding cross-sectional slice.

In step 432, the 3D image obtained from step 430 is registered as discussed above. Specifically, DRB_X_Image as represented by transform C is derived by multiplying transform A and transform B. The tracking data required by the various transforms are received from the robot system 100 and stored in the memory 44 for use by the registration algorithm.

As discussed above, transform C represents the relative pose between the patient's physical coordinate system via patient reference array DRB 116 in the physical space as seen by the cameras 200 and the patient's virtual coordinate system embedded in the image IM in the image space. The transform C data is then embedded in the private tags/header section of the DICOM file representing the 3D image of the patient anatomy.

In step 434, the registered 3D image (transform C) in the form of a DICOM file which contains the registration information in the header is transferred from the imaging device 10 to the robotic system 100.

Software in the robotic system 100 then extracts the patient reference-to-scan transform (transform C) from the 3D image, stores it in the memory and uses it for navigation as other surgical instrument arrays are tracked with respect to the DRB 116 as the robotic system knows where the instruments are in the image space using the transform C.

In step 436, the imaging device 10 can now be removed from the operating area. In step 438, the robotic system 100 uses the registered 3D image for navigation and robotic surgery. For example, the robotic system 100 may move the end effector (which is also being tracked by the camera 200 through the markers 702) to place the end effector along a selected trajectory for inserting bone screws. The robotic system 100 may also display the registered 3D image on a display and manipulate the displayed image as the end effector is moved. The system 100 also displays a planned instrument trajectory, and a dynamically updated trajectory of an optically tracked surgical instrument 608 and end effector 112/114, and a virtual representation of the tracked instrument all of which are super imposed on the displayed 3D image and other displayed 2D images (A/P, lateral, and axial). Moreover, the system 100 can also display any number of 2D views of the 3D medical image such as, for example, A/P, lateral, and axial views, which are simulated fluoroscopic shots (e.g., DRR images) or planar slices that have been generated from the 3D image by image processing.

The robotic system 100 may also display a tracked surgical instrument which is superimposed on the displayed 3D image to assist the physician with visualization.

The robotic system can also display a variety of images on the display to assist the physician. For example, four distinct images including Ap, lateral, axial and probe's eye (3D) images can be displayed simultaneously. The axial view (either DRR image or slice image) which represents the view of a horizontal slice of the bone at the point of a planned trajectory is particularly useful and can be generated by synthesizing a correct slice or DRR image at a correct orientation from the 3D image.

In step 439, the robotic system 100 detects that the registration is compromised. This could be detected for example, if a distance from a surveillance marker to the DRB 116 changes beyond a threshold amount. Then, steps 424-438 are repeated to re-register the patient.

FIG. 30 is a flowchart of a method of registering an intra-op 3D image of a patient in an imaging space to the physical patient in a physical space and recovering registration of the 3D image with intra-op 2D images, preferably without using any embedded radiopaque fiducials in images.

Steps 422-439 of FIG. 30 in registering an intra-op 3D image are identical to those in FIG. 29. Once loss of registration is detected in step 439, step 440 is executed by the processor 46 of the imaging device 10.

In step 440, the imaging system 10 is brought back out and is positioned within the operating area such that the cameras 200 has good visibility to the DRB 116 and the array of imaging tracking markers 68 on either side of the gantry mount 58.

In step 442, the tracking system/processor 532 of the robot system 100 begins to continuously track the calibrated pose (i.e., position and orientation) of the imaging device 10 from the imaging tracking markers 68 contained in optical images coming from the cameras 200.

In step 444, the tracking system 532 of the robot system 100 also begins to continuously track the patient pose via the DRB 116.

Once robotic system 100 to imaging device 10 connection is established through the I/O of the robotic system, the processor 408 of the robotic system starts sending camera frame data to the imaging device 10 through the communication link 52, which contains the relative location from the imaging tracking markers 68 to the DRB 116 in camera space (e.g., the continuously tracked data of the imaging device 10 and the DRB 116). The camera 200 uses whatever reference array 68 is visible (left or right arrays on both sides of the gantry mount 58).

In step 446, a set of 2D images at two different orientations of the patient anatomy of interest, such as A/P and lateral, is captured by the imaging device 10. These images may be taken manually by a user or automatically by the imaging device which will rotate the second image by a pre-selected degrees, such as 90 degrees, from the first image.

For each image, the above discussed transforms (transforms A, B and C) are performed such that each image in the image space is registered to the physical patient in the patient coordinate system as represented in the form of the DRB 116.

The registration of each image can be performed in a few different methods. In a first method, the imaging device 10 is tracked using a fluoro fixture temporarily mounted to the fluoro collector (image intensifier or flat panel). One example of the fluoro fixture 2100 is disclosed in U.S. patent application Ser. No. 15/267,950, filed on Sep. 16, 2016 (U.S. Pat. No. 10,799,298), which is incorporated herein. This fixture has two planes of BBs, allowing fluoro images to be processed so that the tracked position of the fluoro x-ray emitter of the imaging device 10 can be accurately extrapolated from the tracked position of the fluoro collector, and thereby the image IM position in the imaging space.

In another variation of the method, preferably the imaging device is optically tracked with, for example, the imaging tracking markers 68, and the locations of the emitter and collector, and thereby the image IM are accurately extrapolated using the transforms (transforms A, B, and C) as discussed above.

With each image, the position of the DRB 116 that is mounted on the patient is simultaneously tracked by the same optical tracking system 200 while tracking the position of the imaging tracking markers 68, so that the image position in the imaging space is correlated to the DRB 116 coordinate system representing the patient's physical space. In other words, for each image, transform C is calculated as discussed above and the image is stored as a DICOM file with the header containing the associated registration information.

In step 446, the DICOM file is sent to the surgical robot system 100 through the communication link 52 for further processing. As can be appreciated, the DICOM file for the 2D images include spacing information, which include an angle and offset (displacement) of one 2D image relative to the other 2D image, which information may be used later for the merging operation.

In step 450, the imaging device 10 can now be removed from the operating area.

Step 452 is executed by the processor in the computer 408 of the robot system 100. In step 452, the registered 2D images are merged with the 3D image that was obtained in step 430.

In one method of merging, simulated fluoro shots called digitally reconstructed radiographs or DRRs are created from the 3D image. Each DRR image represents an artificially or synthetically created fluoroscopic image that is based on a particular orientation and position of a theoretical fluoro machine relative to the scan volume through image processing. In the case of 3D image derived from a CT scan volume, DRR images are generated by computing the pixel intensity intersected and accumulated by rays passing through the CT scan volume from a point source (emitter) on one side of the CT volume through a divergent path to a plane (collector) on the other side. Optionally, the DRR images, 2D images or 3D image volume may be processed with a high pass filter to enhance the contrast around bone boundaries.

At each comparison, two DRR images are generated at a selected angle and offset from each other. The selected angle and offset are based on the known (tracked) angle and offset that were used to capture the two 2D images (A/P and lateral) in step 446. In this way, the two generated DRR images can be compared to the two 2D images at the same time through an image processing algorithm. If the image content (gradient in contrast of bony edges) on the DRR images and the 2D images do not match everywhere within a given threshold, the theoretical position and orientation of the 3D image relative to the fixed locations of the x-ray collector and emitter from the 2D images are slightly modified and two new DRR images are generated.

When generating new DRR images, the direction and angle in which to nudge (incremental change in position and orientation) the 3D image volume relative to the fixed positions of the theoretical x-ray collector and emitter are based on whether the previous nudge (incremental change) caused an improvement or worsening offset in image content of DRR images relative to the actual 2D fluoroscopic images.

Iterations stop once further tweaking of the 3D image volume's orientation and position relative to the fixed positions of the theoretical x-ray collector and emitter no longer provides better matching of the 2D image content to the DRR images.

In an alternative embodiment, the matching is performed using a two step process whereby one of the two 2D images is matched to a particular DRR image using the above described merging method and then the other of the two 2D images is matched with the above merging method.

Once the positions of the theoretical emitter and collector are known relative to the image volume (3D image), registration is achieved because the theoretical emitter and collector positions provide the corresponding location in imaging space (e.g., CT space) to the known tracked positions of the actual emitter and collector in DRB 116 space. Thus, registration of the 3D image is recovered and the registration information is stored in the memory of the robot system 100.

In an alternative method of merging, when in step 446, an ultrasound transducer with imaging tracking markers is used to capture 2D images instead of the imaging device 10, simulated 2D ultrasound images are created from the 3D image volume. Each 2D ultrasound image represents an artificially or synthetically created ultrasound image from a theoretical ultrasound imaging handpiece held in a particular position relative to the 3D volume. In the case of a 3D image derived from a CT scan volume, synthetic 2D ultrasound images are generated by computing the pixel intensity intersected and accumulated by sound waves passing through the CT scan volume from an ultrasound source (emitter), reflecting from tissues of different types (bone, soft tissue, blood), and being monitored by the ultrasound receiver. Optionally, the simulated 2D ultrasound images, 3D image volume or both may be processed with a high pass filter to enhance the contrast around bone boundaries.

At each comparison, two simulated ultrasound images are generated at a selected angle and offset from each other. The selected angles are based on the angle and offset that was used to capture the two 2D tracked ultrasound images (A/P and lateral) in step 446. In this way, the two simulated 2D ultrasound images can be compared to the two actual 2D ultrasound images at the same time through an image processing algorithm. If the image content (gradient in contrast of bony edges) on the simulated and actual images do not match everywhere within a given threshold, the theoretical position and orientation of the 3D image volume relative to the fixed location of the theoretical ultrasound handpiece from the 2D images are slightly modified and two new simulated 2D ultrasound images are generated.

When generating new 2D simulated ultrasound images, the direction and angle in which to nudge (incremental change in position and orientation) the image volume relative to the positions of the theoretical ultrasound handpiece are based on whether the previous nudge (incremental change) caused an improvement or worsening offset in image content of 2D simulated ultrasound images relative to the 2D actual ultrasound images.

Iterations stop once further tweaking of the image volume orientation and position no longer provides better matching of the actual 2D ultrasound image content to the simulated 2D ultrasound images. The use of an ultrasound transducer to generate 2D images as described above may be used as an alternative method in any registration or registration recovery procedure that uses the imaging device 10.

In step 454, the robotic system 100 uses the registered 3D image (3D image with recovered registration) for navigation and robotic surgery such as for controlling its arms 104 and end effector 112, and contents of the displays 110. Similar to step 438, The processor/computer 408 displays the registered 3D image and the two 2D images (A/P and lateral) on the display 304 along with a planned instrument trajectory, and a dynamically updated trajectory of an optically tracked surgical instrument 608 and end effector 112/114, and a virtual representation of the tracked instrument, all of which are superimposed on the displayed 3D and 2D images.

In step 456, the robotic system 100 detects that the registration is compromised again. If so, control returns to step 440 and only the 2D images are required re-register the 3D image, instead of requiring another full 3D scan of the patient.

FIG. 31 is a flowchart of a method of registering a pre-op 3D image of a patient in an imaging space to the physical patient in a physical space and recovering registration of the 3D image with intra-op 2D images, preferably without using any embedded radiopaque fiducials in images.

Step 458, a 3D image of the patient anatomy of interest is captured by the imaging device 10 prior to the operation. For example, the imaging device 10 may perform a full 3D x-ray CT scan, which is then converted into a 3D image or image volume based on a well-known CT conversion process. The 3D image is then stored in the memory as a DICOM file.

Discussion of steps with the same reference numbers as those in the earlier figures have been omitted for brevity.

In step 456, the robotic system 100 detects that the registration has been compromised. If so, control passes to step 424 so that registration may be recovered using only the two 2D images (e.g., A/P and lateral) and merging them to the pre-op 3D image without doing another full 3D scan of the patient, thereby decreasing the overall procedure time and reducing the harmful x-ray exposure for the patient.

FIG. 32 is a flowchart of a method of registering intra-op 2D image of a patient in an imaging space to the physical patient in a physical space (as represented by a camera/optical space as shown in FIG. 28) and recovering registration of the 2D images with another set of intra-op 2D images, preferably without using any embedded radiopaque fiducials in images.

This method may be useful when there is no available 3D imaging system. Steps 422-428 and 446-454 in FIG. 32 are identical to those in other figures.

As part of step 454, the processor/computer 408 displays the registered 2D images (A/P and lateral) on the display 304 along with a dynamically updated trajectory of an optically tracked surgical instrument 608 and end effector 112/114 and a virtual representation of the tracked instrument.

In step 456, compromise of registration is detected by the robot system 100. If so, control passes to step 424 in which two additional 2D images are obtained from the imaging device 10 and registered by performing transforms A, B and C, with transform C ultimately representing the registration information between the 2D image in the imaging space and DRB 116 in the camera 200 space (physical patient coordinate system).

However, as can be appreciated by persons of ordinary skill in the art, it may not be easy to navigate based on only two 2D images that are displayed on the display 304. As an alternative to the method of FIG. 32 where there is no access to a 3D imaging device, a 3D image can be synthetically created from a generic model such as an Atlas model.

FIG. 33 is a flowchart of a method of registering a synthetically created 3D image based on an intra-op 2D image of a patient, preferably without using any embedded radiopaque fiducials in images. Image processing techniques such as statistical shape modeling and Artificial Intelligence or machine learning model techniques can be used to customize a generic model using the 2D images (e.g., A/P and lateral) from the patient. Thus, after step 448, the robotic system 100 generates a synthetically created 3D image based on a generic model and 2D images in step 460. One way to do this is to stretch and compress the generic 3D model based on the 2D images. Prior to doing so, the 2D images can be processed for segmentation to identify each vertebral level and their well-known points.

In step 452, the registered 2D images are merged with the customized 3D image that was obtained in step 460, and then the registered synthetic 3D image in addition to the two 2D images are displayed on the display 304. In that way, navigation using tracked instruments, its trajectory and end effector which are displayed and superimposed on the displayed 3D and 2D images may be easier to visualize and more accurate.

Alternatively, steps 460 and 452 are performed simultaneously or in reverse order as once the generic 3D model has been customized, the pose of the customized model will already have been synchronized to the 2D images. In that case, the registration step is simply a matter of transferring the 3D image pose information (one that matches the orientation of the 2D images) into a form that can be used by the surgical robot system 100.

These and other advantages of the present invention will be apparent to those skilled in the art from the foregoing specification. Accordingly, it will be recognized by those skilled in the art that changes or modifications may be made to the above-described embodiments without departing from the broad inventive concepts of the invention. It should therefore be understood that this invention is not limited to the particular embodiments described herein, but is intended to include all changes and modifications that are within the scope and spirit of the invention as defined in the claims.

What is claimed is:

1. A system for intra-operatively registering a 3D patient image comprising:
   a portable imaging system having an outer c-arm, an inner c-arm rotatably coupled to the outer c-arm, and a transmitter and a detector both attached to one of the c-arms, the outer and inner c-arms together providing a 360 degree rotation of the detector, the imaging system further having an imaging tracking marker array (ITMA);
   a dynamic reference base (DRB) including patient tracking markers and attachable to a patient;
   a tracking device having a plurality of cameras configured to track a position and orientation of both the ITMA and the DRB simultaneously;
   a processor adapted to generate a 3D image volume from intra-operative medical images that have been captured from a 360 degree rotation of the detector around the patient and register the 3D image volume relative to the patient by performing the following:
      receive optical images of the patient from the tracking device at the time of image capture, the optical images containing the ITMA and the DRB;
      determine transform A representing the pose of the imaging system in the imaging space relative to the DRB in the physical space at the time the medical images are captured based on the received optical images;
      determine transform B representing the pose of the medical images in the imaging space relative to the imaging system in the physical space based on the received optical images; and
      determine transform C by multiplying transform A with transform B, the transform C representing a registration of the 3D image volume relative to the DRB in the physical space.

2. The system of claim 1, wherein the processor is configured to determine the transform A by:
   generating a transform A1 representing the pose of the DRB relative to the cameras of the tracking device;
   generating a transform A2 representing the pose of the ITMA relative to the cameras of the tracking device;
   multiplying the transform A1 and the transform A2 together.

3. The system of claim 2, wherein the processor generates an inverse of the transform A2 prior to multiplying.

4. The system of claim 1, wherein the processor is configured to determine the transform B by:
   generating a transform B1 representing the pose of the detector relative to the ITMA of the imaging system;
   generating a transform B2 representing the pose of the medical images in the imaging space relative to the detector;
   multiplying the transform B1 and the transform B2 together.

5. The system of claim 1, wherein the processor is configured to determine the transform B by determining a spatial relationship between the medical images and the ITMA which has been adjusted with calibration data related to the amount of flex of at least one of the c-arms at different orientation of the imaging system.

6. The system of claim 1, wherein the processor is configured to display the 3D image volume on a display and superimposes a planned trajectory of a surgical instrument, and dynamically adjust the displayed trajectory over the displayed 3D image volume as the trajectory is varied by a user based on the registration information of the 3D image volume.

7. The system of claim 1, further comprising a surgical robot configured to assist in a surgical operation of the patient and be in communication with the imaging system, the surgical robot including a base, a robot arm coupled to the base, an end effector coupled to the robot arm and a robot processor, wherein:

under control of the imaging system, the processor is configured to:
attach registration information in an image file of the 3D image volume; and
transfer the image file containing the 3D image volume and the registration information from the imaging system to the surgical robot; and
wherein the robot processor of the surgical robot is configured to display the 3D image volume on a display and superimpose a planned trajectory of a surgical instrument, and dynamically adjust the displayed trajectory over the displayed 3D image volume as the trajectory is varied by a user based on the registration information of the 3D image volume.

8. The system of claim 1, wherein the imaging system further comprises a gantry coupled to the c-arms, wherein the ITMA is attached to the gantry.

9. The system of claim 8, wherein the processor is configured to determine the spatial relationship between the ITMA and the detector based on information from encoders attached to the c-arms.

10. The system of claim 9, wherein determining transform B includes determining a spatial relationship between the 2D image and the imaging tracking markers which has been adjusted with calibration data related to the amount of flex at different orientation of the imaging device.

11. A system for intra-operatively registering a 3D patient image comprising:

a portable imaging system having an outer c-arm, an inner c-arm rotatably coupled to the outer c-arm, and a transmitter and a detector both attached to one of the c-arms, the outer and inner c-arms together providing a 360 degree rotation of the detector, the imaging system further having an imaging tracking marker array (ITMA);
a dynamic reference base (DRB) including patient tracking markers and attachable to a patient;
a tracking device having a plurality of cameras configured to track a position and orientation of both the ITMA and the DRB simultaneously;
a processor adapted to generate a 3D image volume from a plurality of intra-operative medical images that have been captured from a 360 degree rotation of the detector around the patient and register the 3D image volume relative to the patient by performing the following:
receive optical images of the patient from the tracking device at the time of image capture, the optical images containing the ITMA and the DRB attached to the patient;
determine transform A representing the pose of the ITMA of the imaging system in the imaging space relative to the DRB in the physical space at the time the medical images are captured based on the ITMA and DRB contained in the received optical images;
determine transform B representing the pose of the medical images in the imaging space relative to the imaging system in the physical space based on the ITMA contained in the received optical images; and
determine transform C by multiplying transform A with transform B, the transform C representing a registration of the 3D image volume relative to the DRB attached to the patient in the physical space.

12. The system of claim 11, wherein the processor is configured to determine the transform A by:
generating a transform A1 representing the pose of the DRB relative to the cameras of the tracking device;
generating a transform A2 representing the pose of the ITMA relative to the cameras of the tracking device;
multiplying the transform A1 and the transform A2 together.

13. The system of claim 12, wherein the processor generates an inverse of the transform A2 prior to multiplying.

14. The system of claim 11, wherein the processor is configured to determine the transform B by:
generating a transform B1 representing the pose of the detector relative to the ITMA of the imaging system;
generating a transform B2 representing the pose of the medical images in the imaging space relative to the detector;
multiplying the transform B1 and the transform B2 together.

15. The system of claim 11, wherein the processor is configured to determine the transform B by determining a spatial relationship between the medical images and the ITMA which has been adjusted with calibration data related to the amount of flex of at least one of the c-arms at different orientation of the imaging system.

16. The system of claim 11, wherein the processor is configured to display the 3D image volume on a display and superimposes a planned trajectory of a surgical instrument, and dynamically adjust the displayed trajectory over the displayed 3D image volume as the trajectory is varied by a user based on the registration information of the 3D image volume.

17. The system of claim 11, further comprising a surgical robot configured to assist in a surgical operation of the patient and be in communication with the imaging system, the surgical robot including a base, a robot arm coupled to the base, an end effector coupled to the robot arm and a robot processor, wherein:

under control of the imaging system, the processor is configured to:
attach registration information in an image file of the 3D image volume; and
transfer the image file containing the 3D image volume and the registration information from the imaging system to the surgical robot; and
wherein the robot processor of the surgical robot is configured to display the 3D image volume on a display and superimpose a planned trajectory of a surgical instrument, and dynamically adjust the displayed trajectory over the displayed 3D image volume as the trajectory is varied by a user based on the registration information of the 3D image volume.

18. The system of claim 11, wherein the imaging system further comprises a gantry coupled to the c-arms, wherein the ITMA is attached to the gantry.

19. The system of claim 18, wherein the processor is configured to determine the spatial relationship between the ITMA and the detector based on information from encoders attached to the c-arms.

20. The system of claim 19, wherein determining transform B includes determining a spatial relationship between the 2D image and the imaging tracking markers which has been adjusted with calibration data related to the amount of flex at different orientation of the imaging device.

* * * * *